US009121035B2

(12) United States Patent
Baum et al.

(10) Patent No.: US 9,121,035 B2
(45) Date of Patent: Sep. 1, 2015

(54) INSECTICIDAL COMPOSITIONS AND METHODS FOR MAKING INSECT-RESISTANT TRANSGENIC PLANTS

(75) Inventors: James A. Baum, Webster Groves, MO (US); James K. Roberts, Chesterfield, MO (US); Bei Zhang, Chesterfield, MO (US); Heather Anderson, Wildwood, MO (US); Catherine A. Chay, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 900 days.

(21) Appl. No.: 12/064,840

(22) PCT Filed: Aug. 30, 2006

(86) PCT No.: PCT/US2006/033867

§ 371 (c)(1),
(2), (4) Date: Feb. 26, 2008

(87) PCT Pub. No.: WO2007/027776

PCT Pub. Date: Mar. 8, 2007

(65) Prior Publication Data

US 2009/0068159 A1 Mar. 12, 2009

Related U.S. Application Data

(60) Provisional application No. 60/713,111, filed on Aug. 31, 2005.

(51) Int. Cl.

*C12N 15/82* (2006.01)
*C07K 14/325* (2006.01)
*A01N 63/02* (2006.01)

(52) U.S. Cl.

CPC ............ *C12N 15/8286* (2013.01); *A01N 63/02* (2013.01); *C07K 14/325* (2013.01); *C12N 15/8216* (2013.01); *C12N 15/8257* (2013.01)

(58) Field of Classification Search

None
See application file for complete search history.

(56) References Cited

U.S. PATENT DOCUMENTS 6,093,695 A * 7/2000 Rupar et al. .................... 514/12

* cited by examiner

*Primary Examiner* — Anne Kubelik

(74) *Attorney, Agent, or Firm* — Thompson Coburn LLP; J. Wendy Davis

(57) ABSTRACT

The present invention provides isolated polynucleotide sequences encoding ET37, TIC810 and TIC812 proteins from *Bacillus thuringiensis*, and nucleotide sequences for use in expressing TIC809, ET37, TIC810 and TIC812, and fusions of various insecticidally effective combinations of these proteins such as TIC 127, in plants. Methods of making and using the polynucleotide sequences and the proteins in the development of transgenic plant cells and transgenic plants exhibiting improved insect resistance against (1) Coleopteran insects including Western Corn Rootworm (*Dibrotica virgifera*), Southern Corn Rootworm (*Dibrotica undecempunctata*), Northern Corn Rootworm (*Diabrotica barbed*), Mexican Corn Rootworm (*Diabrotica virgifera zeae*), Brazilian Corn Rootworm (*Diabrotica balteata*) and Brazilian Corn Rootworm complex (*Diabrotica viridula* and *Diabrotica speciosa*), and against Hemipteran insects such as *Lygus* bugs, are disclosed.

24 Claims, No Drawings

SEQUENCE LISTING

```
<160> NUMBER OF SEQ ID NOS: 47

<210> SEQ ID NO 1
<211> LENGTH: 696
<212> TYPE: DNA
<213> ORGANISM: Bacillus thuringiensis
<220> FEATURE:
<221> NAME/KEY: CDS
<222> LOCATION: (1)..(696)
<223> OTHER INFORMATION: ET37

<400> SEQUENCE: 1

atg ttc ttt aat cgc gtt att aca tta aca gta cca tct tca gat gtg       48
Met Phe Phe Asn Arg Val Ile Thr Leu Thr Val Pro Ser Ser Asp Val
1               5                   10                  15

gtt aat tat agt gaa att tat cag gta gct cca caa tat gtg aat caa       96
Val Asn Tyr Ser Glu Ile Tyr Gln Val Ala Pro Gln Tyr Val Asn Gln
            20                  25                  30

gct ctt acg cta gct aaa tat ttc caa gga gca att gat ggt tca aca      144
Ala Leu Thr Leu Ala Lys Tyr Phe Gln Gly Ala Ile Asp Gly Ser Thr
        35                  40                  45

tta cgt ttt gat ttt gaa aaa gcc tta caa att gca aat gat att cca      192
Leu Arg Phe Asp Phe Glu Lys Ala Leu Gln Ile Ala Asn Asp Ile Pro
    50                  55                  60

cag gca gca gtg gta aac act tta aat caa act gtg cag caa ggt aca      240
Gln Ala Ala Val Val Asn Thr Leu Asn Gln Thr Val Gln Gln Gly Thr
65                  70                  75                  80

gtc caa gta tca gtg atg ata gac aag att gta gac att atg aag aat      288
Val Gln Val Ser Val Met Ile Asp Lys Ile Val Asp Ile Met Lys Asn
                85                  90                  95

gta tta tct att gta att gat aac aaa aag ttt tgg gat cag gta aca      336
Val Leu Ser Ile Val Ile Asp Asn Lys Lys Phe Trp Asp Gln Val Thr
            100                 105                 110

gct gct att aca aat aca ttc aca aat cta aat tcg caa gaa agc gaa      384
Ala Ala Ile Thr Asn Thr Phe Thr Asn Leu Asn Ser Gln Glu Ser Glu
        115                 120                 125

gca tgg att ttt tat tac aaa gaa gat gca cat aaa act agt tac tat      432
Ala Trp Ile Phe Tyr Tyr Lys Glu Asp Ala His Lys Thr Ser Tyr Tyr
    130                 135                 140

tat aat atc tta ttt gct ata cag gat gag gaa aca ggt ggg gta atg      480
```

-continued

```
Tyr Asn Ile Leu Phe Ala Ile Gln Asp Glu Glu Thr Gly Gly Val Met
145                 150                 155                 160

gcg aca tta ccg att gca ttt gat att agt gta gat att gaa aaa gaa      528
Ala Thr Leu Pro Ile Ala Phe Asp Ile Ser Val Asp Ile Glu Lys Glu
                165                 170                 175

aag gtt cta ttt gtt act atc aag gat act gaa aat tat gct gtt aca      576
Lys Val Leu Phe Val Thr Ile Lys Asp Thr Glu Asn Tyr Ala Val Thr
            180                 185                 190

gta aaa gct att aat gta gta caa gca ctt caa tct tcc cga gat tca      624
Val Lys Ala Ile Asn Val Val Gln Ala Leu Gln Ser Ser Arg Asp Ser
        195                 200                 205

aaa gtt gta gat gct ttt aaa tcg cca cgt cac tta cct aga aaa aga      672
Lys Val Val Asp Ala Phe Lys Ser Pro Arg His Leu Pro Arg Lys Arg
    210                 215                 220

cat aca att tgt agt aac tct taa                                      696
His Thr Ile Cys Ser Asn Ser
225                 230


<210> SEQ ID NO 2
<211> LENGTH: 231
<212> TYPE: PRT
<213> ORGANISM: Bacillus thuringiensis

<400> SEQUENCE: 2

Met Phe Phe Asn Arg Val Ile Thr Leu Thr Val Pro Ser Ser Asp Val
1               5                   10                  15

Val Asn Tyr Ser Glu Ile Tyr Gln Val Ala Pro Gln Tyr Val Asn Gln
            20                  25                  30

Ala Leu Thr Leu Ala Lys Tyr Phe Gln Gly Ala Ile Asp Gly Ser Thr
        35                  40                  45

Leu Arg Phe Asp Phe Glu Lys Ala Leu Gln Ile Ala Asn Asp Ile Pro
    50                  55                  60

Gln Ala Ala Val Val Asn Thr Leu Asn Gln Thr Val Gln Gln Gly Thr
65                  70                  75                  80

Val Gln Val Ser Val Met Ile Asp Lys Ile Val Asp Ile Met Lys Asn
                85                  90                  95

Val Leu Ser Ile Val Ile Asp Asn Lys Lys Phe Trp Asp Gln Val Thr
            100                 105                 110

Ala Ala Ile Thr Asn Thr Phe Thr Asn Leu Asn Ser Gln Glu Ser Glu
        115                 120                 125

Ala Trp Ile Phe Tyr Tyr Lys Glu Asp Ala His Lys Thr Ser Tyr Tyr
    130                 135                 140

Tyr Asn Ile Leu Phe Ala Ile Gln Asp Glu Glu Thr Gly Gly Val Met
145                 150                 155                 160

Ala Thr Leu Pro Ile Ala Phe Asp Ile Ser Val Asp Ile Glu Lys Glu
                165                 170                 175

Lys Val Leu Phe Val Thr Ile Lys Asp Thr Glu Asn Tyr Ala Val Thr
            180                 185                 190

Val Lys Ala Ile Asn Val Val Gln Ala Leu Gln Ser Ser Arg Asp Ser
        195                 200                 205

Lys Val Val Asp Ala Phe Lys Ser Pro Arg His Leu Pro Arg Lys Arg
    210                 215                 220

His Thr Ile Cys Ser Asn Ser
225                 230


<210> SEQ ID NO 3
<211> LENGTH: 657
```

-continued

```
<212> TYPE: DNA
<213> ORGANISM: Bacillus thuringiensis
<220> FEATURE:
<221> NAME/KEY: CDS
<222> LOCATION: (1)..(657)
<223> OTHER INFORMATION: TIC810

<400> SEQUENCE: 3

gtg agt aaa gaa att cgt tta aat ttg agt aga gaa tca ggg gca gat       48
Val Ser Lys Glu Ile Arg Leu Asn Leu Ser Arg Glu Ser Gly Ala Asp
1               5                   10                  15

tta tat tta aaa ata ctt gct ttt gta aaa cct gag cat ttt ttt caa       96
Leu Tyr Leu Lys Ile Leu Ala Phe Val Lys Pro Glu His Phe Phe Gln
            20                  25                  30

gca tat tta tta tgt aga gaa ttt gag tct atc gta gat cct aca aca      144
Ala Tyr Leu Leu Cys Arg Glu Phe Glu Ser Ile Val Asp Pro Thr Thr
        35                  40                  45

aga gaa tcg gat ttt gac aaa aca ctt acc att gta aag agt gat tca      192
Arg Glu Ser Asp Phe Asp Lys Thr Leu Thr Ile Val Lys Ser Asp Ser
    50                  55                  60

act tta gtt acg gtt ggt aca atg aat act aaa ctt gtg aat agt caa      240
Thr Leu Val Thr Val Gly Thr Met Asn Thr Lys Leu Val Asn Ser Gln
65                  70                  75                  80

gaa att cta gtt agt gat ttg att acg caa gtt gga agt cag ata gct      288
Glu Ile Leu Val Ser Asp Leu Ile Thr Gln Val Gly Ser Gln Ile Ala
                85                  90                  95

gat acc tta ggt att aca gac att gat gca aat aca cag caa caa tta      336
Asp Thr Leu Gly Ile Thr Asp Ile Asp Ala Asn Thr Gln Gln Gln Leu
            100                 105                 110

aca gaa tta att gga aat tta ttt gtg aat ctg aat tct caa gtt caa      384
Thr Glu Leu Ile Gly Asn Leu Phe Val Asn Leu Asn Ser Gln Val Gln
        115                 120                 125

gaa tat att tat ttt tat gag gaa aaa gaa aag caa aca agt tat cgc      432
Glu Tyr Ile Tyr Phe Tyr Glu Glu Lys Glu Lys Gln Thr Ser Tyr Arg
    130                 135                 140

tat aac atc ctt ttc gtt ttt gaa aaa gag tct ttt atc acc att tta      480
Tyr Asn Ile Leu Phe Val Phe Glu Lys Glu Ser Phe Ile Thr Ile Leu
145                 150                 155                 160

cca atg gga ttc gat gtg act gtg aac act aat aaa gaa gcg gtt ctt      528
Pro Met Gly Phe Asp Val Thr Val Asn Thr Asn Lys Glu Ala Val Leu
                165                 170                 175

aag tta aca cct aaa gat aaa gtc act tat ggt cat gta tca gta aaa      576
Lys Leu Thr Pro Lys Asp Lys Val Thr Tyr Gly His Val Ser Val Lys
            180                 185                 190

gct tta aat att att caa ctt atc aca gaa gat aaa ttt aac ttt ctt      624
Ala Leu Asn Ile Ile Gln Leu Ile Thr Glu Asp Lys Phe Asn Phe Leu
        195                 200                 205

gct aca tta aaa aag gca cta aaa act cta taa                          657
Ala Thr Leu Lys Lys Ala Leu Lys Thr Leu
    210                 215


<210> SEQ ID NO 4
<211> LENGTH: 218
<212> TYPE: PRT
<213> ORGANISM: Bacillus thuringiensis

<400> SEQUENCE: 4

Val Ser Lys Glu Ile Arg Leu Asn Leu Ser Arg Glu Ser Gly Ala Asp
1               5                   10                  15

Leu Tyr Leu Lys Ile Leu Ala Phe Val Lys Pro Glu His Phe Phe Gln
            20                  25                  30
```

```
Ala Tyr Leu Leu Cys Arg Glu Phe Glu Ser Ile Val Asp Pro Thr Thr
        35                  40                  45

Arg Glu Ser Asp Phe Asp Lys Thr Leu Thr Ile Val Lys Ser Asp Ser
    50                  55                  60

Thr Leu Val Thr Val Gly Thr Met Asn Thr Lys Leu Val Asn Ser Gln
65                  70                  75                  80

Glu Ile Leu Val Ser Asp Leu Ile Thr Gln Val Gly Ser Gln Ile Ala
                85                  90                  95

Asp Thr Leu Gly Ile Thr Asp Ile Asp Ala Asn Thr Gln Gln Gln Leu
            100                 105                 110

Thr Glu Leu Ile Gly Asn Leu Phe Val Asn Leu Asn Ser Gln Val Gln
        115                 120                 125

Glu Tyr Ile Tyr Phe Tyr Glu Glu Lys Glu Lys Gln Thr Ser Tyr Arg
    130                 135                 140

Tyr Asn Ile Leu Phe Val Phe Glu Lys Glu Ser Phe Ile Thr Ile Leu
145                 150                 155                 160

Pro Met Gly Phe Asp Val Thr Val Asn Thr Asn Lys Glu Ala Val Leu
                165                 170                 175

Lys Leu Thr Pro Lys Asp Lys Val Thr Tyr Gly His Val Ser Val Lys
            180                 185                 190

Ala Leu Asn Ile Ile Gln Leu Ile Thr Glu Asp Lys Phe Asn Phe Leu
        195                 200                 205

Ala Thr Leu Lys Lys Ala Leu Lys Thr Leu
    210                 215


<210> SEQ ID NO 5
<211> LENGTH: 657
<212> TYPE: DNA
<213> ORGANISM: Bacillus thuringiensis
<220> FEATURE:
<221> NAME/KEY: CDS
<222> LOCATION: (1)..(657)
<223> OTHER INFORMATION: TIC812

<400> SEQUENCE: 5

gtg agt aaa gaa att cgt tta aat ttg agt aga gaa tca ggg gca gat       48
Val Ser Lys Glu Ile Arg Leu Asn Leu Ser Arg Glu Ser Gly Ala Asp
1               5                   10                  15

tta tat tta aaa ata ctt gct ttt gta aaa cct gag cat ttt ttt caa       96
Leu Tyr Leu Lys Ile Leu Ala Phe Val Lys Pro Glu His Phe Phe Gln
            20                  25                  30

gca tat tta tta tgt aga gaa ttt gag tct atc gta gat cct aca aca      144
Ala Tyr Leu Leu Cys Arg Glu Phe Glu Ser Ile Val Asp Pro Thr Thr
        35                  40                  45

aga gaa ttg gat ttt gac aaa acg ctt acc att gta aag agt gat tca      192
Arg Glu Leu Asp Phe Asp Lys Thr Leu Thr Ile Val Lys Ser Asp Ser
    50                  55                  60

act tta gtt acg gtt ggt aca atg aat act aaa ctt gtg aat agt caa      240
Thr Leu Val Thr Val Gly Thr Met Asn Thr Lys Leu Val Asn Ser Gln
65                  70                  75                  80

gaa att cta gtt agt gat ttg att aag caa gtt gga agt cag ata gct      288
Glu Ile Leu Val Ser Asp Leu Ile Lys Gln Val Gly Ser Gln Ile Ala
                85                  90                  95

gat acc tta ggt att aca gac att gat gca aat aca cag caa cga tta      336
Asp Thr Leu Gly Ile Thr Asp Ile Asp Ala Asn Thr Gln Gln Arg Leu
            100                 105                 110

acg gaa tta att gaa aat tta ttt gtg aat ctg aat tct caa gtt caa      384
Thr Glu Leu Ile Glu Asn Leu Phe Val Asn Leu Asn Ser Gln Val Gln
        115                 120                 125
```

```
gac tat att tat ttt tat gag gaa aaa gaa aag caa aca agt tat cgc      432
Asp Tyr Ile Tyr Phe Tyr Glu Glu Lys Glu Lys Gln Thr Ser Tyr Arg
    130                 135                 140

tat aac atc ctt ttc gtt ttt gaa aaa gag tct ttt atc acc att tta      480
Tyr Asn Ile Leu Phe Val Phe Glu Lys Glu Ser Phe Ile Thr Ile Leu
145                 150                 155                 160

cca atg gga ttc gat gtg act gtg aac act aat aaa gaa gcg gtt ctt      528
Pro Met Gly Phe Asp Val Thr Val Asn Thr Asn Lys Glu Ala Val Leu
                165                 170                 175

aag tta aca cct aaa gat aaa gtc act tat ggt cat gta tca gta aaa      576
Lys Leu Thr Pro Lys Asp Lys Val Thr Tyr Gly His Val Ser Val Lys
            180                 185                 190

gct tta aat att att caa ttt atc aca gaa gat aaa ttg aac ttt ctt      624
Ala Leu Asn Ile Ile Gln Phe Ile Thr Glu Asp Lys Leu Asn Phe Leu
        195                 200                 205

gct aca tta aaa aag gca cta aaa act cta taa                          657
Ala Thr Leu Lys Lys Ala Leu Lys Thr Leu
    210                 215


<210> SEQ ID NO 6
<211> LENGTH: 218
<212> TYPE: PRT
<213> ORGANISM: Bacillus thuringiensis

<400> SEQUENCE: 6

Val Ser Lys Glu Ile Arg Leu Asn Leu Ser Arg Glu Ser Gly Ala Asp
1               5                   10                  15

Leu Tyr Leu Lys Ile Leu Ala Phe Val Lys Pro Glu His Phe Phe Gln
            20                  25                  30

Ala Tyr Leu Leu Cys Arg Glu Phe Glu Ser Ile Val Asp Pro Thr Thr
        35                  40                  45

Arg Glu Leu Asp Phe Asp Lys Thr Leu Thr Ile Val Lys Ser Asp Ser
    50                  55                  60

Thr Leu Val Thr Val Gly Thr Met Asn Thr Lys Leu Val Asn Ser Gln
65                  70                  75                  80

Glu Ile Leu Val Ser Asp Leu Ile Lys Gln Val Gly Ser Gln Ile Ala
                85                  90                  95

Asp Thr Leu Gly Ile Thr Asp Ile Asp Ala Asn Thr Gln Gln Arg Leu
            100                 105                 110

Thr Glu Leu Ile Glu Asn Leu Phe Val Asn Leu Asn Ser Gln Val Gln
        115                 120                 125

Asp Tyr Ile Tyr Phe Tyr Glu Glu Lys Glu Lys Gln Thr Ser Tyr Arg
    130                 135                 140

Tyr Asn Ile Leu Phe Val Phe Glu Lys Glu Ser Phe Ile Thr Ile Leu
145                 150                 155                 160

Pro Met Gly Phe Asp Val Thr Val Asn Thr Asn Lys Glu Ala Val Leu
                165                 170                 175

Lys Leu Thr Pro Lys Asp Lys Val Thr Tyr Gly His Val Ser Val Lys
            180                 185                 190

Ala Leu Asn Ile Ile Gln Phe Ile Thr Glu Asp Lys Leu Asn Phe Leu
        195                 200                 205

Ala Thr Leu Lys Lys Ala Leu Lys Thr Leu
    210                 215


<210> SEQ ID NO 7
<211> LENGTH: 696
<212> TYPE: DNA
```

-continued

```
<213> ORGANISM: Bacillus thuringiensis
<220> FEATURE:
<221> NAME/KEY: CDS
<222> LOCATION: (1)..(696)
<223> OTHER INFORMATION: ET29

<400> SEQUENCE: 7

atg ttc ttt aat cgc gtt att aca tta aca gta cca tct tca gat gtg       48
Met Phe Phe Asn Arg Val Ile Thr Leu Thr Val Pro Ser Ser Asp Val
1               5                   10                  15

gtt aat tat agt gaa att tat cag gta gct cca caa tat gtg aat caa       96
Val Asn Tyr Ser Glu Ile Tyr Gln Val Ala Pro Gln Tyr Val Asn Gln
            20                  25                  30

gct ctt acg cta gct aaa tat ttc caa gga gca att gat ggt tca aca      144
Ala Leu Thr Leu Ala Lys Tyr Phe Gln Gly Ala Ile Asp Gly Ser Thr
        35                  40                  45

tta cgt ttt gat ttt gaa aaa gcc tta caa att gca aat gat att cca      192
Leu Arg Phe Asp Phe Glu Lys Ala Leu Gln Ile Ala Asn Asp Ile Pro
    50                  55                  60

cag gca gca gtg gta aac act tta aat caa act gtg cag caa ggt aca      240
Gln Ala Ala Val Val Asn Thr Leu Asn Gln Thr Val Gln Gln Gly Thr
65                  70                  75                  80

gtc caa gta tca gtg atg ata gac aag att gta gac att atg aag aat      288
Val Gln Val Ser Val Met Ile Asp Lys Ile Val Asp Ile Met Lys Asn
                85                  90                  95

gta tta tct att gta att gat aac aaa aag ttt tgg gat cag gta aca      336
Val Leu Ser Ile Val Ile Asp Asn Lys Lys Phe Trp Asp Gln Val Thr
            100                 105                 110

gct gct att aca aat aca ttc aca aat cta aat tcg caa gaa agc gaa      384
Ala Ala Ile Thr Asn Thr Phe Thr Asn Leu Asn Ser Gln Glu Ser Glu
        115                 120                 125

gca tgg att ttt tat tac aaa gaa gat gca cat aaa act agt tac tat      432
Ala Trp Ile Phe Tyr Tyr Lys Glu Asp Ala His Lys Thr Ser Tyr Tyr
    130                 135                 140

tat aat atc tta ttt gct ata cag gat gag gaa aca ggt ggg gta atg      480
Tyr Asn Ile Leu Phe Ala Ile Gln Asp Glu Glu Thr Gly Gly Val Met
145                 150                 155                 160

gcg aca tta ccg att gca ttt gat att agt gta gat att gaa aaa gaa      528
Ala Thr Leu Pro Ile Ala Phe Asp Ile Ser Val Asp Ile Glu Lys Glu
                165                 170                 175

aag gtt cta ttt gtt act atc aag gat act gaa aat tat gcg gtt aca      576
Lys Val Leu Phe Val Thr Ile Lys Asp Thr Glu Asn Tyr Ala Val Thr
            180                 185                 190

gta aaa gct att aat gta gta caa gca ctt caa tct tcc cga gat tca      624
Val Lys Ala Ile Asn Val Val Gln Ala Leu Gln Ser Ser Arg Asp Ser
        195                 200                 205

aaa gtt gta gat gct ttt aaa tcg cca cgt cac tta cct aga aaa aga      672
Lys Val Val Asp Ala Phe Lys Ser Pro Arg His Leu Pro Arg Lys Arg
    210                 215                 220

cat aaa att tgt agt aac tct taa                                      696
His Lys Ile Cys Ser Asn Ser
225                 230


<210> SEQ ID NO 8
<211> LENGTH: 231
<212> TYPE: PRT
<213> ORGANISM: Bacillus thuringiensis

<400> SEQUENCE: 8

Met Phe Phe Asn Arg Val Ile Thr Leu Thr Val Pro Ser Ser Asp Val
1               5                   10                  15
```

```
Val Asn Tyr Ser Glu Ile Tyr Gln Val Ala Pro Gln Tyr Val Asn Gln
            20                  25                  30

Ala Leu Thr Leu Ala Lys Tyr Phe Gln Gly Ala Ile Asp Gly Ser Thr
        35                  40                  45

Leu Arg Phe Asp Phe Glu Lys Ala Leu Gln Ile Ala Asn Asp Ile Pro
    50                  55                  60

Gln Ala Ala Val Val Asn Thr Leu Asn Gln Thr Val Gln Gln Gly Thr
65                  70                  75                  80

Val Gln Val Ser Val Met Ile Asp Lys Ile Val Asp Ile Met Lys Asn
                85                  90                  95

Val Leu Ser Ile Val Ile Asp Asn Lys Lys Phe Trp Asp Gln Val Thr
            100                 105                 110

Ala Ala Ile Thr Asn Thr Phe Thr Asn Leu Asn Ser Gln Glu Ser Glu
        115                 120                 125

Ala Trp Ile Phe Tyr Tyr Lys Glu Asp Ala His Lys Thr Ser Tyr Tyr
    130                 135                 140

Tyr Asn Ile Leu Phe Ala Ile Gln Asp Glu Glu Thr Gly Gly Val Met
145                 150                 155                 160

Ala Thr Leu Pro Ile Ala Phe Asp Ile Ser Val Asp Ile Glu Lys Glu
                165                 170                 175

Lys Val Leu Phe Val Thr Ile Lys Asp Thr Glu Asn Tyr Ala Val Thr
            180                 185                 190

Val Lys Ala Ile Asn Val Val Gln Ala Leu Gln Ser Ser Arg Asp Ser
        195                 200                 205

Lys Val Val Asp Ala Phe Lys Ser Pro Arg His Leu Pro Arg Lys Arg
    210                 215                 220

His Lys Ile Cys Ser Asn Ser
225                 230


<210> SEQ ID NO 9
<211> LENGTH: 1411
<212> TYPE: DNA
<213> ORGANISM: Bacillus thuringiensis
<220> FEATURE:
<221> NAME/KEY: misc_feature
<222> LOCATION: (1)..(1411)
<223> OTHER INFORMATION: TIC810 ORF 1-657; ET29 ORF 716-1411

<400> SEQUENCE: 9

atgagtaaag aaattcgttt aaatttgagt agagaatcag gggcagattt atatttaaaa      60

atacttgctt ttgtaaaacc tgagcatttt tttcaagcat atttattatg tagagaattt     120

gagtctatcg tagatcctac aacaagagaa tcggattttg acaaaacact taccattgta     180

aagagtgatt caactttagt tacggttggt acaatgaata ctaaacttgt gaatagtcaa     240

gaaattctag ttagtgattt gattacgcaa gttggaagtc agatagctga taccttaggt     300

attacagaca ttgatgcaaa tacacagcaa caattaacag aattaattgg aaatttattt     360

gtgaatctga attctcaagt tcaagaatat atttattttt atgaggaaaa agaaaaagcaa    420

acaagttatc gctataacat ccttttcgtt tttgaaaaag agtcttttat caccatttta     480

ccaatgggat tcgatgtgac tgtgaacact aataaagaag cggttcttaa gttaacacct     540

aaagataaag tcacttatgg tcatgtatca gtaaaagctt taaatattat tcaacttatc     600

acagaagata aatttaactt tcttgctaca ttaaaaaagg cactaaaaac tctataagcg     660

ggttaagtag gtaaaataga attaaaatga aacagtatga aaggggtaat tttatatgtt     720

ctttaatcgc gttattacat taacagtacc atcttcagat gtggttaatt atagtgaaat     780
```

```
ttatcaggta gctccacaat atgtgaatca agctcttacg ctagctaaat atttccaagg    840

agcaattgat ggttcaacat tacgttttga ttttgaaaaa gccttacaaa ttgcaaatga    900

tattccacag gcagcagtgg taaacacttt aaatcaaact gtgcagcaag gtacagtcca    960

agtatcagtg atgatagaca agattgtaga cattatgaag aatgtattat ctattgtaat   1020

tgataacaaa aagttttggg atcaggtaac agctgctatt acaaatacat tcacaaatct   1080

aaattcgcaa gaaagcgaag catggatttt ttattacaaa gaagatgcac ataaaactag   1140

ttactattat aatatcttat ttgctataca ggatgaggaa acaggtgggg taatggcgac   1200

attaccgatt gcatttgata ttagtgtaga tattgaaaaa gaaaaggttc tatttgttac   1260

tatcaaggat actgaaaatt atgcggttac agtaaaagct attaatgtag tacaagcact   1320

tcaatcttcc cgagattcaa aagttgtaga tgcttttaaa tcgccacgtc acttacctag   1380

aaaaagacat aaaatttgta gtaactctta a                                  1411
```

```
<210> SEQ ID NO 10
<211> LENGTH: 1411
<212> TYPE: DNA
<213> ORGANISM: Bacillus thuringiensis
<220> FEATURE:
<221> NAME/KEY: misc_feature
<222> LOCATION: (1)..(1411)
<223> OTHER INFORMATION: TIC812 ORF 1-657; ET37 ORF 716-1411

<400> SEQUENCE: 10

atgagtaaag aaattcgttt aaatttgagt agagaatcag gggcagattt atatttaaaa     60

atacttgctt ttgtaaaacc tgagcatttt tttcaagcat atttattatg tagagaattt    120

gagtctatcg tagatcctac aacaagagaa ttggattttg acaaaacgct taccattgta    180

aagagtgatt caactttagt tacggttggt acaatgaata ctaaacttgt gaatagtcaa    240

gaaattctag ttagtgattt gattaagcaa gttggaagtc agatagctga taccttaggt    300

attacagaca ttgatgcaaa tacacagcaa cgattaacgg aattaattga aaatttattt    360

gtgaatctga attctcaagt tcaagactat atttattttt atgaggaaaa agaaaagcaa    420

acaagttatc gctataacat ccttttcgtt tttgaaaaag agtcttttat caccatttta    480

ccaatgggat tcgatgtgac tgtgaacact aataaagaag cggttcttaa gttaacacct    540

aaagataaag tcacttatgg tcatgtatca gtaaaagctt taaatattat tcaatttatc    600

acagaagata aattgaactt tcttgctaca ttaaaaaagg cactaaaaac tctataagtg    660

ggttaagtag gtaaaataga attaaaatga aacagtatga aaggggtaat tttatatgtt    720

ctttaatcgc gttattacat taacagtacc atcttcagat gtggttaatt atagtgaaat    780

ttatcaggta gctccacaat atgtgaatca agctcttacg ctagctaaat atttccaagg    840

agcaattgat ggttcaacat tacgttttga ttttgaaaaa gccttacaaa ttgcaaatga    900

tattccacag gcagcagtgg taaacacttt aaatcaaact gtgcagcaag gtacagtcca    960

agtatcagtg atgatagaca agattgtaga cattatgaag aatgtattat ctattgtaat   1020

tgataacaaa aagttttggg atcaggtaac agctgctatt acaaatacat tcacaaatct   1080

aaattcgcaa gaaagcgaag catggatttt ttattacaaa gaagatgcac ataaaactag   1140

ttactattat aatatcttat ttgctataca ggatgaggaa acaggtgggg taatggcgac   1200

attaccgatt gcatttgata ttagtgtaga tattgaaaaa gaaaaggttc tatttgttac   1260

tatcaaggat actgaaaatt atgctgttac agtaaaagct attaatgtag tacaagcact   1320
```

-continued

```
tcaatcttcc cgagattcaa aagttgtaga tgcttttaaa tcgccacgtc acttacctag   1380

aaaaagacat acaatttgta gtaactctta a                                  1411


<210> SEQ ID NO 11
<211> LENGTH: 1531
<212> TYPE: DNA
<213> ORGANISM: Artificial Sequence
<220> FEATURE:
<223> OTHER INFORMATION: ORF TIC810 1-657; ORF ET37 716 - 1411
<220> FEATURE:
<221> NAME/KEY: misc_feature
<222> LOCATION: (1)..(1531)
<223> OTHER INFORMATION: TIC810 ORF 1-657; ET37 ORF 716-1411

<400> SEQUENCE: 11

gaattcgccc ttgcctaggt atgagtaaag aaattcgttt aaatttgagt agagaatcag     60

gggcagattt atatttaaaa atacttgctt ttgtaaaacc tgagcatttt tttcaagcat    120

atttattatg tagagaattt gagtctatcg tagatcctac aacaagagaa tcggattttg    180

acaaaacact taccattgta aagagtgatt caactttagt tacggttggt acaatgaata    240

ctaaacttgt gaatagtcaa gaaattctag ttagtgattt gattacgcaa gttggaagtc    300

agatagctga taccttaggt attacagaca ttgatgcaaa tacacagcaa caattaacag    360

aattaattgg aaatttattt gtgaatctga attctcaagt tcaagaatat atttattttt    420

atgaggaaaa agaaaagcaa acaagttatc gctataacat ccttttcgtt tttgaaaaag    480

agtcttttat caccatttta ccaatgggat tcgatgtgac tgtgaacact aataaagaag    540

cggttcttaa gttaacacct aaagataaag tcacttatgg tcatgtatca gtaaaagctt    600

taaatattat tcaacttatc acagaagata aatttaactt tcttgctaca ttaaaaaagg    660

cactaaaaac tctataagcg ggttaagtag gtaaaataga attaaaatga aacagtatga    720

aaggggtaat tttatatgtt ctttaatcgc gttattacat taacagtacc atcttcagat    780

gtggttaatt atagtgaaat ttatcaggta gctccacaat atgtgaatca agctcttacg    840

ctagctaaat atttccaagg agcaattgat ggttcaacat tacgttttga ttttgaaaaa    900

gccttacaaa ttgcaaatga tattccacag gcagcagtgg taaacacttt aaatcaaact    960

gtgcagcaag gtacagtcca agtatcagtg atgatagaca agattgtaga cattatgaag   1020

aatgtattat ctattgtaat tgataacaaa aagttttggg atcaggtaac agctgctatt   1080

acaaatacat tcacaaatct aaattcgcaa gaaagcgaag catggatttt ttattacaaa   1140

gaagatgcac ataaaactag ttactattat aatatcttat ttgctataca ggatgaggaa   1200

acaggtgggg taatggcgac attaccgatt gcatttgata ttagtgtaga tattgaaaaa   1260

gaaaaggttc tatttgttac tatcaaggat actgaaaatt atgctgttac agtaaaagct   1320

attaatgtag tacaagcact tcaatcttcc cgagattcaa aagttgtaga tgcttttaaa   1380

tcgccacgtc acttacctag aaaaagacat acaatttgta gtaactctta agaagaccga   1440

caataagata aaatcttatt gcctatcttc ttagaataac aaatggctgt tatggggaag   1500

cactaaatgg actcgagtta agggcgaatt c                                  1531


<210> SEQ ID NO 12
<211> LENGTH: 1531
<212> TYPE: DNA
<213> ORGANISM: Artificial Sequence
<220> FEATURE:
<223> OTHER INFORMATION: ORF TIC812 1-657; ORF ET29 716-1411
<220> FEATURE:
<221> NAME/KEY: misc_feature
```

-continued

```
<222> LOCATION: (1)..(1531)
<223> OTHER INFORMATION: TIC812 ORF 1-657; ET29 ORF 716-1411

<400> SEQUENCE: 12

gaattcgccc ttgcctaggt atgagtaaag aaattcgttt aaatttgagt agagaatcag     60

gggcagattt atatttaaaa atacttgctt ttgtaaaacc tgagcatttt tttcaagcat    120

atttattatg tagagaattt gagtctatcg tagatcctac aacaagagaa ttggattttg    180

acaaaacgct taccattgta aagagtgatt caactttagt tacggttggt acaatgaata    240

ctaaacttgt gaatagtcaa gaaattctag ttagtgattt gattaagcaa gttggaagtc    300

agatagctga taccttaggt attacagaca ttgatgcaaa tacacagcaa cgattaacgg    360

aattaattga aaatttattt gtgaatctga attctcaagt tcaagactat atttattttt    420

atgaggaaaa agaaaagcaa acaagttatc gctataacat ccttttcgtt tttgaaaaag    480

agtcttttat caccatttta ccaatgggat tcgatgtgac tgtgaacact aataaagaag    540

cggttcttaa gttaacacct aaagataaag tcacttatgg tcatgtatca gtaaaagctt    600

taaatattat tcaatttatc acagaagata aattgaactt tcttgctaca ttaaaaaagg    660

cactaaaaac tctataagtg ggttaagtag gtaaaataga attaaaatga aacagtatga    720

aaggggtaat tttatatgtt ctttaatcgc gttattacat taacagtacc atcttcagat    780

gtggttaatt atagtgaaat ttatcaggta gctccacaat atgtgaatca agctcttacg    840

ctagctaaat atttccaagg agcaattgat ggttcaacat tacgttttga ttttgaaaaa    900

gccttacaaa ttgcaaatga tattccacag gcagcagtgg taaacacttt aaatcaaact    960

gtgcagcaag gtacagtcca agtatcagtg atgatagaca agattgtaga cattatgaag   1020

aatgtattat ctattgtaat tgataacaaa aagttttggg atcaggtaac agctgctatt   1080

acaaatacat tcacaaatct aaattcgcaa gaaagcgaag catggatttt ttattacaaa   1140

gaagatgcac ataaaactag ttactattat aatatcttat ttgctataca ggatgaggaa   1200

acaggtgggg taatggcgac attaccgatt gcatttgata ttagtgtaga tattgaaaaa   1260

gaaaaggttc tatttgttac tatcaaggat actgaaaatt atgcggttac agtaaaagct   1320

attaatgtag tacaagcact tcaatcttcc cgagattcaa aagttgtaga tgcttttaaa   1380

tcgccacgtc acttacctag aaaaagacat aaaatttgta gtaactctta agaagaccga   1440

caataagata aaatcttatt gtctatcttc ttagaataac aaatggctgt tatggggaag   1500

cactaaatgg actcgagtta agggcgaatt c                                   1531


<210> SEQ ID NO 13
<211> LENGTH: 702
<212> TYPE: DNA
<213> ORGANISM: Artificial Sequence
<220> FEATURE:
<223> OTHER INFORMATION: synthetic sequence for use in expressing TIC809
      (ET29 MET-ALA) in planta
<220> FEATURE:
<221> NAME/KEY: CDS
<222> LOCATION: (1)..(702)
<223> OTHER INFORMATION: TIC809

<400> SEQUENCE: 13

atg gcc ttc ttc aac cgg gtg atc acc ctc acg gtg ccg tcg tca gac       48
Met Ala Phe Phe Asn Arg Val Ile Thr Leu Thr Val Pro Ser Ser Asp
1               5                   10                  15

gtg gtc aac tac tcg gag atc tac cag gtg gct cct cag tat gtc aac       96
Val Val Asn Tyr Ser Glu Ile Tyr Gln Val Ala Pro Gln Tyr Val Asn
            20                  25                  30
```

```
cag gcc ctg acc ctg gcc aag tac ttc cag ggc gcc atc gac ggc agc      144
Gln Ala Leu Thr Leu Ala Lys Tyr Phe Gln Gly Ala Ile Asp Gly Ser
        35                  40                  45

acc ctg agg ttc gac ttc gag aag gcg tta cag atc gcc aac gac atc      192
Thr Leu Arg Phe Asp Phe Glu Lys Ala Leu Gln Ile Ala Asn Asp Ile
    50                  55                  60

ccg cag gcc gcg gtg gtc aac acc ctg aac cag acc gtc cag cag ggg      240
Pro Gln Ala Ala Val Val Asn Thr Leu Asn Gln Thr Val Gln Gln Gly
65                  70                  75                  80

acc gtc cag gtc agc gtc atg atc gac aag atc gtg gac atc atg aag      288
Thr Val Gln Val Ser Val Met Ile Asp Lys Ile Val Asp Ile Met Lys
                85                  90                  95

aat gtc ctg tcc atc gtg ata gac aac aag aag ttt tgg gat cag gtc      336
Asn Val Leu Ser Ile Val Ile Asp Asn Lys Lys Phe Trp Asp Gln Val
            100                 105                 110

acg gct gcc atc acc aac acc ttc acg aac ctg aac agc cag gag tcg      384
Thr Ala Ala Ile Thr Asn Thr Phe Thr Asn Leu Asn Ser Gln Glu Ser
        115                 120                 125

gag gcc tgg atc ttc tat tac aag gag gac gcc cac aag acg tcc tac      432
Glu Ala Trp Ile Phe Tyr Tyr Lys Glu Asp Ala His Lys Thr Ser Tyr
    130                 135                 140

tat tac aac atc ctc ttc gcc atc cag gac gaa gag acg ggt ggc gtg      480
Tyr Tyr Asn Ile Leu Phe Ala Ile Gln Asp Glu Glu Thr Gly Gly Val
145                 150                 155                 160

atg gcc acg ctg ccc atc gcc ttc gac atc agt gtg gac atc gag aag      528
Met Ala Thr Leu Pro Ile Ala Phe Asp Ile Ser Val Asp Ile Glu Lys
                165                 170                 175

gag aag gtc ctg ttc gtg acc atc aag gac act gag aat tac gcc gtc      576
Glu Lys Val Leu Phe Val Thr Ile Lys Asp Thr Glu Asn Tyr Ala Val
            180                 185                 190

acc gtc aag gcg atc aac gtg gtc cag gca ctc cag tct agc agg gat      624
Thr Val Lys Ala Ile Asn Val Val Gln Ala Leu Gln Ser Ser Arg Asp
        195                 200                 205

tct aag gtg gtt gat gcg ttc aaa tcg cca cgg cac tta ccc cgg aag      672
Ser Lys Val Val Asp Ala Phe Lys Ser Pro Arg His Leu Pro Arg Lys
    210                 215                 220

agg cat aag att tgc tct aac tcg tga tga                              702
Arg His Lys Ile Cys Ser Asn Ser
225                 230


<210> SEQ ID NO 14
<211> LENGTH: 232
<212> TYPE: PRT
<213> ORGANISM: Artificial Sequence
<220> FEATURE:
<223> OTHER INFORMATION: Synthetic Construct

<400> SEQUENCE: 14

Met Ala Phe Phe Asn Arg Val Ile Thr Leu Thr Val Pro Ser Ser Asp
1               5                   10                  15

Val Val Asn Tyr Ser Glu Ile Tyr Gln Val Ala Pro Gln Tyr Val Asn
            20                  25                  30

Gln Ala Leu Thr Leu Ala Lys Tyr Phe Gln Gly Ala Ile Asp Gly Ser
        35                  40                  45

Thr Leu Arg Phe Asp Phe Glu Lys Ala Leu Gln Ile Ala Asn Asp Ile
    50                  55                  60

Pro Gln Ala Ala Val Val Asn Thr Leu Asn Gln Thr Val Gln Gln Gly
65                  70                  75                  80

Thr Val Gln Val Ser Val Met Ile Asp Lys Ile Val Asp Ile Met Lys
```

-continued

```
                85                  90                  95

Asn Val Leu Ser Ile Val Ile Asp Asn Lys Lys Phe Trp Asp Gln Val
            100                 105                 110

Thr Ala Ala Ile Thr Asn Thr Phe Thr Asn Leu Asn Ser Gln Glu Ser
        115                 120                 125

Glu Ala Trp Ile Phe Tyr Tyr Lys Glu Asp Ala His Lys Thr Ser Tyr
    130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
            180                 185                 190

Thr Val Lys Ala Ile Asn Val Val Gln Ala Leu Gln Ser Ser Arg Asp
        195                 200                 205

Ser Lys Val Val Asp Ala Phe Lys Ser Pro Arg His Leu Pro Arg Lys
    210                 215                 220

Arg His Lys Ile Cys Ser Asn Ser
225                 230


<210> SEQ ID NO 15
<211> LENGTH: 666
<212> TYPE: DNA
<213> ORGANISM: Artificial Sequence
<220> FEATURE:
<223> OTHER INFORMATION: synthetic sequence for use in expression of
      TIC810 in planta
<220> FEATURE:
<221> NAME/KEY: CDS
<222> LOCATION: (1)..(666)
<223> OTHER INFORMATION: TIC810

<400> SEQUENCE: 15

atg agc aaa gaa atc agg ctc aac ctt tct cgt gag agc ggc gcc gac       48
Met Ser Lys Glu Ile Arg Leu Asn Leu Ser Arg Glu Ser Gly Ala Asp
1               5                   10                  15

ctg tac ctc aag atc ctc gcc ttc gtg aag ccc gag cac ttc ttt cag       96
Leu Tyr Leu Lys Ile Leu Ala Phe Val Lys Pro Glu His Phe Phe Gln
            20                  25                  30

gcg tac ctc ctg tgc cgc gag ttc gag agc atc gtg gat cct aca acc      144
Ala Tyr Leu Leu Cys Arg Glu Phe Glu Ser Ile Val Asp Pro Thr Thr
        35                  40                  45

cgc gag tct gac ttc gac aag acg ctg acc atc gtg aag tcg gac tcc      192
Arg Glu Ser Asp Phe Asp Lys Thr Leu Thr Ile Val Lys Ser Asp Ser
    50                  55                  60

acc ctc gtg acc gtg ggc acg atg aac acc aag ctg gtc aat agc caa      240
Thr Leu Val Thr Val Gly Thr Met Asn Thr Lys Leu Val Asn Ser Gln
65                  70                  75                  80

gag atc ctc gtg tcg gac ttg atc act caa gtc ggt tcc cag atc gcc      288
Glu Ile Leu Val Ser Asp Leu Ile Thr Gln Val Gly Ser Gln Ile Ala
                85                  90                  95

gat acc ctc ggc atc acg gac atc gac gcc aac acc cag caa cag ctc      336
Asp Thr Leu Gly Ile Thr Asp Ile Asp Ala Asn Thr Gln Gln Gln Leu
            100                 105                 110

acg gag ctg atc ggc aac ctc ttc gtg aac ctc aat tcc caa gtt cag      384
Thr Glu Leu Ile Gly Asn Leu Phe Val Asn Leu Asn Ser Gln Val Gln
        115                 120                 125

gag tac atc tac ttc tac gag gag aag gag aag cag acc tcc tac cgc      432
Glu Tyr Ile Tyr Phe Tyr Glu Glu Lys Glu Lys Gln Thr Ser Tyr Arg
    130                 135                 140
```

```
tac aac atc ctc ttc gtg ttc gaa aag gag tcg ttc atc acc att ctg      480
Tyr Asn Ile Leu Phe Val Phe Glu Lys Glu Ser Phe Ile Thr Ile Leu
145                 150                 155                 160

cca atg ggc ttc gac gtg acc gtg aac acg aac aag gag gcc gtc ctg      528
Pro Met Gly Phe Asp Val Thr Val Asn Thr Asn Lys Glu Ala Val Leu
                165                 170                 175

aag ctg acc ccg aag gac aag gtt acc tac ggc cac gtc agc gtc aag      576
Lys Leu Thr Pro Lys Asp Lys Val Thr Tyr Gly His Val Ser Val Lys
            180                 185                 190

gcc ctc aac atc atc cag ctc att acg gag gac aag ttc aac ttc ctc      624
Ala Leu Asn Ile Ile Gln Leu Ile Thr Glu Asp Lys Phe Asn Phe Leu
        195                 200                 205

gca acc ctc aag aag gct ctc aag acc ctg tga tga gaa ttc              666
Ala Thr Leu Lys Lys Ala Leu Lys Thr Leu         Glu Phe
    210                 215                         220


<210> SEQ ID NO 16
<211> LENGTH: 218
<212> TYPE: PRT
<213> ORGANISM: Artificial Sequence
<220> FEATURE:
<223> OTHER INFORMATION: Synthetic Construct

<400> SEQUENCE: 16

Met Ser Lys Glu Ile Arg Leu Asn Leu Ser Arg Glu Ser Gly Ala Asp
1               5                   10                  15

Leu Tyr Leu Lys Ile Leu Ala Phe Val Lys Pro Glu His Phe Phe Gln
            20                  25                  30

Ala Tyr Leu Leu Cys Arg Glu Phe Glu Ser Ile Val Asp Pro Thr Thr
        35                  40                  45

Arg Glu Ser Asp Phe Asp Lys Thr Leu Thr Ile Val Lys Ser Asp Ser
    50                  55                  60

Thr Leu Val Thr Val Gly Thr Met Asn Thr Lys Leu Val Asn Ser Gln
65                  70                  75                  80

Glu Ile Leu Val Ser Asp Leu Ile Thr Gln Val Gly Ser Gln Ile Ala
                85                  90                  95

Asp Thr Leu Gly Ile Thr Asp Ile Asp Ala Asn Thr Gln Gln Gln Leu
            100                 105                 110

Thr Glu Leu Ile Gly Asn Leu Phe Val Asn Leu Asn Ser Gln Val Gln
        115                 120                 125

Glu Tyr Ile Tyr Phe Tyr Glu Glu Lys Glu Lys Gln Thr Ser Tyr Arg
    130                 135                 140

Tyr Asn Ile Leu Phe Val Phe Glu Lys Glu Ser Phe Ile Thr Ile Leu
145                 150                 155                 160

Pro Met Gly Phe Asp Val Thr Val Asn Thr Asn Lys Glu Ala Val Leu
                165                 170                 175

Lys Leu Thr Pro Lys Asp Lys Val Thr Tyr Gly His Val Ser Val Lys
            180                 185                 190

Ala Leu Asn Ile Ile Gln Leu Ile Thr Glu Asp Lys Phe Asn Phe Leu
        195                 200                 205

Ala Thr Leu Lys Lys Ala Leu Lys Thr Leu
    210                 215


<210> SEQ ID NO 17
<211> LENGTH: 699
<212> TYPE: DNA
<213> ORGANISM: Artificial Sequence
<220> FEATURE:
```

```
<223> OTHER INFORMATION: synthetic sequence for expression of ET37 in
      planta
<220> FEATURE:
<221> NAME/KEY: CDS
<222> LOCATION: (1)..(699)
<223> OTHER INFORMATION: ET37

<400> SEQUENCE: 17

atg ttc ttc aac cgg gtg atc acc ctc acg gtg ccg tcg tca gac gtg       48
Met Phe Phe Asn Arg Val Ile Thr Leu Thr Val Pro Ser Ser Asp Val
1               5                   10                  15

gtc aac tac tcg gag atc tac cag gtg gct cct cag tat gtc aac cag       96
Val Asn Tyr Ser Glu Ile Tyr Gln Val Ala Pro Gln Tyr Val Asn Gln
            20                  25                  30

gcc ctg acc ctg gcc aag tac ttc cag ggc gcc atc gac ggc agc acc      144
Ala Leu Thr Leu Ala Lys Tyr Phe Gln Gly Ala Ile Asp Gly Ser Thr
        35                  40                  45

ctg agg ttc gac ttc gag aag gcg tta cag atc gcc aac gac atc ccg      192
Leu Arg Phe Asp Phe Glu Lys Ala Leu Gln Ile Ala Asn Asp Ile Pro
    50                  55                  60

cag gcc gcg gtg gtc aac acc ctg aac cag acc gtc cag cag ggg acc      240
Gln Ala Ala Val Val Asn Thr Leu Asn Gln Thr Val Gln Gln Gly Thr
65                  70                  75                  80

gtc cag gtc agc gtc atg atc gac aag atc gtg gac atc atg aag aat      288
Val Gln Val Ser Val Met Ile Asp Lys Ile Val Asp Ile Met Lys Asn
                85                  90                  95

gtc ctg tcc atc gtg ata gac aac aag aag ttt tgg gat cag gtc acg      336
Val Leu Ser Ile Val Ile Asp Asn Lys Lys Phe Trp Asp Gln Val Thr
            100                 105                 110

gct gcc atc acc aac acc ttc acg aac ctg aac agc cag gag tcg gag      384
Ala Ala Ile Thr Asn Thr Phe Thr Asn Leu Asn Ser Gln Glu Ser Glu
        115                 120                 125

gcc tgg atc ttc tat tac aag gag gac gcc cac aag acg tcc tac tat      432
Ala Trp Ile Phe Tyr Tyr Lys Glu Asp Ala His Lys Thr Ser Tyr Tyr
    130                 135                 140

tac aac atc ctc ttc gcc atc cag gac gaa gag acg ggt ggc gtg atg      480
Tyr Asn Ile Leu Phe Ala Ile Gln Asp Glu Glu Thr Gly Gly Val Met
145                 150                 155                 160

gcc acg ctg ccc atc gcc ttc gac atc agt gtg gac atc gag aag gag      528
Ala Thr Leu Pro Ile Ala Phe Asp Ile Ser Val Asp Ile Glu Lys Glu
                165                 170                 175

aag gtc ctg ttc gtg acc atc aag gac act gag aat tac gcc gtc acc      576
Lys Val Leu Phe Val Thr Ile Lys Asp Thr Glu Asn Tyr Ala Val Thr
            180                 185                 190

gtc aag gcg atc aac gtg gtc cag gca ctc cag tct agc agg gat tct      624
Val Lys Ala Ile Asn Val Val Gln Ala Leu Gln Ser Ser Arg Asp Ser
        195                 200                 205

aag gtg gtt gat gcg ttc aaa tcg cca cgg cac tta ccc cgg aag agg      672
Lys Val Val Asp Ala Phe Lys Ser Pro Arg His Leu Pro Arg Lys Arg
    210                 215                 220

cat acc att tgc tct aac tcg tga tga                                  699
His Thr Ile Cys Ser Asn Ser
225                 230


<210> SEQ ID NO 18
<211> LENGTH: 231
<212> TYPE: PRT
<213> ORGANISM: Artificial Sequence
<220> FEATURE:
<223> OTHER INFORMATION: Synthetic Construct

<400> SEQUENCE: 18
```

```
Met Phe Phe Asn Arg Val Ile Thr Leu Thr Val Pro Ser Ser Asp Val
1               5                   10                  15

Val Asn Tyr Ser Glu Ile Tyr Gln Val Ala Pro Gln Tyr Val Asn Gln
            20                  25                  30

Ala Leu Thr Leu Ala Lys Tyr Phe Gln Gly Ala Ile Asp Gly Ser Thr
        35                  40                  45

Leu Arg Phe Asp Phe Glu Lys Ala Leu Gln Ile Ala Asn Asp Ile Pro
    50                  55                  60

Gln Ala Ala Val Val Asn Thr Leu Asn Gln Thr Val Gln Gln Gly Thr
65                  70                  75                  80

Val Gln Val Ser Val Met Ile Asp Lys Ile Val Asp Ile Met Lys Asn
                85                  90                  95

Val Leu Ser Ile Val Ile Asp Asn Lys Lys Phe Trp Asp Gln Val Thr
            100                 105                 110

Ala Ala Ile Thr Asn Thr Phe Thr Asn Leu Asn Ser Gln Glu Ser Glu
        115                 120                 125

Ala Trp Ile Phe Tyr Tyr Lys Glu Asp Ala His Lys Thr Ser Tyr Tyr
    130                 135                 140

Tyr Asn Ile Leu Phe Ala Ile Gln Asp Glu Glu Thr Gly Gly Val Met
145                 150                 155                 160

Ala Thr Leu Pro Ile Ala Phe Asp Ile Ser Val Asp Ile Glu Lys Glu
                165                 170                 175

Lys Val Leu Phe Val Thr Ile Lys Asp Thr Glu Asn Tyr Ala Val Thr
            180                 185                 190

Val Lys Ala Ile Asn Val Val Gln Ala Leu Gln Ser Ser Arg Asp Ser
        195                 200                 205

Lys Val Val Asp Ala Phe Lys Ser Pro Arg His Leu Pro Arg Lys Arg
    210                 215                 220

His Thr Ile Cys Ser Asn Ser
225                 230


<210> SEQ ID NO 19
<211> LENGTH: 657
<212> TYPE: DNA
<213> ORGANISM: Artificial Sequence
<220> FEATURE:
<223> OTHER INFORMATION: synthetic sequence for expression of TIC812 in
      planta
<220> FEATURE:
<221> NAME/KEY: CDS
<222> LOCATION: (1)..(657)
<223> OTHER INFORMATION: TIC812

<400> SEQUENCE: 19

atg agc aaa gaa atc agg ctc aac ctt tct cgt gag agc ggc gcc gac       48
Met Ser Lys Glu Ile Arg Leu Asn Leu Ser Arg Glu Ser Gly Ala Asp
1               5                   10                  15

ctg tac ctc aag atc ctc gcc ttc gtg aag ccc gag cac ttc ttt cag       96
Leu Tyr Leu Lys Ile Leu Ala Phe Val Lys Pro Glu His Phe Phe Gln
            20                  25                  30

gcg tac ctc ctg tgc cgc gag ttc gag agc atc gtg gat cct aca acc      144
Ala Tyr Leu Leu Cys Arg Glu Phe Glu Ser Ile Val Asp Pro Thr Thr
        35                  40                  45

cgc gag ctg gac ttc gac aag acg ctg acc atc gtg aag tcg gac tcc      192
Arg Glu Leu Asp Phe Asp Lys Thr Leu Thr Ile Val Lys Ser Asp Ser
    50                  55                  60

acc ctc gtg acc gtg ggc acg atg aac acc aag ctg gtc aat agc caa      240
Thr Leu Val Thr Val Gly Thr Met Asn Thr Lys Leu Val Asn Ser Gln
65                  70                  75                  80
```

-continued

```
gag atc ctc gtg tcg gac ttg atc aag caa gtc ggt tcc cag atc gcc      288
Glu Ile Leu Val Ser Asp Leu Ile Lys Gln Val Gly Ser Gln Ile Ala
                85                  90                  95

gat acc ctc ggc atc acg gac atc gac gcc aac acc cag caa agg ctc      336
Asp Thr Leu Gly Ile Thr Asp Ile Asp Ala Asn Thr Gln Gln Arg Leu
            100                 105                 110

acg gag ctg atc gag aac ctc ttc gtg aac ctc aat tcc caa gtt cag      384
Thr Glu Leu Ile Glu Asn Leu Phe Val Asn Leu Asn Ser Gln Val Gln
        115                 120                 125

gac tac atc tac ttc tac gag gag aag gag aag cag acc tcc tac cgc      432
Asp Tyr Ile Tyr Phe Tyr Glu Glu Lys Glu Lys Gln Thr Ser Tyr Arg
    130                 135                 140

tac aac atc ctc ttc gtg ttc gaa aag gag tcg ttc atc acc att ctg      480
Tyr Asn Ile Leu Phe Val Phe Glu Lys Glu Ser Phe Ile Thr Ile Leu
145                 150                 155                 160

cca atg ggc ttc gac gtg acc gtg aac acg aac aag gag gcc gtc ctg      528
Pro Met Gly Phe Asp Val Thr Val Asn Thr Asn Lys Glu Ala Val Leu
                165                 170                 175

aag ctg acc ccg aag gac aag gtt acc tac ggc cac gtc agc gtc aag      576
Lys Leu Thr Pro Lys Asp Lys Val Thr Tyr Gly His Val Ser Val Lys
            180                 185                 190

gcc ctc aac atc atc cag ttc att acg gag gac aag ctc aac ttc ctc      624
Ala Leu Asn Ile Ile Gln Phe Ile Thr Glu Asp Lys Leu Asn Phe Leu
        195                 200                 205

gca acc ctc aag aag gct ctc aag acc ctg tga                          657
Ala Thr Leu Lys Lys Ala Leu Lys Thr Leu
    210                 215


<210> SEQ ID NO 20
<211> LENGTH: 218
<212> TYPE: PRT
<213> ORGANISM: Artificial Sequence
<220> FEATURE:
<223> OTHER INFORMATION: Synthetic Construct

<400> SEQUENCE: 20

Met Ser Lys Glu Ile Arg Leu Asn Leu Ser Arg Glu Ser Gly Ala Asp
1               5                   10                  15

Leu Tyr Leu Lys Ile Leu Ala Phe Val Lys Pro Glu His Phe Phe Gln
            20                  25                  30

Ala Tyr Leu Leu Cys Arg Glu Phe Glu Ser Ile Val Asp Pro Thr Thr
        35                  40                  45

Arg Glu Leu Asp Phe Asp Lys Thr Leu Thr Ile Val Lys Ser Asp Ser
    50                  55                  60

Thr Leu Val Thr Val Gly Thr Met Asn Thr Lys Leu Val Asn Ser Gln
65                  70                  75                  80

Glu Ile Leu Val Ser Asp Leu Ile Lys Gln Val Gly Ser Gln Ile Ala
                85                  90                  95

Asp Thr Leu Gly Ile Thr Asp Ile Asp Ala Asn Thr Gln Gln Arg Leu
            100                 105                 110

Thr Glu Leu Ile Glu Asn Leu Phe Val Asn Leu Asn Ser Gln Val Gln
        115                 120                 125

Asp Tyr Ile Tyr Phe Tyr Glu Glu Lys Glu Lys Gln Thr Ser Tyr Arg
    130                 135                 140

Tyr Asn Ile Leu Phe Val Phe Glu Lys Glu Ser Phe Ile Thr Ile Leu
145                 150                 155                 160

Pro Met Gly Phe Asp Val Thr Val Asn Thr Asn Lys Glu Ala Val Leu
                165                 170                 175
```

-continued

```
Lys Leu Thr Pro Lys Asp Lys Val Thr Tyr Gly His Val Ser Val Lys
            180                 185                 190

Ala Leu Asn Ile Ile Gln Phe Ile Thr Glu Asp Lys Leu Asn Phe Leu
        195                 200                 205

Ala Thr Leu Lys Lys Ala Leu Lys Thr Leu
    210                 215


<210> SEQ ID NO 21
<211> LENGTH: 22
<212> TYPE: DNA
<213> ORGANISM: Artificial Sequence
<220> FEATURE:
<223> OTHER INFORMATION: synthetic sequence; thermal amplification
      primer
<220> FEATURE:
<221> NAME/KEY: misc_feature
<222> LOCATION: (1)..(22)
<223> OTHER INFORMATION: thermal amplification primer; pr370

<400> SEQUENCE: 21

cctacttaac ccgcttatag ag                                              22


<210> SEQ ID NO 22
<211> LENGTH: 21
<212> TYPE: DNA
<213> ORGANISM: Artificial Sequence
<220> FEATURE:
<223> OTHER INFORMATION: synthetic sequence; thermal amplification
      primer
<220> FEATURE:
<221> NAME/KEY: misc_feature
<222> LOCATION: (1)..(21)
<223> OTHER INFORMATION: thermal amplification primer; pr371

<400> SEQUENCE: 22

cagtaccatc ttcagatgtg g                                               21


<210> SEQ ID NO 23
<211> LENGTH: 49
<212> TYPE: DNA
<213> ORGANISM: Artificial Sequence
<220> FEATURE:
<223> OTHER INFORMATION: synthetic sequence; thermal amplification
      primer
<220> FEATURE:
<221> NAME/KEY: misc_feature
<222> LOCATION: (1)..(49)
<223> OTHER INFORMATION: thermal amplification primer; pr375

<400> SEQUENCE: 23

gactagtaat gagtaaagaa attcgtttaa atttgagtag agaatcagg                 49


<210> SEQ ID NO 24
<211> LENGTH: 30
<212> TYPE: DNA
<213> ORGANISM: Artificial Sequence
<220> FEATURE:
<223> OTHER INFORMATION: synthetic sequence; thermal amplification
      primer
<220> FEATURE:
<221> NAME/KEY: misc_feature
<222> LOCATION: (1)..(30)
<223> OTHER INFORMATION: thermal amplification primer; pr376

<400> SEQUENCE: 24

aactcgagcc tacttaaccc gcttatagag                                      30
```

<210> SEQ ID NO 25
<211> LENGTH: 35
<212> TYPE: DNA
<213> ORGANISM: Artificial Sequence
<220> FEATURE:
<223> OTHER INFORMATION: synthetic sequence; thermal amplification primer
<220> FEATURE:
<221> NAME/KEY: misc_feature
<222> LOCATION: (1)..(35)
<223> OTHER INFORMATION: thermal amplification primer; pr365

<400> SEQUENCE: 25
aactcgagtc catttagtgc ttccccataa cagcc 35

<210> SEQ ID NO 26
<211> LENGTH: 43
<212> TYPE: DNA
<213> ORGANISM: Artificial Sequence
<220> FEATURE:
<223> OTHER INFORMATION: synthetic sequence; thermal amplification primer
<220> FEATURE:
<221> NAME/KEY: misc_feature
<222> LOCATION: (1)..(43)
<223> OTHER INFORMATION: thermal amplification primer; pr372

<400> SEQUENCE: 26
aacctaggat gttctttaat cgcgttatta cattaacagt acc 43

<210> SEQ ID NO 27
<211> LENGTH: 49
<212> TYPE: DNA
<213> ORGANISM: Artificial Sequence
<220> FEATURE:
<223> OTHER INFORMATION: synthetic sequence; thermal amplification primer
<220> FEATURE:
<221> NAME/KEY: misc_feature
<222> LOCATION: (1)..(49)
<223> OTHER INFORMATION: thermal amplification primer; pr421

<400> SEQUENCE: 27
gcctaggtat gagtaaagaa attcgtttaa atttgagtag agaatcagg 49

<210> SEQ ID NO 28
<211> LENGTH: 4257
<212> TYPE: DNA
<213> ORGANISM: Artificial Sequence
<220> FEATURE:
<223> OTHER INFORMATION: synthetic sequence; pMON64138 expression cassettes encoding TIC89 and TIC810
<220> FEATURE:
<221> NAME/KEY: misc_feature
<223> OTHER INFORMATION: pMON64138 first and second plant expression cassettes
<220> FEATURE:
<221> NAME/KEY: promoter
<222> LOCATION: (1)..(614)
<223> OTHER INFORMATION: e35S
<220> FEATURE:
<221> NAME/KEY: 5'UTR
<222> LOCATION: (650)..(710)
<223> OTHER INFORMATION: Wheat CAB leader
<220> FEATURE:
<221> NAME/KEY: Intron
<222> LOCATION: (727)..(1206)
<223> OTHER INFORMATION: rice actin
<220> FEATURE:
<221> NAME/KEY: CDS
<222> LOCATION: (1216)..(1917)
<223> OTHER INFORMATION: TIC809
<220> FEATURE:

```
<221> NAME/KEY: terminator
<222> LOCATION: (1921)..(2130)
<223> OTHER INFORMATION: Wheat Hsp17
<220> FEATURE:
<221> NAME/KEY: promoter
<222> LOCATION: (2168)..(2781)
<223> OTHER INFORMATION: CaMV 35S enh
<220> FEATURE:
<221> NAME/KEY: 5'UTR
<222> LOCATION: (2817)..(2877)
<223> OTHER INFORMATION: Wheat CAB leader
<220> FEATURE:
<221> NAME/KEY: Intron
<222> LOCATION: (2894)..(3373)
<223> OTHER INFORMATION: rice actin
<220> FEATURE:
<221> NAME/KEY: CDS
<222> LOCATION: (3383)..(4042)
<223> OTHER INFORMATION: TIC810
<220> FEATURE:
<221> NAME/KEY: terminator
<222> LOCATION: (4048)..(4257)
<223> OTHER INFORMATION: Wheat Hsp17

<400> SEQUENCE: 28

ggtccgatgt gagacttttc aacaaagggt aatatccgga aacctcctcg gattccattg     60

cccagctatc tgtcacttta ttgtgaagat agtggaaaag gaaggtggct cctacaaatg    120

ccatcattgc gataaaggaa aggccatcgt tgaagatgcc tctgccgaca gtggtcccaa    180

agatggaccc ccacccacga ggagcatcgt ggaaaaagaa gacgttccaa ccacgtcttc    240

aaagcaagtg gattgatgtg atggtccgat gtgagacttt tcaacaaagg gtaatatccg    300

gaaacctcct cggattccat tgcccagcta tctgtcactt tattgtgaag atagtggaaa    360

aggaaggtgg ctcctacaaa tgccatcatt gcgataaagg aaaggccatc gttgaagatg    420

cctctgccga cagtggtccc aaagatggac ccccacccac gaggagcatc gtggaaaaag    480

aagacgttcc aaccacgtct tcaaagcaag tggattgatg tgatatctcc actgacgtaa    540

gggatgacgc acaatcccac tatccttcgc aagacccttc ctctatataa ggaagttcat    600

ttcatttgga gaggacacgc tgacaagctg actctagcag atcctctaga accatcttcc    660

acacactcaa gccacactat tggagaacac acagggacaa cacaccataa gatccaaggg    720

aggcctccgc cgccgccggt aaccaccccg cccctctcct ctttctttct ccgttttttt    780

ttccgtctcg gtctcgatct ttggccttgg tagtttgggt gggcgagagg cggcttcgtg    840

cgcgcccaga tcggtgcgcg ggaggggcgg gatctcgcgg ctggggctct cgccggcgtg    900

gatccggccc ggatctcgcg gggaatgggg ctctcggatg tagatctgcg atccgccgtt    960

gttgggggag atgatggggg gtttaaaatt tccgccgtgc taaacaagat caggaagagg   1020

ggaaaagggc actatggttt atatttttat atatttctgc tgcttcgtca ggcttagatg   1080

tgctagatct ttctttcttc tttttgtggg tagaatttga atccctcagc attgttcatc   1140

ggtagttttt cttttcatga tttgtgacaa atgcagcctc gtgcggagct tttttgtagg   1200

tagaagtgat caacc atg gcc ttc ttc aac cgg gtg atc acc ctc acg gtg    1251
                 Met Ala Phe Phe Asn Arg Val Ile Thr Leu Thr Val
                 1               5                   10

ccg tcg tca gac gtg gtc aac tac tcg gag atc tac cag gtg gct cct     1299
Pro Ser Ser Asp Val Val Asn Tyr Ser Glu Ile Tyr Gln Val Ala Pro
        15                  20                  25

cag tat gtc aac cag gcc ctg acc ctg gcc aag tac ttc cag ggc gcc     1347
Gln Tyr Val Asn Gln Ala Leu Thr Leu Ala Lys Tyr Phe Gln Gly Ala
    30                  35                  40

atc gac ggc agc acc ctg agg ttc gac ttc gag aag gcg tta cag atc     1395
```

-continued

```
Ile Asp Gly Ser Thr Leu Arg Phe Asp Phe Glu Lys Ala Leu Gln Ile
45                  50                  55                  60

gcc aac gac atc ccg cag gcc gcg gtg gtc aac acc ctg aac cag acc     1443
Ala Asn Asp Ile Pro Gln Ala Ala Val Val Asn Thr Leu Asn Gln Thr
                65                  70                  75

gtc cag cag ggg acc gtc cag gtc agc gtc atg atc gac aag atc gtg     1491
Val Gln Gln Gly Thr Val Gln Val Ser Val Met Ile Asp Lys Ile Val
            80                  85                  90

gac atc atg aag aat gtc ctg tcc atc gtg ata gac aac aag aag ttt     1539
Asp Ile Met Lys Asn Val Leu Ser Ile Val Ile Asp Asn Lys Lys Phe
        95                  100                 105

tgg gat cag gtc acg gct gcc atc acc aac acc ttc acg aac ctg aac     1587
Trp Asp Gln Val Thr Ala Ala Ile Thr Asn Thr Phe Thr Asn Leu Asn
    110                 115                 120

agc cag gag tcg gag gcc tgg atc ttc tat tac aag gag gac gcc cac     1635
Ser Gln Glu Ser Glu Ala Trp Ile Phe Tyr Tyr Lys Glu Asp Ala His
125                 130                 135                 140

aag acg tcc tac tat tac aac atc ctc ttc gcc atc cag gac gaa gag     1683
Lys Thr Ser Tyr Tyr Tyr Asn Ile Leu Phe Ala Ile Gln Asp Glu Glu
                145                 150                 155

acg ggt ggc gtg atg gcc acg ctg ccc atc gcc ttc gac atc agt gtg     1731
Thr Gly Gly Val Met Ala Thr Leu Pro Ile Ala Phe Asp Ile Ser Val
            160                 165                 170

gac atc gag aag gag aag gtc ctg ttc gtg acc atc aag gac act gag     1779
Asp Ile Glu Lys Glu Lys Val Leu Phe Val Thr Ile Lys Asp Thr Glu
        175                 180                 185

aat tac gcc gtc acc gtc aag gcg atc aac gtg gtc cag gca ctc cag     1827
Asn Tyr Ala Val Thr Val Lys Ala Ile Asn Val Val Gln Ala Leu Gln
    190                 195                 200

tct agc agg gat tct aag gtg gtt gat gcg ttc aaa tcg cca cgg cac     1875
Ser Ser Arg Asp Ser Lys Val Val Asp Ala Phe Lys Ser Pro Arg His
205                 210                 215                 220

tta ccc cgg aag agg cat aag att tgc tct aac tcg tga tga             1917
Leu Pro Arg Lys Arg His Lys Ile Cys Ser Asn Ser
                225                 230

attctgcatg cgtttggacg tatgctcatt caggttggag ccaatttggt tgatgtgtgt   1977

gcgagttctt gcgagtctga tgagacatct ctgtattgtg tttctttccc cagtgttttc   2037

tgtacttgtg taatcggcta atcgccaaca gattcggcga tgaataaatg agaaataaat   2097

tgttctgatt ttgagtgcaa aaaaaaagga attagatctg tgtgtgtttt ttggatcccc   2157

agcttctgca ggtccgatgt gagacttttc aacaaagggt aatatccgga aacctcctcg   2217

gattccattg cccagctatc tgtcacttta ttgtgaagat agtggaaaag gaaggtggct   2277

cctacaaatg ccatcattgc gataaaggaa aggccatcgt tgaagatgcc tctgccgaca   2337

gtggtcccaa agatggaccc ccacccacga ggagcatcgt ggaaaaagaa gacgttccaa   2397

ccacgtcttc aaagcaagtg gattgatgtg atggtccgat gtgagacttt tcaacaaagg   2457

gtaatatccg gaaacctcct cggattccat tgcccagcta tctgtcactt tattgtgaag   2517

atagtggaaa aggaaggtgg ctcctacaaa tgccatcatt gcgataaagg aaaggccatc   2577

gttgaagatg cctctgccga cagtggtccc aaagatggac ccccacccac gaggagcatc   2637

gtggaaaaag aagacgttcc aaccacgtct tcaaagcaag tggattgatg tgatatctcc   2697

actgacgtaa gggatgacgc acaatcccac tatccttcgc aagacccttc ctctatataa   2757

ggaagttcat ttcatttgga gaggacacgc tgacaagctg actctagcag atcctctaga   2817

accatcttcc acacactcaa gccacactat tggagaacac acagggacaa cacaccataa   2877
```

-continued

```
gatccaaggg aggcctccgc cgccgccggt aaccaccccg cccctctcct ctttctttct   2937

ccgttttttt ttccgtctcg gtctcgatct ttggccttgg tagtttgggt gggcgagagg   2997

cggcttcgtg cgcgcccaga tcggtgcgcg ggaggggcgg gatctcgcgg ctggggctct   3057

cgccggcgtg gatccggccc ggatctcgcg gggaatgggg ctctcggatg tagatctgcg   3117

atccgccgtt gttgggggag atgatggggg gtttaaaatt tccgccgtgc taaacaagat   3177

caggaagagg ggaaaagggc actatggttt atatttttat atatttctgc tgcttcgtca   3237

ggcttagatg tgctagatct ttctttcttc tttttgtggg tagaatttga atccctcagc   3297

attgttcatc ggtagttttt cttttcatga tttgtgacaa atgcagcctc gtgcggagct   3357

tttttgtagg tagaagtgat caacc atg agc aaa gaa atc agg ctc aac ctt     3409
                            Met Ser Lys Glu Ile Arg Leu Asn Leu
                                        235                 240

tct cgt gag agc ggc gcc gac ctg tac ctc aag atc ctc gcc ttc gtg     3457
Ser Arg Glu Ser Gly Ala Asp Leu Tyr Leu Lys Ile Leu Ala Phe Val
            245                 250                 255

aag ccc gag cac ttc ttt cag gcg tac ctc ctg tgc cgc gag ttc gag     3505
Lys Pro Glu His Phe Phe Gln Ala Tyr Leu Leu Cys Arg Glu Phe Glu
        260                 265                 270

agc atc gtg gat cct aca acc cgc gag tct gac ttc gac aag acg ctg     3553
Ser Ile Val Asp Pro Thr Thr Arg Glu Ser Asp Phe Asp Lys Thr Leu
    275                 280                 285

acc atc gtg aag tcg gac tcc acc ctc gtg acc gtg ggc acg atg aac     3601
Thr Ile Val Lys Ser Asp Ser Thr Leu Val Thr Val Gly Thr Met Asn
290                 295                 300                 305

acc aag ctg gtc aat agc caa gag atc ctc gtg tcg gac ttg atc act     3649
Thr Lys Leu Val Asn Ser Gln Glu Ile Leu Val Ser Asp Leu Ile Thr
                310                 315                 320

caa gtc ggt tcc cag atc gcc gat acc ctc ggc atc acg gac atc gac     3697
Gln Val Gly Ser Gln Ile Ala Asp Thr Leu Gly Ile Thr Asp Ile Asp
            325                 330                 335

gcc aac acc cag caa cag ctc acg gag ctg atc ggc aac ctc ttc gtg     3745
Ala Asn Thr Gln Gln Gln Leu Thr Glu Leu Ile Gly Asn Leu Phe Val
        340                 345                 350

aac ctc aat tcc caa gtt cag gag tac atc tac ttc tac gag gag aag     3793
Asn Leu Asn Ser Gln Val Gln Glu Tyr Ile Tyr Phe Tyr Glu Glu Lys
    355                 360                 365

gag aag cag acc tcc tac cgc tac aac atc ctc ttc gtg ttc gaa aag     3841
Glu Lys Gln Thr Ser Tyr Arg Tyr Asn Ile Leu Phe Val Phe Glu Lys
                370                 375                 380                 385

gag tcg ttc atc acc att ctg cca atg ggc ttc gac gtg acc gtg aac     3889
Glu Ser Phe Ile Thr Ile Leu Pro Met Gly Phe Asp Val Thr Val Asn
            390                 395                 400

acg aac aag gag gcc gtc ctg aag ctg acc ccg aag gac aag gtt acc     3937
Thr Asn Lys Glu Ala Val Leu Lys Leu Thr Pro Lys Asp Lys Val Thr
        405                 410                 415

tac ggc cac gtc agc gtc aag gcc ctc aac atc atc cag ctc att acg     3985
Tyr Gly His Val Ser Val Lys Ala Leu Asn Ile Ile Gln Leu Ile Thr
    420                 425                 430

gag gac aag ttc aac ttc ctc gca acc ctc aag aag gct ctc aag acc     4033
Glu Asp Lys Phe Asn Phe Leu Ala Thr Leu Lys Lys Ala Leu Lys Thr
435                 440                 445

ctg tga tga gaattctgca tgcgtttgga cgtatgctca ttcaggttgg             4082
    Leu
    450

agccaatttg gttgatgtgt gtgcgagttc ttgcgagtct gatgagacat ctctgtattg   4142

tgtttctttc cccagtgttt tctgtacttg tgtaatcggc taatcgccaa cagattcggc   4202
```

gatgaataaa tgagaaataa attgttctga ttttgagtgc aaaaaaaaag gaatt 4257

<210> SEQ ID NO 29
<211> LENGTH: 232
<212> TYPE: PRT
<213> ORGANISM: Artificial Sequence
<220> FEATURE:
<223> OTHER INFORMATION: Synthetic Construct

<400> SEQUENCE: 29

Met Ala Phe Phe Asn Arg Val Ile Thr Leu Thr Val Pro Ser Ser Asp
1 5 10 15

Val Val Asn Tyr Ser Glu Ile Tyr Gln Val Ala Pro Gln Tyr Val Asn
20 25 30

Gln Ala Leu Thr Leu Ala Lys Tyr Phe Gln Gly Ala Ile Asp Gly Ser
35 40 45

Thr Leu Arg Phe Asp Phe Glu Lys Ala Leu Gln Ile Ala Asn Asp Ile
50 55 60

Pro Gln Ala Ala Val Val Asn Thr Leu Asn Gln Thr Val Gln Gln Gly
65 70 75 80

Thr Val Gln Val Ser Val Met Ile Asp Lys Ile Val Asp Ile Met Lys
85 90 95

Asn Val Leu Ser Ile Val Ile Asp Asn Lys Lys Phe Trp Asp Gln Val
100 105 110

Thr Ala Ala Ile Thr Asn Thr Phe Thr Asn Leu Asn Ser Gln Glu Ser
115 120 125

Glu Ala Trp Ile Phe Tyr Tyr Lys Glu Asp Ala His Lys Thr Ser Tyr
130 135 140

Tyr Tyr Asn Ile Leu Phe Ala Ile Gln Asp Glu Glu Thr Gly Gly Val
145 150 155 160

Met Ala Thr Leu Pro Ile Ala Phe Asp Ile Ser Val Asp Ile Glu Lys
165 170 175

Glu Lys Val Leu Phe Val Thr Ile Lys Asp Thr Glu Asn Tyr Ala Val
180 185 190

Thr Val Lys Ala Ile Asn Val Val Gln Ala Leu Gln Ser Ser Arg Asp
195 200 205

Ser Lys Val Val Asp Ala Phe Lys Ser Pro Arg His Leu Pro Arg Lys
210 215 220

Arg His Lys Ile Cys Ser Asn Ser
225 230

<210> SEQ ID NO 30
<211> LENGTH: 218
<212> TYPE: PRT
<213> ORGANISM: Artificial Sequence
<220> FEATURE:
<223> OTHER INFORMATION: Synthetic Construct

<400> SEQUENCE: 30

Met Ser Lys Glu Ile Arg Leu Asn Leu Ser Arg Glu Ser Gly Ala Asp
1 5 10 15

Leu Tyr Leu Lys Ile Leu Ala Phe Val Lys Pro Glu His Phe Phe Gln
20 25 30

Ala Tyr Leu Leu Cys Arg Glu Phe Glu Ser Ile Val Asp Pro Thr Thr
35 40 45

Arg Glu Ser Asp Phe Asp Lys Thr Leu Thr Ile Val Lys Ser Asp Ser
50 55 60

```
Thr Leu Val Thr Val Gly Thr Met Asn Thr Lys Leu Val Asn Ser Gln
65                  70                  75                  80

Glu Ile Leu Val Ser Asp Leu Ile Thr Gln Val Gly Ser Gln Ile Ala
                85                  90                  95

Asp Thr Leu Gly Ile Thr Asp Ile Asp Ala Asn Thr Gln Gln Gln Leu
            100                 105                 110

Thr Glu Leu Ile Gly Asn Leu Phe Val Asn Leu Asn Ser Gln Val Gln
        115                 120                 125

Glu Tyr Ile Tyr Phe Tyr Glu Glu Lys Glu Lys Gln Thr Ser Tyr Arg
    130                 135                 140

Tyr Asn Ile Leu Phe Val Phe Glu Lys Glu Ser Phe Ile Thr Ile Leu
145                 150                 155                 160

Pro Met Gly Phe Asp Val Thr Val Asn Thr Asn Lys Glu Ala Val Leu
                165                 170                 175

Lys Leu Thr Pro Lys Asp Lys Val Thr Tyr Gly His Val Ser Val Lys
            180                 185                 190

Ala Leu Asn Ile Ile Gln Leu Ile Thr Glu Asp Lys Phe Asn Phe Leu
        195                 200                 205

Ala Thr Leu Lys Lys Ala Leu Lys Thr Leu
    210                 215
```

<210> SEQ ID NO 31
<211> LENGTH: 5079
<212> TYPE: DNA
<213> ORGANISM: Artificial Sequence
<220> FEATURE:
<223> OTHER INFORMATION: synthetic sequence; expression cassettes encoding TIC809 and TIC810 in pMON64139
<220> FEATURE:
<221> NAME/KEY: misc_feature
<223> OTHER INFORMATION: pMON64139
<220> FEATURE:
<221> NAME/KEY: promoter
<222> LOCATION: (1)..(614)
<223> OTHER INFORMATION: e35S
<220> FEATURE:
<221> NAME/KEY: 5'UTR
<222> LOCATION: (650)..(710)
<223> OTHER INFORMATION: Wheat CAB leader
<220> FEATURE:
<221> NAME/KEY: Intron
<222> LOCATION: (727)..(1206)
<223> OTHER INFORMATION: rice actin (Exon 727-738; intron 739-1199; Exon 1200-1206)
<220> FEATURE:
<221> NAME/KEY: transit_peptide
<222> LOCATION: (1230)..(1370)
<223> OTHER INFORMATION: Maize SSU-signal
<220> FEATURE:
<221> NAME/KEY: Intron
<222> LOCATION: (1231)..(1539)
<223> OTHER INFORMATION: Zm RbcS
<220> FEATURE:
<221> NAME/KEY: transit_peptide
<222> LOCATION: (1540)..(1626)
<223> OTHER INFORMATION: Zm RbcS
<220> FEATURE:
<221> NAME/KEY: CDS
<222> LOCATION: (1627)..(2328)
<223> OTHER INFORMATION: TIC809
<220> FEATURE:
<221> NAME/KEY: terminator
<222> LOCATION: (2332)..(2541)
<223> OTHER INFORMATION: Wheat Hsp17
<220> FEATURE:
<221> NAME/KEY: promoter
<222> LOCATION: (2579)..(3192)
<223> OTHER INFORMATION: CaMV 35S enh
<220> FEATURE:
<221> NAME/KEY: 5'UTR
<222> LOCATION: (3228)..(3288)
<223> OTHER INFORMATION: Wheat CAB leader
<220> FEATURE:
<221> NAME/KEY: Intron
<222> LOCATION: (3305)..(3784)
<223> OTHER INFORMATION: Rice actin (Exon 3305-3316; intron 3317-3777;
Exon 3778-3784)
<220> FEATURE:
<221> NAME/KEY: transit_peptide
<222> LOCATION: (3808)..(3948)
<223> OTHER INFORMATION: Maize SSU - signal
<220> FEATURE:
<221> NAME/KEY: Intron
<222> LOCATION: (3949)..(4117)
<223> OTHER INFORMATION: Zm RbcS
<220> FEATURE:
<221> NAME/KEY: transit_peptide
<222> LOCATION: (4118)..(4204)
<223> OTHER INFORMATION: Zm RbcS
<220> FEATURE:
<221> NAME/KEY: CDS
<222> LOCATION: (4205)..(4864)
<223> OTHER INFORMATION: TIC810
<220> FEATURE:
<221> NAME/KEY: terminator
<222> LOCATION: (4870)..(5079)
<223> OTHER INFORMATION: Wheat Hsp17

<400> SEQUENCE: 31
ggtccgatgt gagacttttc aacaaagggt aatatccgga aacctcctcg gattccattg 60
cccagctatc tgtcacttta ttgtgaagat agtggaaaag gaaggtggct cctacaaatg 120
ccatcattgc gataaaggaa aggccatcgt tgaagatgcc tctgccgaca gtggtcccaa 180
agatggaccc ccacccacga ggagcatcgt ggaaaaagaa gacgttccaa ccacgtcttc 240
aaagcaagtg gattgatgtg atggtccgat gtgagacttt tcaacaaagg gtaatatccg 300
gaaacctcct cggattccat tgcccagcta tctgtcactt tattgtgaag atagtggaaa 360
aggaaggtgg ctcctacaaa tgccatcatt gcgataaagg aaaggccatc gttgaagatg 420
cctctgccga cagtggtccc aaagatggac ccccacccac gaggagcatc gtggaaaaag 480
aagacgttcc aaccacgtct tcaaagcaag tggattgatg tgatatctcc actgacgtaa 540
gggatgacgc acaatcccac tatccttcgc aagacccttc ctctatataa ggaagttcat 600
ttcatttgga gaggacacgc tgacaagctg actctagcag atcctctaga accatcttcc 660
acacactcaa gccacactat tggagaacac acagggacaa cacaccataa gatccaaggg 720
aggcctccgc cgccgccggt aaccaccccg cccctctcct ctttctttct ccgttttttt 780
ttccgtctcg gtctcgatct ttggccttgg tagtttgggt gggcgagagg cggcttcgtg 840
cgcgcccaga tcggtgcgcg ggaggggcgg gatctcgcgg ctggggctct cgccggcgtg 900
gatccggccc ggatctcgcg gggaatgggg ctctcggatg tagatctgcg atccgccgtt 960
gttgggggag atgatggggg gtttaaaatt tccgccgtgc taaacaagat caggaagagg 1020
ggaaaagggc actatggttt atatttttat atatttctgc tgcttcgtca ggcttagatg 1080
tgctagatct ttctttcttc tttttgtggg tagaatttga atccctcagc attgttcatc 1140
ggtagttttt cttttcatga tttgtgacaa atgcagcctc gtgcggagct tttttgtagg 1200
tagaagtgat caacctctag aggatcagca tggcgcccac cgtgatgatg gcctcgtcgg 1260
ccaccgccgt cgctccgttc ctggggctca agtccaccgc cagcctcccc gtcgcccgcc 1320
gctcctccag aagcctcggc aacgtcagca acggcggaag gatccggtgc atgcaggtaa 1380
caaatgcatc ctagctagta gttctttgca ttgcagcagc tgcagctagc gagttagtaa 1440

-continued

```
taggaaggga actgatgatc catgcatgga ctgatgtgtg ttgcccatcc catcccatcc   1500

catttcccaa acgaaccgaa aacaccgtac tacgtgcagg tgtggcccta cggcaacaag   1560

aagttcgaga cgctgtcgta cctgccgccg ctgtcgaccg gcgggcgcat ccgctgcatg   1620

caggcc atg gcc ttc ttc aac cgg gtg atc acc ctc acg gtg ccg tcg      1668
       Met Ala Phe Phe Asn Arg Val Ile Thr Leu Thr Val Pro Ser
       1               5                   10

tca gac gtg gtc aac tac tcg gag atc tac cag gtg gct cct cag tat     1716
Ser Asp Val Val Asn Tyr Ser Glu Ile Tyr Gln Val Ala Pro Gln Tyr
15                  20                  25                  30

gtc aac cag gcc ctg acc ctg gcc aag tac ttc cag ggc gcc atc gac     1764
Val Asn Gln Ala Leu Thr Leu Ala Lys Tyr Phe Gln Gly Ala Ile Asp
                35                  40                  45

ggc agc acc ctg agg ttc gac ttc gag aag gcg tta cag atc gcc aac     1812
Gly Ser Thr Leu Arg Phe Asp Phe Glu Lys Ala Leu Gln Ile Ala Asn
            50                  55                  60

gac atc ccg cag gcc gcg gtg gtc aac acc ctg aac cag acc gtc cag     1860
Asp Ile Pro Gln Ala Ala Val Val Asn Thr Leu Asn Gln Thr Val Gln
        65                  70                  75

cag ggg acc gtc cag gtc agc gtc atg atc gac aag atc gtg gac atc     1908
Gln Gly Thr Val Gln Val Ser Val Met Ile Asp Lys Ile Val Asp Ile
    80                  85                  90

atg aag aat gtc ctg tcc atc gtg ata gac aac aag aag ttt tgg gat     1956
Met Lys Asn Val Leu Ser Ile Val Ile Asp Asn Lys Lys Phe Trp Asp
95                  100                 105                 110

cag gtc acg gct gcc atc acc aac acc ttc acg aac ctg aac agc cag     2004
Gln Val Thr Ala Ala Ile Thr Asn Thr Phe Thr Asn Leu Asn Ser Gln
                115                 120                 125

gag tcg gag gcc tgg atc ttc tat tac aag gag gac gcc cac aag acg     2052
Glu Ser Glu Ala Trp Ile Phe Tyr Tyr Lys Glu Asp Ala His Lys Thr
            130                 135                 140

tcc tac tat tac aac atc ctc ttc gcc atc cag gac gaa gag acg ggt     2100
Ser Tyr Tyr Tyr Asn Ile Leu Phe Ala Ile Gln Asp Glu Glu Thr Gly
        145                 150                 155

ggc gtg atg gcc acg ctg ccc atc gcc ttc gac atc agt gtg gac atc     2148
Gly Val Met Ala Thr Leu Pro Ile Ala Phe Asp Ile Ser Val Asp Ile
    160                 165                 170

gag aag gag aag gtc ctg ttc gtg acc atc aag gac act gag aat tac     2196
Glu Lys Glu Lys Val Leu Phe Val Thr Ile Lys Asp Thr Glu Asn Tyr
175                 180                 185                 190

gcc gtc acc gtc aag gcg atc aac gtg gtc cag gca ctc cag tct agc     2244
Ala Val Thr Val Lys Ala Ile Asn Val Val Gln Ala Leu Gln Ser Ser
                195                 200                 205

agg gat tct aag gtg gtt gat gcg ttc aaa tcg cca cgg cac tta ccc     2292
Arg Asp Ser Lys Val Val Asp Ala Phe Lys Ser Pro Arg His Leu Pro
            210                 215                 220

cgg aag agg cat aag att tgc tct aac tcg tga tga attctgcatg          2338
Arg Lys Arg His Lys Ile Cys Ser Asn Ser
        225                 230

cgtttggacg tatgctcatt caggttggag ccaatttggt tgatgtgtgt gcgagttctt   2398

gcgagtctga tgagacatct ctgtattgtg tttctttccc cagtgttttc tgtacttgtg   2458

taatcggcta atcgccaaca gattcggcga tgaataaatg agaaataaat tgttctgatt   2518

ttgagtgcaa aaaaaaagga attagatctg tgtgtgtttt ttggatcccc agcttctgca   2578

ggtccgatgt gagacttttc aacaaagggt aatatccgga aacctcctcg gattccattg   2638

cccagctatc tgtcacttta ttgtgaagat agtggaaaag gaaggtggct cctacaaatg   2698
```

-continued

```
ccatcattgc gataaaggaa aggccatcgt tgaagatgcc tctgccgaca gtggtcccaa   2758

agatggaccc ccacccacga ggagcatcgt ggaaaaagaa gacgttccaa ccacgtcttc   2818

aaagcaagtg gattgatgtg atggtccgat gtgagacttt tcaacaaagg gtaatatccg   2878

gaaacctcct cggattccat tgcccagcta tctgtcactt tattgtgaag atagtggaaa   2938

aggaaggtgg ctcctacaaa tgccatcatt gcgataaagg aaaggccatc gttgaagatg   2998

cctctgccga cagtggtccc aaagatggac ccccacccac gaggagcatc gtggaaaaag   3058

aagacgttcc aaccacgtct tcaaagcaag tggattgatg tgatatctcc actgacgtaa   3118

gggatgacgc acaatcccac tatccttcgc aagacccttc ctctatataa ggaagttcat   3178

ttcatttgga gaggacacgc tgacaagctg actctagcag atcctctaga accatcttcc   3238

acacactcaa gccacactat tggagaacac acagggacaa cacaccataa gatccaaggg   3298

aggcctccgc cgccgccggt aaccaccccg cccctctcct ctttctttct ccgttttttt   3358

ttccgtctcg gtctcgatct ttggccttgg tagtttgggt gggcgagagg cggcttcgtg   3418

cgcgcccaga tcggtgcgcg ggaggggcgg gatctcgcgg ctggggctct cgccggcgtg   3478

gatccggccc ggatctcgcg gggaatgggg ctctcggatg tagatctgcg atccgccgtt   3538

gttgggggag atgatggggg gtttaaaatt tccgccgtgc taaacaagat caggaagagg   3598

ggaaaagggc actatggttt atatttttat atatttctgc tgcttcgtca ggcttagatg   3658

tgctagatct ttctttcttc tttttgtggg tagaatttga atccctcagc attgttcatc   3718

ggtagttttt cttttcatga tttgtgacaa atgcagcctc gtgcggagct tttttgtagg   3778

tagaagtgat caacctctag aggatcagca tggcgcccac cgtgatgatg gcctcgtcgg   3838

ccaccgccgt cgctccgttc ctggggctca agtccaccgc cagcctcccc gtcgcccgcc   3898

gctcctccag aagcctcggc aacgtcagca acggcggaag gatccggtgc atgcaggtaa   3958

caaatgcatc ctagctagta gttctttgca ttgcagcagc tgcagctagc gagttagtaa   4018

taggaaggga actgatgatc catgcatgga ctgatgtgtg ttgcccatcc catcccatcc   4078

catttcccaa acgaaccgaa aacaccgtac tacgtgcagg tgtggcccta cggcaacaag   4138

aagttcgaga cgctgtcgta cctgccgccg ctgtcgaccg gcgggcgcat ccgctgcatg   4198

caggcc atg agc aaa gaa atc agg ctc aac ctt tct cgt gag agc ggc      4246
       Met Ser Lys Glu Ile Arg Leu Asn Leu Ser Arg Glu Ser Gly
               235                 240                 245

gcc gac ctg tac ctc aag atc ctc gcc ttc gtg aag ccc gag cac ttc     4294
Ala Asp Leu Tyr Leu Lys Ile Leu Ala Phe Val Lys Pro Glu His Phe
            250                 255                 260

ttt cag gcg tac ctc ctg tgc cgc gag ttc gag agc atc gtg gat cct     4342
Phe Gln Ala Tyr Leu Leu Cys Arg Glu Phe Glu Ser Ile Val Asp Pro
        265                 270                 275

aca acc cgc gag tct gac ttc gac aag acg ctg acc atc gtg aag tcg     4390
Thr Thr Arg Glu Ser Asp Phe Asp Lys Thr Leu Thr Ile Val Lys Ser
    280                 285                 290

gac tcc acc ctc gtg acc gtg ggc acg atg aac acc aag ctg gtc aat     4438
Asp Ser Thr Leu Val Thr Val Gly Thr Met Asn Thr Lys Leu Val Asn
295                 300                 305                 310

agc caa gag atc ctc gtg tcg gac ttg atc act caa gtc ggt tcc cag     4486
Ser Gln Glu Ile Leu Val Ser Asp Leu Ile Thr Gln Val Gly Ser Gln
                315                 320                 325

atc gcc gat acc ctc ggc atc acg gac atc gac gcc aac acc cag caa     4534
Ile Ala Asp Thr Leu Gly Ile Thr Asp Ile Asp Ala Asn Thr Gln Gln
            330                 335                 340

cag ctc acg gag ctg atc ggc aac ctc ttc gtg aac ctc aat tcc caa     4582
```

```
Gln Leu Thr Glu Leu Ile Gly Asn Leu Phe Val Asn Leu Asn Ser Gln
        345                 350                 355

gtt cag gag tac atc tac ttc tac gag gag aag gag aag cag acc tcc      4630
Val Gln Glu Tyr Ile Tyr Phe Tyr Glu Glu Lys Glu Lys Gln Thr Ser
    360                 365                 370

tac cgc tac aac atc ctc ttc gtg ttc gaa aag gag tcg ttc atc acc      4678
Tyr Arg Tyr Asn Ile Leu Phe Val Phe Glu Lys Glu Ser Phe Ile Thr
375                 380                 385                 390

att ctg cca atg ggc ttc gac gtg acc gtg aac acg aac aag gag gcc      4726
Ile Leu Pro Met Gly Phe Asp Val Thr Val Asn Thr Asn Lys Glu Ala
                395                 400                 405

gtc ctg aag ctg acc ccg aag gac aag gtt acc tac ggc cac gtc agc      4774
Val Leu Lys Leu Thr Pro Lys Asp Lys Val Thr Tyr Gly His Val Ser
            410                 415                 420

gtc aag gcc ctc aac atc atc cag ctc att acg gag gac aag ttc aac      4822
Val Lys Ala Leu Asn Ile Ile Gln Leu Ile Thr Glu Asp Lys Phe Asn
        425                 430                 435

ttc ctc gca acc ctc aag aag gct ctc aag acc ctg tga tga              4864
Phe Leu Ala Thr Leu Lys Lys Ala Leu Lys Thr Leu
    440                 445                 450

gaattctgca tgcgtttgga cgtatgctca ttcaggttgg agccaatttg gttgatgtgt   4924

gtgcgagttc ttgcgagtct gatgagacat ctctgtattg tgtttctttc cccagtgttt   4984

tctgtacttg tgtaatcggc taatcgccaa cagattcggc gatgaataaa tgagaaataa   5044

attgttctga ttttgagtgc aaaaaaaaag gaatt                              5079


<210> SEQ ID NO 32
<211> LENGTH: 232
<212> TYPE: PRT
<213> ORGANISM: Artificial Sequence
<220> FEATURE:
<223> OTHER INFORMATION: Synthetic Construct

<400> SEQUENCE: 32

Met Ala Phe Phe Asn Arg Val Ile Thr Leu Thr Val Pro Ser Ser Asp
1               5                   10                  15

Val Val Asn Tyr Ser Glu Ile Tyr Gln Val Ala Pro Gln Tyr Val Asn
            20                  25                  30

Gln Ala Leu Thr Leu Ala Lys Tyr Phe Gln Gly Ala Ile Asp Gly Ser
        35                  40                  45

Thr Leu Arg Phe Asp Phe Glu Lys Ala Leu Gln Ile Ala Asn Asp Ile
    50                  55                  60

Pro Gln Ala Ala Val Val Asn Thr Leu Asn Gln Thr Val Gln Gln Gly
65                  70                  75                  80

Thr Val Gln Val Ser Val Met Ile Asp Lys Ile Val Asp Ile Met Lys
                85                  90                  95

Asn Val Leu Ser Ile Val Ile Asp Asn Lys Lys Phe Trp Asp Gln Val
            100                 105                 110

Thr Ala Ala Ile Thr Asn Thr Phe Thr Asn Leu Asn Ser Gln Glu Ser
        115                 120                 125

Glu Ala Trp Ile Phe Tyr Tyr Lys Glu Asp Ala His Lys Thr Ser Tyr
    130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
```

```
            180                 185                 190

Thr Val Lys Ala Ile Asn Val Val Gln Ala Leu Gln Ser Ser Arg Asp
        195                 200                 205

Ser Lys Val Val Asp Ala Phe Lys Ser Pro Arg His Leu Pro Arg Lys
    210                 215                 220

Arg His Lys Ile Cys Ser Asn Ser
225                 230
```

<210> SEQ ID NO 33
<211> LENGTH: 218
<212> TYPE: PRT
<213> ORGANISM: Artificial Sequence
<220> FEATURE:
<223> OTHER INFORMATION: Synthetic Construct

<400> SEQUENCE: 33

```
Met Ser Lys Glu Ile Arg Leu Asn Leu Ser Arg Glu Ser Gly Ala Asp
1               5                   10                  15

Leu Tyr Leu Lys Ile Leu Ala Phe Val Lys Pro Glu His Phe Phe Gln
            20                  25                  30

Ala Tyr Leu Leu Cys Arg Glu Phe Glu Ser Ile Val Asp Pro Thr Thr
        35                  40                  45

Arg Glu Ser Asp Phe Asp Lys Thr Leu Thr Ile Val Lys Ser Asp Ser
    50                  55                  60

Thr Leu Val Thr Val Gly Thr Met Asn Thr Lys Leu Val Asn Ser Gln
65                  70                  75                  80

Glu Ile Leu Val Ser Asp Leu Ile Thr Gln Val Gly Ser Gln Ile Ala
                85                  90                  95

Asp Thr Leu Gly Ile Thr Asp Ile Asp Ala Asn Thr Gln Gln Gln Leu
            100                 105                 110

Thr Glu Leu Ile Gly Asn Leu Phe Val Asn Leu Asn Ser Gln Val Gln
        115                 120                 125

Glu Tyr Ile Tyr Phe Tyr Glu Glu Lys Glu Lys Gln Thr Ser Tyr Arg
    130                 135                 140

Tyr Asn Ile Leu Phe Val Phe Glu Lys Glu Ser Phe Ile Thr Ile Leu
145                 150                 155                 160

Pro Met Gly Phe Asp Val Thr Val Asn Thr Asn Lys Glu Ala Val Leu
                165                 170                 175

Lys Leu Thr Pro Lys Asp Lys Val Thr Tyr Gly His Val Ser Val Lys
            180                 185                 190

Ala Leu Asn Ile Ile Gln Leu Ile Thr Glu Asp Lys Phe Asn Phe Leu
        195                 200                 205

Ala Thr Leu Lys Lys Ala Leu Lys Thr Leu
    210                 215
```

<210> SEQ ID NO 34
<211> LENGTH: 2148
<212> TYPE: DNA
<213> ORGANISM: Artificial Sequence
<220> FEATURE:
<223> OTHER INFORMATION: synthetic sequence; expression cassette in
      pMON70513 encoding TIC809
<220> FEATURE:
<221> NAME/KEY: misc_feature
<223> OTHER INFORMATION: pMON70513 plant expression cassette
<220> FEATURE:
<221> NAME/KEY: promoter
<222> LOCATION: (1)..(614)
<223> OTHER INFORMATION: e35S
<220> FEATURE:

-continued

```
<221> NAME/KEY: 5'UTR
<222> LOCATION: (650)..(710)
<223> OTHER INFORMATION: Wheat CAB leader
<220> FEATURE:
<221> NAME/KEY: Intron
<222> LOCATION: (727)..(1206)
<223> OTHER INFORMATION: rice actin
<220> FEATURE:
<221> NAME/KEY: CDS
<222> LOCATION: (1216)..(1917)
<223> OTHER INFORMATION: TIC809
<220> FEATURE:
<221> NAME/KEY: terminator
<222> LOCATION: (1939)..(2148)
<223> OTHER INFORMATION: Wheat Hsp17

<400> SEQUENCE: 34

ggtccgatgt gagacttttc aacaaagggt aatatccgga aacctcctcg gattccattg     60

cccagctatc tgtcacttta ttgtgaagat agtggaaaag gaaggtggct cctacaaatg    120

ccatcattgc gataaaggaa aggccatcgt tgaagatgcc tctgccgaca gtggtcccaa    180

agatggaccc ccacccacga ggagcatcgt ggaaaaagaa gacgttccaa ccacgtcttc    240

aaagcaagtg gattgatgtg atggtccgat gtgagacttt tcaacaaagg gtaatatccg    300

gaaacctcct cggattccat tgcccagcta tctgtcactt tattgtgaag atagtggaaa    360

aggaaggtgg ctcctacaaa tgccatcatt gcgataaagg aaaggccatc gttgaagatg    420

cctctgccga cagtggtccc aaagatggac ccccacccac gaggagcatc gtggaaaaag    480

aagacgttcc aaccacgtct tcaaagcaag tggattgatg tgatatctcc actgacgtaa    540

gggatgacgc acaatcccac tatccttcgc aagacccttc ctctatataa ggaagttcat    600

ttcatttgga gaggacacgc tgacaagctg actctagcag atcctctaga accatcttcc    660

acacactcaa gccacactat tggagaacac acagggacaa cacaccataa gatccaaggg    720

aggcctccgc cgccgccggt aaccaccccg cccctctcct ctttctttct ccgttttttt    780

ttccgtctcg gtctcgatct ttggccttgg tagtttgggt gggcgagagg cggcttcgtg    840

cgcgcccaga tcggtgcgcg ggaggggcgg gatctcgcgg ctggggctct cgccggcgtg    900

gatccggccc ggatctcgcg gggaatgggg ctctcggatg tagatctgcg atccgccgtt    960

gttgggggag atgatggggg gtttaaaatt tccgccgtgc taaacaagat caggaagagg   1020

ggaaaagggc actatggttt atatttttat atatttctgc tgcttcgtca ggcttagatg   1080

tgctagatct ttctttcttc tttttgtggg tagaatttga atccctcagc attgttcatc   1140

ggtagttttt cttttcatga tttgtgacaa atgcagcctc gtgcggagct tttttgtagg   1200

tagaagtgat caacc atg gcc ttc ttc aac cgg gtg atc acc ctc acg gtg    1251
                 Met Ala Phe Phe Asn Arg Val Ile Thr Leu Thr Val
                 1               5                   10

ccg tcg tca gac gtg gtc aac tac tcg gag atc tac cag gtg gct cct     1299
Pro Ser Ser Asp Val Val Asn Tyr Ser Glu Ile Tyr Gln Val Ala Pro
        15                  20                  25

cag tat gtc aac cag gcc ctg acc ctg gcc aag tac ttc cag ggc gcc     1347
Gln Tyr Val Asn Gln Ala Leu Thr Leu Ala Lys Tyr Phe Gln Gly Ala
    30                  35                  40

atc gac ggc agc acc ctg agg ttc gac ttc gag aag gcg tta cag atc     1395
Ile Asp Gly Ser Thr Leu Arg Phe Asp Phe Glu Lys Ala Leu Gln Ile
45                  50                  55                  60

gcc aac gac atc ccg cag gcc gcg gtg gtc aac acc ctg aac cag acc     1443
Ala Asn Asp Ile Pro Gln Ala Ala Val Val Asn Thr Leu Asn Gln Thr
                65                  70                  75

gtc cag cag ggg acc gtc cag gtc agc gtc atg atc gac aag atc gtg     1491
```

```
Val Gln Gln Gly Thr Val Gln Val Ser Val Met Ile Asp Lys Ile Val
            80                  85                  90

gac atc atg aag aat gtc ctg tcc atc gtg ata gac aac aag aag ttt      1539
Asp Ile Met Lys Asn Val Leu Ser Ile Val Ile Asp Asn Lys Lys Phe
        95                  100                 105

tgg gat cag gtc acg gct gcc atc acc aac acc ttc acg aac ctg aac      1587
Trp Asp Gln Val Thr Ala Ala Ile Thr Asn Thr Phe Thr Asn Leu Asn
    110                 115                 120

agc cag gag tcg gag gcc tgg atc ttc tat tac aag gag gac gcc cac      1635
Ser Gln Glu Ser Glu Ala Trp Ile Phe Tyr Tyr Lys Glu Asp Ala His
125                 130                 135                 140

aag acg tcc tac tat tac aac atc ctc ttc gcc atc cag gac gaa gag      1683
Lys Thr Ser Tyr Tyr Tyr Asn Ile Leu Phe Ala Ile Gln Asp Glu Glu
                145                 150                 155

acg ggt ggc gtg atg gcc acg ctg ccc atc gcc ttc gac atc agt gtg      1731
Thr Gly Gly Val Met Ala Thr Leu Pro Ile Ala Phe Asp Ile Ser Val
            160                 165                 170

gac atc gag aag gag aag gtc ctg ttc gtg acc atc aag gac act gag      1779
Asp Ile Glu Lys Glu Lys Val Leu Phe Val Thr Ile Lys Asp Thr Glu
        175                 180                 185

aat tac gcc gtc acc gtc aag gcg atc aac gtg gtc cag gca ctc cag      1827
Asn Tyr Ala Val Thr Val Lys Ala Ile Asn Val Val Gln Ala Leu Gln
    190                 195                 200

tct agc agg gat tct aag gtg gtt gat gcg ttc aaa tcg cca cgg cac      1875
Ser Ser Arg Asp Ser Lys Val Val Asp Ala Phe Lys Ser Pro Arg His
205                 210                 215                 220

tta ccc cgg aag agg cat aag att tgc tct aac tcg tga tga              1917
Leu Pro Arg Lys Arg His Lys Ile Cys Ser Asn Ser
                225                 230

attcggatcc aagggcgaat tctgcatgcg tttggacgta tgctcattca ggttggagcc   1977

aatttggttg atgtgtgtgc gagttcttgc gagtctgatg agacatctct gtattgtgtt   2037

tctttcccca gtgttttctg tacttgtgta atcggctaat cgccaacaga ttcggcgatg   2097

aataaatgag aaataaattg ttctgatttt gagtgcaaaa aaaaaggaat t             2148


<210> SEQ ID NO 35
<211> LENGTH: 232
<212> TYPE: PRT
<213> ORGANISM: Artificial Sequence
<220> FEATURE:
<223> OTHER INFORMATION: Synthetic Construct

<400> SEQUENCE: 35

Met Ala Phe Phe Asn Arg Val Ile Thr Leu Thr Val Pro Ser Ser Asp
1               5                   10                  15

Val Val Asn Tyr Ser Glu Ile Tyr Gln Val Ala Pro Gln Tyr Val Asn
            20                  25                  30

Gln Ala Leu Thr Leu Ala Lys Tyr Phe Gln Gly Ala Ile Asp Gly Ser
        35                  40                  45

Thr Leu Arg Phe Asp Phe Glu Lys Ala Leu Gln Ile Ala Asn Asp Ile
    50                  55                  60

Pro Gln Ala Ala Val Val Asn Thr Leu Asn Gln Thr Val Gln Gln Gly
65                  70                  75                  80

Thr Val Gln Val Ser Val Met Ile Asp Lys Ile Val Asp Ile Met Lys
                85                  90                  95

Asn Val Leu Ser Ile Val Ile Asp Asn Lys Lys Phe Trp Asp Gln Val
            100                 105                 110

Thr Ala Ala Ile Thr Asn Thr Phe Thr Asn Leu Asn Ser Gln Glu Ser
```

```
        115                 120                 125

Glu Ala Trp Ile Phe Tyr Tyr Lys Glu Asp Ala His Lys Thr Ser Tyr
    130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
            180                 185                 190

Thr Val Lys Ala Ile Asn Val Val Gln Ala Leu Gln Ser Ser Arg Asp
        195                 200                 205

Ser Lys Val Val Asp Ala Phe Lys Ser Pro Arg His Leu Pro Arg Lys
    210                 215                 220

Arg His Lys Ile Cys Ser Asn Ser
225                 230


<210> SEQ ID NO 36
<211> LENGTH: 2541
<212> TYPE: DNA
<213> ORGANISM: Artificial Seqeuence
<220> FEATURE:
<223> OTHER INFORMATION: synthetic sequence; expression cassette in
      pMON70514 encoding TIC809
<220> FEATURE:
<221> NAME/KEY: misc_feature
<223> OTHER INFORMATION: pMON70514 plant expression cassette
<220> FEATURE:
<221> NAME/KEY: promoter
<222> LOCATION: (1)..(614)
<223> OTHER INFORMATION: e35S
<220> FEATURE:
<221> NAME/KEY: 5'UTR
<222> LOCATION: (650)..(710)
<223> OTHER INFORMATION: Wheat CAB leader
<220> FEATURE:
<221> NAME/KEY: Intron
<222> LOCATION: (727)..(1206)
<223> OTHER INFORMATION: rice actin
<220> FEATURE:
<221> NAME/KEY: transit_peptide
<222> LOCATION: (1230)..(1270)
<223> OTHER INFORMATION: Zm RbcS
<220> FEATURE:
<221> NAME/KEY: Intron
<222> LOCATION: (1371)..(1539)
<223> OTHER INFORMATION: Zm RbcS
<220> FEATURE:
<221> NAME/KEY: transit_peptide
<222> LOCATION: (1540)..(1626)
<223> OTHER INFORMATION: Zm RbcS
<220> FEATURE:
<221> NAME/KEY: CDS
<222> LOCATION: (1627)..(2328)
<223> OTHER INFORMATION: TIC809
<220> FEATURE:
<221> NAME/KEY: terminator
<222> LOCATION: (2332)..(2541)
<223> OTHER INFORMATION: Wheat Hsp17

<400> SEQUENCE: 36

ggtccgatgt gagacttttc aacaaagggt aatatccgga aacctcctcg gattccattg     60

cccagctatc tgtcacttta ttgtgaagat agtggaaaag gaaggtggct cctacaaatg    120

ccatcattgc gataaaggaa aggccatcgt tgaagatgcc tctgccgaca gtggtcccaa    180

agatggaccc ccacccacga ggagcatcgt ggaaaaagaa gacgttccaa ccacgtcttc    240

aaagcaagtg gattgatgtg atggtccgat gtgagacttt tcaacaaagg gtaatatccg    300
```

-continued

```
gaaacctcct cggattccat tgcccagcta tctgtcactt tattgtgaag atagtggaaa    360

aggaaggtgg ctcctacaaa tgccatcatt gcgataaagg aaaggccatc gttgaagatg    420

cctctgccga cagtggtccc aaagatggac ccccacccac gaggagcatc gtggaaaaag    480

aagacgttcc aaccacgtct tcaaagcaag tggattgatg tgatatctcc actgacgtaa    540

gggatgacgc acaatcccac tatccttcgc aagacccttc ctctatataa ggaagttcat    600

ttcatttgga gaggacacgc tgacaagctg actctagcag atcctctaga accatcttcc    660

acacactcaa gccacactat tggagaacac acagggacaa cacaccataa gatccaaggg    720

aggcctccgc cgccgccggt aaccaccccg cccctctcct ctttctttct ccgttttttt    780

ttccgtctcg gtctcgatct ttggccttgg tagtttgggt gggcgagagg cggcttcgtg    840

cgcgcccaga tcggtgcgcg ggaggggcgg gatctcgcgg ctggggctct cgccggcgtg    900

gatccggccc ggatctcgcg gggaatgggg ctctcggatg tagatctgcg atccgccgtt    960

gttgggggag atgatggggg gtttaaaatt tccgccgtgc taaacaagat caggaagagg   1020

ggaaaagggc actatggttt atatttttat atatttctgc tgcttcgtca ggcttagatg   1080

tgctagatct ttctttcttc tttttgtggg tagaatttga atccctcagc attgttcatc   1140

ggtagttttt cttttcatga tttgtgacaa atgcagcctc gtgcggagct tttttgtagg   1200

tagaagtgat caacctctag aggatcagca tggcgcccac cgtgatgatg gcctcgtcgg   1260

ccaccgccgt cgctccgttc ctggggctca agtccaccgc cagcctcccc gtcgcccgcc   1320

gctcctccag aagcctcggc aacgtcagca acggcggaag gatccggtgc atgcaggtaa   1380

caaatgcatc ctagctagta gttctttgca ttgcagcagc tgcagctagc gagttagtaa   1440

taggaaggga actgatgatc catgcatgga ctgatgtgtg ttgcccatcc catcccatcc   1500

catttcccaa acgaaccgaa aacaccgtac tacgtgcagg tgtggcccta cggcaacaag   1560

aagttcgaga cgctgtcgta cctgccgccg ctgtcgaccg gcgggcgcat ccgctgcatg   1620

caggcc atg gcc ttc ttc aac cgg gtg atc acc ctc acg gtg ccg tcg      1668
       Met Ala Phe Phe Asn Arg Val Ile Thr Leu Thr Val Pro Ser
       1               5                   10

tca gac gtg gtc aac tac tcg gag atc tac cag gtg gct cct cag tat     1716
Ser Asp Val Val Asn Tyr Ser Glu Ile Tyr Gln Val Ala Pro Gln Tyr
15                  20                  25                  30

gtc aac cag gcc ctg acc ctg gcc aag tac ttc cag ggc gcc atc gac     1764
Val Asn Gln Ala Leu Thr Leu Ala Lys Tyr Phe Gln Gly Ala Ile Asp
                35                  40                  45

ggc agc acc ctg agg ttc gac ttc gag aag gcg tta cag atc gcc aac     1812
Gly Ser Thr Leu Arg Phe Asp Phe Glu Lys Ala Leu Gln Ile Ala Asn
            50                  55                  60

gac atc ccg cag gcc gcg gtg gtc aac acc ctg aac cag acc gtc cag     1860
Asp Ile Pro Gln Ala Ala Val Val Asn Thr Leu Asn Gln Thr Val Gln
        65                  70                  75

cag ggg acc gtc cag gtc agc gtc atg atc gac aag atc gtg gac atc     1908
Gln Gly Thr Val Gln Val Ser Val Met Ile Asp Lys Ile Val Asp Ile
    80                  85                  90

atg aag aat gtc ctg tcc atc gtg ata gac aac aag aag ttt tgg gat     1956
Met Lys Asn Val Leu Ser Ile Val Ile Asp Asn Lys Lys Phe Trp Asp
95                  100                 105                 110

cag gtc acg gct gcc atc acc aac acc ttc acg aac ctg aac agc cag     2004
Gln Val Thr Ala Ala Ile Thr Asn Thr Phe Thr Asn Leu Asn Ser Gln
                115                 120                 125

gag tcg gag gcc tgg atc ttc tat tac aag gag gac gcc cac aag acg     2052
Glu Ser Glu Ala Trp Ile Phe Tyr Tyr Lys Glu Asp Ala His Lys Thr
            130                 135                 140
```

```
tcc tac tat tac aac atc ctc ttc gcc atc cag gac gaa gag acg ggt      2100
Ser Tyr Tyr Tyr Asn Ile Leu Phe Ala Ile Gln Asp Glu Glu Thr Gly
        145                 150                 155

ggc gtg atg gcc acg ctg ccc atc gcc ttc gac atc agt gtg gac atc      2148
Gly Val Met Ala Thr Leu Pro Ile Ala Phe Asp Ile Ser Val Asp Ile
    160                 165                 170

gag aag gag aag gtc ctg ttc gtg acc atc aag gac act gag aat tac      2196
Glu Lys Glu Lys Val Leu Phe Val Thr Ile Lys Asp Thr Glu Asn Tyr
175                 180                 185                 190

gcc gtc acc gtc aag gcg atc aac gtg gtc cag gca ctc cag tct agc      2244
Ala Val Thr Val Lys Ala Ile Asn Val Val Gln Ala Leu Gln Ser Ser
                195                 200                 205

agg gat tct aag gtg gtt gat gcg ttc aaa tcg cca cgg cac tta ccc      2292
Arg Asp Ser Lys Val Val Asp Ala Phe Lys Ser Pro Arg His Leu Pro
            210                 215                 220

cgg aag agg cat aag att tgc tct aac tcg tga tga attctgcatg          2338
Arg Lys Arg His Lys Ile Cys Ser Asn Ser
        225                 230

cgtttggacg tatgctcatt caggttggag ccaatttggt tgatgtgtgt gcgagttctt   2398

gcgagtctga tgagacatct ctgtattgtg tttctttccc cagtgttttc tgtacttgtg   2458

taatcggcta atcgccaaca gattcggcga tgaataaatg agaaataaat tgttctgatt   2518

ttgagtgcaa aaaaaaagga att                                            2541


<210> SEQ ID NO 37
<211> LENGTH: 232
<212> TYPE: PRT
<213> ORGANISM: Artificial Seqeuence
<220> FEATURE:
<223> OTHER INFORMATION: Synthetic Construct

<400> SEQUENCE: 37

Met Ala Phe Phe Asn Arg Val Ile Thr Leu Thr Val Pro Ser Ser Asp
1               5                   10                  15

Val Val Asn Tyr Ser Glu Ile Tyr Gln Val Ala Pro Gln Tyr Val Asn
            20                  25                  30

Gln Ala Leu Thr Leu Ala Lys Tyr Phe Gln Gly Ala Ile Asp Gly Ser
        35                  40                  45

Thr Leu Arg Phe Asp Phe Glu Lys Ala Leu Gln Ile Ala Asn Asp Ile
    50                  55                  60

Pro Gln Ala Ala Val Val Asn Thr Leu Asn Gln Thr Val Gln Gln Gly
65                  70                  75                  80

Thr Val Gln Val Ser Val Met Ile Asp Lys Ile Val Asp Ile Met Lys
                85                  90                  95

Asn Val Leu Ser Ile Val Ile Asp Asn Lys Lys Phe Trp Asp Gln Val
            100                 105                 110

Thr Ala Ala Ile Thr Asn Thr Phe Thr Asn Leu Asn Ser Gln Glu Ser
        115                 120                 125

Glu Ala Trp Ile Phe Tyr Tyr Lys Glu Asp Ala His Lys Thr Ser Tyr
    130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
            180                 185                 190
```

-continued

```
Thr Val Lys Ala Ile Asn Val Val Gln Ala Leu Gln Ser Ser Arg Asp
        195                 200                 205

Ser Lys Val Val Asp Ala Phe Lys Ser Pro Arg His Leu Pro Arg Lys
    210                 215                 220

Arg His Lys Ile Cys Ser Asn Ser
225                 230


<210> SEQ ID NO 38
<211> LENGTH: 4083
<212> TYPE: DNA
<213> ORGANISM: Artificial Sequence
<220> FEATURE:
<223> OTHER INFORMATION: synthetic sequence; expression cassette in
      pMON64144 encoding TIC809
<220> FEATURE:
<221> NAME/KEY: misc_feature
<223> OTHER INFORMATION: pMON64144 plant expression cassette
<220> FEATURE:
<221> NAME/KEY: promoter
<222> LOCATION: (1)..(1844)
<223> OTHER INFORMATION: rice Rcc3
<220> FEATURE:
<221> NAME/KEY: 5'UTR
<222> LOCATION: (1845)..(1943)
<223> OTHER INFORMATION: rice Rcc3
<220> FEATURE:
<221> NAME/KEY: Intron
<222> LOCATION: (1952)..(2755)
<223> OTHER INFORMATION: HSP70
<220> FEATURE:
<221> NAME/KEY: transit_peptide
<222> LOCATION: (2772)..(2912)
<223> OTHER INFORMATION: Zm RbcS
<220> FEATURE:
<221> NAME/KEY: Intron
<222> LOCATION: (2913)..(3081)
<223> OTHER INFORMATION: Zm RbcS
<220> FEATURE:
<221> NAME/KEY: transit_peptide
<222> LOCATION: (3082)..(3168)
<223> OTHER INFORMATION: Zm RbcS
<220> FEATURE:
<221> NAME/KEY: CDS
<222> LOCATION: (3169)..(3870)
<223> OTHER INFORMATION: TIC809
<220> FEATURE:
<221> NAME/KEY: terminator
<222> LOCATION: (3874)..(4083)
<223> OTHER INFORMATION: Wheat Hsp17

<400> SEQUENCE: 38

gcaatcaacc aacatatact gaatatggga aagtttcttt tagcttttct aaattaagta     60

ctgattctta aacttaagtg agaatctagc ctgttcaggg gcgacggcta aaggacatag    120

caccactagt ctacgcgatt gcaaaaaaga agaatgcaag cctgcaacaa gtatcgcttt    180

cccgaccaat ggttggttga cctcggtttg ccggtaacct caggctggac gacagaacta    240

attagccaac ttgtcaatgt ctagggtgct gttcatagcc tgcagttgac agagtacgaa    300

aaggacaaga tcacatggaa gctaactagt cacggcgaat acatgacgac atcggcctac    360

aacgcacaac ttcttggcat aaaagcttca atttcaatgc ccctatctgg aagccctagg    420

cgccgcgcaa atgtaaaaca ttcgcttcgc ttggcttgtt atccaaaata gagtatggac    480

ctccgacaga ttggcaaccc gtgggtaatc gaaaatggct ccatctgccc ctttgtcgaa    540

ggaatcagga aacggccctc acctcctggc ggagtgtaga tatgtgaaag aatctaggcg    600

acacttgcag actggacaac atgtgaacaa ataagaccaa cgttatggca acaagcctcg    660

acgctactca agtggtggga ggccaccgca tgttccaacg aagcgccaaa gaaagccttg    720
```

-continued

```
cagactctaa tgctattagt cgcctaggat atttggaatg aaaggaaccg cagagttttt    780
cagcaccaag agcttccggt ggctagtctg atagccaaaa ttaaggagga tgccaaaaca    840
tgggtcttgg cgggcgcgaa acaccttgat aggtggctta ccttttaaca tgttcgggcc    900
aaaggccttg agacggtaaa gttttctatt tgcgcttgcg catgtacaat tttattcctc    960
tattcaatga aattggtggc tcactggttc attaaaaaaa aaagaatcta gcctgttcgg   1020
gaagaagagg attttgttcg tgagagagag agagagagag agagagagag agagagagaa   1080
ggaggaggag gattttcagg cttcgcattg cccaacctct gcttctgttg gcccaagaag   1140
aatcccaggc gcccatgggc tggcagttta ccacggacct acctagccta ccttagctat   1200
ctaagcgggc cgacctagta gccacgtgcc tagtgtagat taaagttgcc gggccagcag   1260
gaagccacgc tgcaatggca tcttcccctg tccttcgcgt acgtgaaaac aaacccaggt   1320
aagcttagaa tcttcttgcc cgttggactg ggacacccac caatcccacc atgccccgat   1380
attcctccgg tctcggttca tgtgatgtcc tctcttgtgt gatcacggag caagcattct   1440
taaacggcaa aagaaaatca ccaacttgct cacgcagtca cgctgcaccg cgcgaagcga   1500
cgcccgatag gccaagatcg cgagataaaa taacaaccaa tgatcataag gaaacaagcc   1560
cgcgatgtgt cgtgtgcagc aatcttggtc atttgcggga tcgagtgctt cacagctaac   1620
caaatattcg gccgatgatt taacacatta tcagcgtaga tgtacgtacg atttgttaat   1680
taatctacga gccttgctag ggcaggtgtt ctgccagcca atccagatcg ccctcgtatg   1740
cacgctcaca tgatggcagg gcagggttca catgagctct aacggtcgat taattaatcc   1800
cggggctcga ctataaatac ctccctaatc ccatgatcaa aaccatctca agcagcctaa   1860
tcatctccag ctgatcaaga gctcttaatt agctagctag tgattagctg cgcttgtgat   1920
cgatcgatct cgggtacgta gcaatagatc taccgtcttc ggtacgcgct cactccgccc   1980
tctgcctttg ttactgccac gtttctctga atgctctctt gtgtggtgat tgctgagagt   2040
ggtttagctg gatctagaat tacactctga aatcgtgttc tgcctgtgct gattacttgc   2100
cgtcctttgt agcagcaaaa tatagggaca tggtagtacg aaacgaagat agaacctaca   2160
cagcaatacg agaaatgtgt aatttggtgc ttagcggtat ttatttaagc acatgttggt   2220
gttatagggc acttggattc agaagtttgc tgttaattta ggcacaggct tcatactaca   2280
tgggtcaata gtatagggat tcatattata ggcgatacta taataatttg ttcgtctgca   2340
gagcttatta tttgccaaaa ttagatattc ctattctgtt tttgtttgtg tgctgttaaa   2400
ttgttaacgc ctgaaggaat aaatataaat gacgaaattt tgatgtttat ctctgctcct   2460
ttattgtgac cataagtcaa gatcagatgc acttgtttta aatattgttg tctgaagaaa   2520
taagtactga cagtattttg atgcattgat ctgcttgttt gttgtaacaa aatttaaaaa   2580
taaagagttt ccttttttgtt gctctcctta cctcctgatg gtatctagta tctaccaact   2640
gacactatat tgcttctctt tacatacgta tcttgctcga tgccttctcc ctagtgttga   2700
ccagtgttac tcacatagtc tttgctcatt tcattgtaat gcagatacca agcggcctct   2760
agaggatcag catggcgccc accgtgatga tggcctcgtc ggccaccgcc gtcgctccgt   2820
tcctggggct caagtccacc gccagcctcc ccgtcgcccg ccgctcctcc agaagcctcg   2880
gcaacgtcag caacggcgga aggatccggt gcatgcaggt aacaaatgca tcctagctag   2940
tagttctttg cattgcagca gctgcagcta gcgagttagt aataggaagg gaactgatga   3000
tccatgcatg gactgatgtg tgttgcccat cccatcccat cccatttccc aaacgaaccg   3060
aaaacaccgt actacgtgca ggtgtggccc tacggcaaca agaagttcga gacgctgtcg   3120
```

```
tacctgccgc cgctgtcgac cggcgggcgc atccgctgca tgcaggcc atg gcc ttc     3177
                                                     Met Ala Phe
                                                     1

ttc aac cgg gtg atc acc ctc acg gtg ccg tcg tca gac gtg gtc aac     3225
Phe Asn Arg Val Ile Thr Leu Thr Val Pro Ser Ser Asp Val Val Asn
    5                   10                  15

tac tcg gag atc tac cag gtg gct cct cag tat gtc aac cag gcc ctg     3273
Tyr Ser Glu Ile Tyr Gln Val Ala Pro Gln Tyr Val Asn Gln Ala Leu
20                  25                  30                  35

acc ctg gcc aag tac ttc cag ggc gcc atc gac ggc agc acc ctg agg     3321
Thr Leu Ala Lys Tyr Phe Gln Gly Ala Ile Asp Gly Ser Thr Leu Arg
                40                  45                  50

ttc gac ttc gag aag gcg tta cag atc gcc aac gac atc ccg cag gcc     3369
Phe Asp Phe Glu Lys Ala Leu Gln Ile Ala Asn Asp Ile Pro Gln Ala
            55                  60                  65

gcg gtg gtc aac acc ctg aac cag acc gtc cag cag ggg acc gtc cag     3417
Ala Val Val Asn Thr Leu Asn Gln Thr Val Gln Gln Gly Thr Val Gln
        70                  75                  80

gtc agc gtc atg atc gac aag atc gtg gac atc atg aag aat gtc ctg     3465
Val Ser Val Met Ile Asp Lys Ile Val Asp Ile Met Lys Asn Val Leu
    85                  90                  95

tcc atc gtg ata gac aac aag aag ttt tgg gat cag gtc acg gct gcc     3513
Ser Ile Val Ile Asp Asn Lys Lys Phe Trp Asp Gln Val Thr Ala Ala
100                 105                 110                 115

atc acc aac acc ttc acg aac ctg aac agc cag gag tcg gag gcc tgg     3561
Ile Thr Asn Thr Phe Thr Asn Leu Asn Ser Gln Glu Ser Glu Ala Trp
                120                 125                 130

atc ttc tat tac aag gag gac gcc cac aag acg tcc tac tat tac aac     3609
Ile Phe Tyr Tyr Lys Glu Asp Ala His Lys Thr Ser Tyr Tyr Tyr Asn
            135                 140                 145

atc ctc ttc gcc atc cag gac gaa gag acg ggt ggc gtg atg gcc acg     3657
Ile Leu Phe Ala Ile Gln Asp Glu Glu Thr Gly Gly Val Met Ala Thr
        150                 155                 160

ctg ccc atc gcc ttc gac atc agt gtg gac atc gag aag gag aag gtc     3705
Leu Pro Ile Ala Phe Asp Ile Ser Val Asp Ile Glu Lys Glu Lys Val
    165                 170                 175

ctg ttc gtg acc atc aag gac act gag aat tac gcc gtc acc gtc aag     3753
Leu Phe Val Thr Ile Lys Asp Thr Glu Asn Tyr Ala Val Thr Val Lys
180                 185                 190                 195

gcg atc aac gtg gtc cag gca ctc cag tct agc agg gat tct aag gtg     3801
Ala Ile Asn Val Val Gln Ala Leu Gln Ser Ser Arg Asp Ser Lys Val
                200                 205                 210

gtt gat gcg ttc aaa tcg cca cgg cac tta ccc cgg aag agg cat aag     3849
Val Asp Ala Phe Lys Ser Pro Arg His Leu Pro Arg Lys Arg His Lys
            215                 220                 225

att tgc tct aac tcg tga tga attctgcatg cgtttggacg tatgctcatt        3900
Ile Cys Ser Asn Ser
        230

caggttggag ccaatttggt tgatgtgtgt gcgagttctt gcgagtctga tgagacatct   3960

ctgtattgtg tttctttccc cagtgttttc tgtacttgtg taatcggcta atcgccaaca   4020

gattcggcga tgaataaatg agaaataaat tgttctgatt ttgagtgcaa aaaaaaagga   4080

att                                                                 4083
```

<210> SEQ ID NO 39
<211> LENGTH: 232
<212> TYPE: PRT
<213> ORGANISM: Artificial Sequence
<220> FEATURE:

<223> OTHER INFORMATION: Synthetic Construct

<400> SEQUENCE: 39

```
Met Ala Phe Phe Asn Arg Val Ile Thr Leu Thr Val Pro Ser Ser Asp
1               5                   10                  15

Val Val Asn Tyr Ser Glu Ile Tyr Gln Val Ala Pro Gln Tyr Val Asn
            20                  25                  30

Gln Ala Leu Thr Leu Ala Lys Tyr Phe Gln Gly Ala Ile Asp Gly Ser
        35                  40                  45

Thr Leu Arg Phe Asp Phe Glu Lys Ala Leu Gln Ile Ala Asn Asp Ile
    50                  55                  60

Pro Gln Ala Ala Val Val Asn Thr Leu Asn Gln Thr Val Gln Gln Gly
65                  70                  75                  80

Thr Val Gln Val Ser Val Met Ile Asp Lys Ile Val Asp Ile Met Lys
                85                  90                  95

Asn Val Leu Ser Ile Val Ile Asp Asn Lys Lys Phe Trp Asp Gln Val
            100                 105                 110

Thr Ala Ala Ile Thr Asn Thr Phe Thr Asn Leu Asn Ser Gln Glu Ser
        115                 120                 125

Glu Ala Trp Ile Phe Tyr Tyr Lys Glu Asp Ala His Lys Thr Ser Tyr
    130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
            180                 185                 190

Thr Val Lys Ala Ile Asn Val Val Gln Ala Leu Gln Ser Ser Arg Asp
        195                 200                 205

Ser Lys Val Val Asp Ala Phe Lys Ser Pro Arg His Leu Pro Arg Lys
    210                 215                 220

Arg His Lys Ile Cys Ser Asn Ser
225                 230
```

<210> SEQ ID NO 40
<211> LENGTH: 6641
<212> TYPE: DNA
<213> ORGANISM: Artificial Sequence
<220> FEATURE:
<223> OTHER INFORMATION: synthetic sequence; expression cassettes in pMON64150 encoding TIC809 and TIC810
<220> FEATURE:
<221> NAME/KEY: misc_feature
<223> OTHER INFORMATION: pMON64150 first and second plant expression cassettes
<220> FEATURE:
<221> NAME/KEY: promoter
<222> LOCATION: (1)..(1844)
<223> OTHER INFORMATION: rice Rcc3
<220> FEATURE:
<221> NAME/KEY: 5'UTR
<222> LOCATION: (1845)..(1943)
<223> OTHER INFORMATION: rice Rcc3 leader
<220> FEATURE:
<221> NAME/KEY: Intron
<222> LOCATION: (1952)..(2755)
<223> OTHER INFORMATION: HSP70 intron
<220> FEATURE:
<221> NAME/KEY: transit_peptide
<222> LOCATION: (2772)..(2912)
<223> OTHER INFORMATION: Zm RbcS
<220> FEATURE:
<221> NAME/KEY: Intron
<222> LOCATION: (2913)..(3081)
<223> OTHER INFORMATION: Zm RbcS
<220> FEATURE:
<221> NAME/KEY: transit_peptide
<222> LOCATION: (3082)..(3168)
<223> OTHER INFORMATION: Zm RbcS
<220> FEATURE:
<221> NAME/KEY: CDS
<222> LOCATION: (3169)..(3870)
<223> OTHER INFORMATION: TIC809
<220> FEATURE:
<221> NAME/KEY: terminator
<222> LOCATION: (3874)..(4083)
<223> OTHER INFORMATION: Wheat Hsp17
<220> FEATURE:
<221> NAME/KEY: promoter
<222> LOCATION: (4139)..(4750)
<223> OTHER INFORMATION: e35S
<220> FEATURE:
<221> NAME/KEY: 5'UTR
<222> LOCATION: (4751)..(4759)
<223> OTHER INFORMATION: leader
<220> FEATURE:
<221> NAME/KEY: 5'UTR
<222> LOCATION: (4786)..(4846)
<223> OTHER INFORMATION: lWheat CAB leader
<220> FEATURE:
<221> NAME/KEY: Intron
<222> LOCATION: (4863)..(5342)
<223> OTHER INFORMATION: rice actin
<220> FEATURE:
<221> NAME/KEY: transit_peptide
<222> LOCATION: (5366)..(5506)
<223> OTHER INFORMATION: Zm.RbcS
<220> FEATURE:
<221> NAME/KEY: Intron
<222> LOCATION: (5507)..(5676)
<223> OTHER INFORMATION: Zm.RbcS
<220> FEATURE:
<221> NAME/KEY: transit_peptide
<222> LOCATION: (5677)..(5766)
<223> OTHER INFORMATION: Zm RbcS
<220> FEATURE:
<221> NAME/KEY: CDS
<222> LOCATION: (5767)..(6426)
<223> OTHER INFORMATION: TIC810
<220> FEATURE:
<221> NAME/KEY: terminator
<222> LOCATION: (6432)..(6641)
<223> OTHER INFORMATION: Wheat Hsp17

<400> SEQUENCE: 40
gcaatcaacc aacatatact gaatatggga aagtttcttt tagcttttct aaattaagta 60
ctgattctta aacttaagtg agaatctagc ctgttcaggg gcgacggcta aaggacatag 120
caccactagt ctacgcgatt gcaaaaaaga agaatgcaag cctgcaacaa gtatcgcttt 180
cccgaccaat ggttggttga cctcggtttg ccggtaacct caggctggac gacagaacta 240
attagccaac ttgtcaatgt ctagggtgct gttcatagcc tgcagttgac agagtacgaa 300
aaggacaaga tcacatggaa gctaactagt cacggcgaat acatgacgac atcggcctac 360
aacgcacaac ttcttggcat aaaagcttca atttcaatgc ccctatctgg aagccctagg 420
cgccgcgcaa atgtaaaaca ttcgcttcgc ttggcttgtt atccaaaata gagtatggac 480
ctccgacaga ttggcaaccc gtgggtaatc gaaaatggct ccatctgccc ctttgtcgaa 540
ggaatcagga aacggccctc acctcctggc ggagtgtaga tatgtgaaag aatctaggcg 600
acacttgcag actggacaac atgtgaacaa ataagaccaa cgttatggca acaagcctcg 660
acgctactca agtggtggga ggccaccgca tgttccaacg aagcgccaaa gaaagccttg 720
cagactctaa tgctattagt cgcctaggat atttggaatg aaaggaaccg cagagttttt 780

-continued

```
cagcaccaag agcttccggt ggctagtctg atagccaaaa ttaaggagga tgccaaaaca    840
tgggtcttgg cgggcgcgaa acaccttgat aggtggctta ccttttaaca tgttcgggcc    900
aaaggccttg agacggtaaa gttttctatt tgcgcttgcg catgtacaat tttattcctc    960
tattcaatga aattggtggc tcactggttc attaaaaaaa aaagaatcta gcctgttcgg   1020
gaagaagagg attttgttcg tgagagagag agagagagag agagagagag agagagagaa   1080
ggaggaggag gattttcagg cttcgcattg cccaacctct gcttctgttg gcccaagaag   1140
aatcccaggc gcccatgggc tggcagttta ccacggacct acctagccta ccttagctat   1200
ctaagcgggc cgacctagta gccacgtgcc tagtgtagat taaagttgcc gggccagcag   1260
gaagccacgc tgcaatggca tcttcccctg tccttcgcgt acgtgaaaac aaacccaggt   1320
aagcttagaa tcttcttgcc cgttggactg ggacacccac caatcccacc atgccccgat   1380
attcctccgg tctcggttca tgtgatgtcc tctcttgtgt gatcacggag caagcattct   1440
taaacggcaa aagaaaatca ccaacttgct cacgcagtca cgctgcaccg cgcgaagcga   1500
cgcccgatag gccaagatcg cgagataaaa taacaaccaa tgatcataag gaaacaagcc   1560
cgcgatgtgt cgtgtgcagc aatcttggtc atttgcggga tcgagtgctt cacagctaac   1620
caaatattcg gccgatgatt taacacatta tcagcgtaga tgtacgtacg atttgttaat   1680
taatctacga gccttgctag ggcaggtgtt ctgccagcca atccagatcg ccctcgtatg   1740
cacgctcaca tgatggcagg gcagggttca catgagctct aacggtcgat taattaatcc   1800
cggggctcga ctataaatac ctccctaatc ccatgatcaa aaccatctca agcagcctaa   1860
tcatctccag ctgatcaaga gctcttaatt agctagctag tgattagctg cgcttgtgat   1920
cgatcgatct cgggtacgta gcaatagatc taccgtcttc ggtacgcgct cactccgccc   1980
tctgcctttg ttactgccac gtttctctga atgctctctt gtgtggtgat tgctgagagt   2040
ggtttagctg gatctagaat tacactctga aatcgtgttc tgcctgtgct gattacttgc   2100
cgtcctttgt agcagcaaaa tatagggaca tggtagtacg aaacgaagat agaacctaca   2160
cagcaatacg agaaatgtgt aatttggtgc ttagcggtat ttatttaagc acatgttggt   2220
gttatagggc acttggattc agaagtttgc tgttaattta ggcacaggct tcatactaca   2280
tgggtcaata gtatagggat tcatattata ggcgatacta taataatttg ttcgtctgca   2340
gagcttatta tttgccaaaa ttagatattc ctattctgtt tttgtttgtg tgctgttaaa   2400
ttgttaacgc ctgaaggaat aaatataaat gacgaaattt tgatgtttat ctctgctcct   2460
ttattgtgac cataagtcaa gatcagatgc acttgtttta aatattgttg tctgaagaaa   2520
taagtactga cagtattttg atgcattgat ctgcttgttt gttgtaacaa aatttaaaaa   2580
taaagagttt cctttttgtt gctctcctta cctcctgatg gtatctagta tctaccaact   2640
gacactatat tgcttctctt tacatacgta tcttgctcga tgccttctcc ctagtgttga   2700
ccagtgttac tcacatagtc tttgctcatt tcattgtaat gcagatacca agcggcctct   2760
agaggatcag catggcgccc accgtgatga tggcctcgtc ggccaccgcc gtcgctccgt   2820
tcctggggct caagtccacc gccagcctcc ccgtcgcccg ccgctcctcc agaagcctcg   2880
gcaacgtcag caacggcgga aggatccggt gcatgcaggt aacaaatgca tcctagctag   2940
tagttctttg cattgcagca gctgcagcta gcgagttagt aataggaagg gaactgatga   3000
tccatgcatg gactgatgtg tgttgcccat cccatcccat cccatttccc aaacgaaccg   3060
aaaacaccgt actacgtgca ggtgtggccc tacggcaaca agaagttcga gacgctgtcg   3120
tacctgccgc cgctgtcgac cggcgggcgc atccgctgca tgcaggcc atg gcc ttc    3177
```

```
                                                     Met Ala Phe
                                                     1

ttc aac cgg gtg atc acc ctc acg gtg ccg tcg tca gac gtg gtc aac     3225
Phe Asn Arg Val Ile Thr Leu Thr Val Pro Ser Ser Asp Val Val Asn
    5                   10                  15

tac tcg gag atc tac cag gtg gct cct cag tat gtc aac cag gcc ctg     3273
Tyr Ser Glu Ile Tyr Gln Val Ala Pro Gln Tyr Val Asn Gln Ala Leu
20                  25                  30                  35

acc ctg gcc aag tac ttc cag ggc gcc atc gac ggc agc acc ctg agg     3321
Thr Leu Ala Lys Tyr Phe Gln Gly Ala Ile Asp Gly Ser Thr Leu Arg
                40                  45                  50

ttc gac ttc gag aag gcg tta cag atc gcc aac gac atc ccg cag gcc     3369
Phe Asp Phe Glu Lys Ala Leu Gln Ile Ala Asn Asp Ile Pro Gln Ala
            55                  60                  65

gcg gtg gtc aac acc ctg aac cag acc gtc cag cag ggg acc gtc cag     3417
Ala Val Val Asn Thr Leu Asn Gln Thr Val Gln Gln Gly Thr Val Gln
        70                  75                  80

gtc agc gtc atg atc gac aag atc gtg gac atc atg aag aat gtc ctg     3465
Val Ser Val Met Ile Asp Lys Ile Val Asp Ile Met Lys Asn Val Leu
    85                  90                  95

tcc atc gtg ata gac aac aag aag ttt tgg gat cag gtc acg gct gcc     3513
Ser Ile Val Ile Asp Asn Lys Lys Phe Trp Asp Gln Val Thr Ala Ala
100                 105                 110                 115

atc acc aac acc ttc acg aac ctg aac agc cag gag tcg gag gcc tgg     3561
Ile Thr Asn Thr Phe Thr Asn Leu Asn Ser Gln Glu Ser Glu Ala Trp
                120                 125                 130

atc ttc tat tac aag gag gac gcc cac aag acg tcc tac tat tac aac     3609
Ile Phe Tyr Tyr Lys Glu Asp Ala His Lys Thr Ser Tyr Tyr Tyr Asn
            135                 140                 145

atc ctc ttc gcc atc cag gac gaa gag acg ggt ggc gtg atg gcc acg     3657
Ile Leu Phe Ala Ile Gln Asp Glu Glu Thr Gly Gly Val Met Ala Thr
        150                 155                 160

ctg ccc atc gcc ttc gac atc agt gtg gac atc gag aag gag aag gtc     3705
Leu Pro Ile Ala Phe Asp Ile Ser Val Asp Ile Glu Lys Glu Lys Val
    165                 170                 175

ctg ttc gtg acc atc aag gac act gag aat tac gcc gtc acc gtc aag     3753
Leu Phe Val Thr Ile Lys Asp Thr Glu Asn Tyr Ala Val Thr Val Lys
180                 185                 190                 195

gcg atc aac gtg gtc cag gca ctc cag tct agc agg gat tct aag gtg     3801
Ala Ile Asn Val Val Gln Ala Leu Gln Ser Ser Arg Asp Ser Lys Val
                200                 205                 210

gtt gat gcg ttc aaa tcg cca cgg cac tta ccc cgg aag agg cat aag     3849
Val Asp Ala Phe Lys Ser Pro Arg His Leu Pro Arg Lys Arg His Lys
            215                 220                 225

att tgc tct aac tcg tga tga attctgcatg cgtttggacg tatgctcatt        3900
Ile Cys Ser Asn Ser
        230

caggttggag ccaatttggt tgatgtgtgt gcgagttctt gcgagtctga tgagacatct   3960

ctgtattgtg tttctttccc cagtgttttc tgtacttgtg taatcggcta atcgccaaca   4020

gattcggcga tgaataaatg agaaataaat tgttctgatt ttgagtgcaa aaaaaaagga   4080

attagatctg tgtgtgtttt ttggatcccc ggggcggccg cgttaacaag cttctgcagg   4140

tccgattgag acttttcaac aaagggtaat atccggaaac ctcctcggat tccattgccc   4200

agctatctgt cactttattg tgaagatagt ggaaaaggaa ggtggctcct acaaatgcca   4260

tcattgcgat aaaggaaagg ccatcgttga agatgcctct gccgacagtg gtcccaaaga   4320

tggaccccca cccacgagga gcatcgtgga aaaagaagac gttccaacca cgtcttcaaa   4380
```

-continued

```
gcaagtggat tgatgtgatg gtccgattga gacttttcaa caaagggtaa tatccggaaa   4440

cctcctcgga ttccattgcc cagctatctg tcactttatt gtgaagatag tggaaaagga   4500

aggtggctcc tacaaatgcc atcattgcga taaaggaaag gccatcgttg aagatgcctc   4560

tgccgacagt ggtcccaaag atggaccccc acccacgagg agcatcgtgg aaaaagaaga   4620

cgttccaacc acgtcttcaa agcaagtgga ttgatgtgat atctccactg acgtaaggga   4680

tgacgcacaa tcccactatc cttcgcaaga cccttcctct atataaggaa gttcatttca   4740

tttggagagg acacgctgac aagctgactc tagcagatcc tctagaacca tcttccacac   4800

actcaagcca cactattgga gaacacacag ggacaacaca ccataagatc caagggaggc   4860

ctccgccgcc gccggtaacc accccgcccc tctcctcttt ctttctccgt ttttttttcc   4920

gtctcggtct cgatctttgg ccttggtagt ttgggtgggc gagaggcggc ttcgtgcgcg   4980

cccagatcgg tgcgcgggag gggcgggatc tcgcggctgg ggctctcgcc ggcgtggatc   5040

cggcccggat ctcgcgggga atggggctct cggatgtaga tctgcgatcc gccgttgttg   5100

ggggagatga tggggggttt aaaatttccg ccgtgctaaa caagatcagg aagaggggaa   5160

aagggcacta tggtttatat ttttatatat ttctgctgct tcgtcaggct tagatgtgct   5220

agatctttct ttcttctttt tgtgggtaga atttgaatcc ctcagcattg ttcatcggta   5280

gtttttcttt tcatgatttg tgacaaatgc agcctcgtgc ggagcttttt tgtaggtaga   5340

agtgatcaac ctctagagga tcagcatggc gcccaccgtg atgatggcct cgtcggccac   5400

cgccgtcgct ccgttccagg ggctcaagtc caccgccagc ctccccgtcg cccgccgctc   5460

ctccagaagc ctcggcaacg tcagcaacgg cggaaggatc cggtgcatgc aggtaacaaa   5520

tgcatcctag ctagtagttc tttgcattgc agcagctgca gctagcgagt tagtaatagg   5580

aagggaactg atgatccatg catggactga tgtgtgttgc ccatcccatc ccatttccca   5640

accccaaacg aaccaaaaca cacgtactac gtgcaggtgt ggccggccta cggcaacaag   5700

aagttcgaga cgctgtcgta cctgccgccg ctgtcgaccg gcgggcgcat ccgctgcatg   5760

caggcc atg agc aaa gaa atc agg ctc aac ctt tct cgt gag agc ggc      5808
       Met Ser Lys Glu Ile Arg Leu Asn Leu Ser Arg Glu Ser Gly
               235                 240                 245

gcc gac ctg tac ctc aag atc ctc gcc ttc gtg aag ccc gag cac ttc     5856
Ala Asp Leu Tyr Leu Lys Ile Leu Ala Phe Val Lys Pro Glu His Phe
            250                 255                 260

ttt cag gcg tac ctc ctg tgc cgc gag ttc gag agc atc gtg gat cct     5904
Phe Gln Ala Tyr Leu Leu Cys Arg Glu Phe Glu Ser Ile Val Asp Pro
        265                 270                 275

aca acc cgc gag tct gac ttc gac aag acg ctg acc atc gtg aag tcg     5952
Thr Thr Arg Glu Ser Asp Phe Asp Lys Thr Leu Thr Ile Val Lys Ser
    280                 285                 290

gac tcc acc ctc gtg acc gtg ggc acg atg aac acc aag ctg gtc aat     6000
Asp Ser Thr Leu Val Thr Val Gly Thr Met Asn Thr Lys Leu Val Asn
295                 300                 305                 310

agc caa gag atc ctc gtg tcg gac ttg atc act caa gtc ggt tcc cag     6048
Ser Gln Glu Ile Leu Val Ser Asp Leu Ile Thr Gln Val Gly Ser Gln
                315                 320                 325

atc gcc gat acc ctc ggc atc acg gac atc gac gcc aac acc cag caa     6096
Ile Ala Asp Thr Leu Gly Ile Thr Asp Ile Asp Ala Asn Thr Gln Gln
            330                 335                 340

cag ctc acg gag ctg atc ggc aac ctc ttc gtg aac ctc aat tcc caa     6144
Gln Leu Thr Glu Leu Ile Gly Asn Leu Phe Val Asn Leu Asn Ser Gln
        345                 350                 355

gtt cag gag tac atc tac ttc tac gag gag aag gag aag cag acc tcc     6192
```

-continued

```
Val Gln Glu Tyr Ile Tyr Phe Tyr Glu Glu Lys Glu Lys Gln Thr Ser
    360                 365                 370

tac cgc tac aac atc ctc ttc gtg ttc gaa aag gag tcg ttc atc acc     6240
Tyr Arg Tyr Asn Ile Leu Phe Val Phe Glu Lys Glu Ser Phe Ile Thr
375                 380                 385                 390

att ctg cca atg ggc ttc gac gtg acc gtg aac acg aac aag gag gcc     6288
Ile Leu Pro Met Gly Phe Asp Val Thr Val Asn Thr Asn Lys Glu Ala
                395                 400                 405

gtc ctg aag ctg acc ccg aag gac aag gtt acc tac ggc cac gtc agc     6336
Val Leu Lys Leu Thr Pro Lys Asp Lys Val Thr Tyr Gly His Val Ser
            410                 415                 420

gtc aag gcc ctc aac atc atc cag ctc att acg gag gac aag ttc aac     6384
Val Lys Ala Leu Asn Ile Ile Gln Leu Ile Thr Glu Asp Lys Phe Asn
        425                 430                 435

ttc ctc gca acc ctc aag aag gct ctc aag acc ctg tga tga             6426
Phe Leu Ala Thr Leu Lys Lys Ala Leu Lys Thr Leu
    440                 445                 450

gaattctgca tgcgtttgga cgtatgctca ttcaggttgg agccaatttg gttgatgtgt   6486

gtgcgagttc ttgcgagtct gatgagacat ctctgtattg tgtttctttc cccagtgttt   6546

tctgtacttg tgtaatcggc taatcgccaa cagattcggc gatgaataaa tgagaaataa   6606

attgttctga ttttgagtgc aaaaaaaaag gaatt                              6641


<210> SEQ ID NO 41
<211> LENGTH: 232
<212> TYPE: PRT
<213> ORGANISM: Artificial Sequence
<220> FEATURE:
<223> OTHER INFORMATION: Synthetic Construct

<400> SEQUENCE: 41

Met Ala Phe Phe Asn Arg Val Ile Thr Leu Thr Val Pro Ser Ser Asp
1               5                   10                  15

Val Val Asn Tyr Ser Glu Ile Tyr Gln Val Ala Pro Gln Tyr Val Asn
            20                  25                  30

Gln Ala Leu Thr Leu Ala Lys Tyr Phe Gln Gly Ala Ile Asp Gly Ser
        35                  40                  45

Thr Leu Arg Phe Asp Phe Glu Lys Ala Leu Gln Ile Ala Asn Asp Ile
    50                  55                  60

Pro Gln Ala Ala Val Val Asn Thr Leu Asn Gln Thr Val Gln Gln Gly
65                  70                  75                  80

Thr Val Gln Val Ser Val Met Ile Asp Lys Ile Val Asp Ile Met Lys
                85                  90                  95

Asn Val Leu Ser Ile Val Ile Asp Asn Lys Lys Phe Trp Asp Gln Val
            100                 105                 110

Thr Ala Ala Ile Thr Asn Thr Phe Thr Asn Leu Asn Ser Gln Glu Ser
        115                 120                 125

Glu Ala Trp Ile Phe Tyr Tyr Lys Glu Asp Ala His Lys Thr Ser Tyr
    130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
            180                 185                 190

Thr Val Lys Ala Ile Asn Val Val Gln Ala Leu Gln Ser Ser Arg Asp
        195                 200                 205
```

```
Ser Lys Val Val Asp Ala Phe Lys Ser Pro Arg His Leu Pro Arg Lys
    210                 215                 220

Arg His Lys Ile Cys Ser Asn Ser
225                 230
```

<210> SEQ ID NO 42
<211> LENGTH: 218
<212> TYPE: PRT
<213> ORGANISM: Artificial Sequence
<220> FEATURE:
<223> OTHER INFORMATION: Synthetic Construct

<400> SEQUENCE: 42

```
Met Ser Lys Glu Ile Arg Leu Asn Leu Ser Arg Glu Ser Gly Ala Asp
1               5                   10                  15

Leu Tyr Leu Lys Ile Leu Ala Phe Val Lys Pro Glu His Phe Phe Gln
            20                  25                  30

Ala Tyr Leu Leu Cys Arg Glu Phe Glu Ser Ile Val Asp Pro Thr Thr
        35                  40                  45

Arg Glu Ser Asp Phe Asp Lys Thr Leu Thr Ile Val Lys Ser Asp Ser
    50                  55                  60

Thr Leu Val Thr Val Gly Thr Met Asn Thr Lys Leu Val Asn Ser Gln
65                  70                  75                  80

Glu Ile Leu Val Ser Asp Leu Ile Thr Gln Val Gly Ser Gln Ile Ala
                85                  90                  95

Asp Thr Leu Gly Ile Thr Asp Ile Asp Ala Asn Thr Gln Gln Gln Leu
            100                 105                 110

Thr Glu Leu Ile Gly Asn Leu Phe Val Asn Leu Asn Ser Gln Val Gln
        115                 120                 125

Glu Tyr Ile Tyr Phe Tyr Glu Glu Lys Glu Lys Gln Thr Ser Tyr Arg
    130                 135                 140

Tyr Asn Ile Leu Phe Val Phe Glu Lys Glu Ser Phe Ile Thr Ile Leu
145                 150                 155                 160

Pro Met Gly Phe Asp Val Thr Val Asn Thr Asn Lys Glu Ala Val Leu
                165                 170                 175

Lys Leu Thr Pro Lys Asp Lys Val Thr Tyr Gly His Val Ser Val Lys
            180                 185                 190

Ala Leu Asn Ile Ile Gln Leu Ile Thr Glu Asp Lys Phe Asn Phe Leu
        195                 200                 205

Ala Thr Leu Lys Lys Ala Leu Lys Thr Leu
    210                 215
```

<210> SEQ ID NO 43
<211> LENGTH: 5813
<212> TYPE: DNA
<213> ORGANISM: Artificial Sequence
<220> FEATURE:
<223> OTHER INFORMATION: synthetic sequence; expression cassettes in
pMON64151 encoding TIC809 and TIC810
<220> FEATURE:
<221> NAME/KEY: misc_feature
<223> OTHER INFORMATION: pMON64151 first and second plant expression
cassettes
<220> FEATURE:
<221> NAME/KEY: promoter
<222> LOCATION: (1)..(1844)
<223> OTHER INFORMATION: rice Rcc3
<220> FEATURE:
<221> NAME/KEY: 5'UTR
<222> LOCATION: (1845)..(1943)
<223> OTHER INFORMATION: rice Rcc3 leader
<220> FEATURE:
<221> NAME/KEY: Intron
<222> LOCATION: (1952)..(2755)
<223> OTHER INFORMATION: HSP70 intron
<220> FEATURE:
<221> NAME/KEY: CDS
<222> LOCATION: (2772)..(3473)
<223> OTHER INFORMATION: TIC809
<220> FEATURE:
<221> NAME/KEY: terminator
<222> LOCATION: (3477)..(3686)
<223> OTHER INFORMATION: Wheat Hsp17
<220> FEATURE:
<221> NAME/KEY: promoter
<222> LOCATION: (3724)..(4337)
<223> OTHER INFORMATION: e35S
<220> FEATURE:
<221> NAME/KEY: 5'UTR
<222> LOCATION: (4373)..(4433)
<223> OTHER INFORMATION: Wheat CAB leader
<220> FEATURE:
<221> NAME/KEY: Intron
<222> LOCATION: (4450)..(4929)
<223> OTHER INFORMATION: rice actin
<220> FEATURE:
<221> NAME/KEY: CDS
<222> LOCATION: (4939)..(5598)
<223> OTHER INFORMATION: TIC810
<220> FEATURE:
<221> NAME/KEY: terminator
<222> LOCATION: (5604)..(5813)
<223> OTHER INFORMATION: Wheat Hsp17

<400> SEQUENCE: 43
gcaatcaacc aacatatact gaatatggga aagtttcttt tagcttttct aaattaagta 60
ctgattctta aacttaagtg agaatctagc ctgttcaggg gcgacggcta aaggacatag 120
caccactagt ctacgcgatt gcaaaaaaga agaatgcaag cctgcaacaa gtatcgcttt 180
cccgaccaat ggttggttga cctcggtttg ccggtaacct caggctggac gacagaacta 240
attagccaac ttgtcaatgt ctagggtgct gttcatagcc tgcagttgac agagtacgaa 300
aaggacaaga tcacatggaa gctaactagt cacggcgaat acatgacgac atcggcctac 360
aacgcacaac ttcttggcat aaaagcttca atttcaatgc ccctatctgg aagccctagg 420
cgccgcgcaa atgtaaaaca ttcgcttcgc ttggcttgtt atccaaaata gagtatggac 480
ctccgacaga ttggcaaccc gtgggtaatc gaaaatggct ccatctgccc ctttgtcgaa 540
ggaatcagga aacggccctc acctcctggc ggagtgtaga tatgtgaaag aatctaggcg 600
acacttgcag actggacaac atgtgaacaa ataagaccaa cgttatggca acaagcctcg 660
acgctactca agtggtggga ggccaccgca tgttccaacg aagcgccaaa gaaagccttg 720
cagactctaa tgctattagt cgcctaggat atttggaatg aaaggaaccg cagagttttt 780
cagcaccaag agcttccggt ggctagtctg atagccaaaa ttaaggagga tgccaaaaca 840
tgggtcttgg cgggcgcgaa acaccttgat aggtggctta ccttttaaca tgttcgggcc 900
aaaggccttg agacggtaaa gttttctatt tgcgcttgcg catgtacaat tttattcctc 960
tattcaatga aattggtggc tcactggttc attaaaaaaa aaagaatcta gcctgttcgg 1020
gaagaagagg attttgttcg tgagagagag agagagagag agagagagag agagagagaa 1080
ggaggaggag gattttcagg cttcgcattg cccaacctct gcttctgttg gcccaagaag 1140
aatcccaggc gcccatgggc tggcagttta ccacggacct acctagccta ccttagctat 1200
ctaagcgggc cgacctagta gccacgtgcc tagtgtagat taaagttgcc gggccagcag 1260
gaagccacgc tgcaatggca tcttcccctg tccttcgcgt acgtgaaaac aaacccaggt 1320

-continued

```
aagcttagaa tcttcttgcc cgttggactg ggacacccac caatcccacc atgccccgat   1380

attcctccgg tctcggttca tgtgatgtcc tctcttgtgt gatcacggag caagcattct   1440

taaacggcaa aagaaaatca ccaacttgct cacgcagtca cgctgcaccg cgcgaagcga   1500

cgcccgatag gccaagatcg cgagataaaa taacaaccaa tgatcataag gaaacaagcc   1560

cgcgatgtgt cgtgtgcagc aatcttggtc atttgcggga tcgagtgctt cacagctaac   1620

caaatattcg gccgatgatt taacacatta tcagcgtaga tgtacgtacg atttgttaat   1680

taatctacga gccttgctag ggcaggtgtt ctgccagcca atccagatcg ccctcgtatg   1740

cacgctcaca tgatggcagg gcagggttca catgagctct aacggtcgat taattaatcc   1800

cggggctcga ctataaatac ctccctaatc ccatgatcaa aaccatctca agcagcctaa   1860

tcatctccag ctgatcaaga gctcttaatt agctagctag tgattagctg cgcttgtgat   1920

cgatcgatct cgggtacgta gcaatagatc taccgtcttc ggtacgcgct cactccgccc   1980

tctgcctttg ttactgccac gtttctctga atgctctctt gtgtggtgat tgctgagagt   2040

ggtttagctg gatctagaat tacactctga aatcgtgttc tgcctgtgct gattacttgc   2100

cgtcctttgt agcagcaaaa tatagggaca tggtagtacg aaacgaagat agaacctaca   2160

cagcaatacg agaaatgtgt aatttggtgc ttagcggtat ttatttaagc acatgttggt   2220

gttatagggc acttggattc agaagtttgc tgttaattta ggcacaggct tcatactaca   2280

tgggtcaata gtatagggat tcatattata ggcgatacta taataatttg ttcgtctgca   2340

gagcttatta tttgccaaaa ttagatattc ctattctgtt tttgtttgtg tgctgttaaa   2400

ttgttaacgc ctgaaggaat aaatataaat gacgaaattt tgatgtttat ctctgctcct   2460

ttattgtgac cataagtcaa gatcagatgc acttgtttta aatattgttg tctgaagaaa   2520

taagtactga cagtattttg atgcattgat ctgcttgttt gttgtaacaa aatttaaaaa   2580

taaagagttt cctttttgtt gctctcctta cctcctgatg gtatctagta tctaccaact   2640

gacactatat tgcttctctt tacatacgta tcttgctcga tgccttctcc ctagtgttga   2700

ccagtgttac tcacatagtc tttgctcatt tcattgtaat gcagatacca agcggcctct   2760

agaggatctc c atg gcc ttc ttc aac cgg gtg atc acc ctc acg gtg ccg     2810
             Met Ala Phe Phe Asn Arg Val Ile Thr Leu Thr Val Pro
             1               5                   10

tcg tca gac gtg gtc aac tac tcg gag atc tac cag gtg gct cct cag      2858
Ser Ser Asp Val Val Asn Tyr Ser Glu Ile Tyr Gln Val Ala Pro Gln
    15                  20                  25

tat gtc aac cag gcc ctg acc ctg gcc aag tac ttc cag ggc gcc atc      2906
Tyr Val Asn Gln Ala Leu Thr Leu Ala Lys Tyr Phe Gln Gly Ala Ile
30                  35                  40                  45

gac ggc agc acc ctg agg ttc gac ttc gag aag gcg tta cag atc gcc      2954
Asp Gly Ser Thr Leu Arg Phe Asp Phe Glu Lys Ala Leu Gln Ile Ala
                50                  55                  60

aac gac atc ccg cag gcc gcg gtg gtc aac acc ctg aac cag acc gtc      3002
Asn Asp Ile Pro Gln Ala Ala Val Val Asn Thr Leu Asn Gln Thr Val
            65                  70                  75

cag cag ggg acc gtc cag gtc agc gtc atg atc gac aag atc gtg gac      3050
Gln Gln Gly Thr Val Gln Val Ser Val Met Ile Asp Lys Ile Val Asp
        80                  85                  90

atc atg aag aat gtc ctg tcc atc gtg ata gac aac aag aag ttt tgg      3098
Ile Met Lys Asn Val Leu Ser Ile Val Ile Asp Asn Lys Lys Phe Trp
    95                  100                 105

gat cag gtc acg gct gcc atc acc aac acc ttc acg aac ctg aac agc      3146
Asp Gln Val Thr Ala Ala Ile Thr Asn Thr Phe Thr Asn Leu Asn Ser
110                 115                 120                 125
```

-continued

```
cag gag tcg gag gcc tgg atc ttc tat tac aag gag gac gcc cac aag      3194
Gln Glu Ser Glu Ala Trp Ile Phe Tyr Tyr Lys Glu Asp Ala His Lys
                130                 135                 140

acg tcc tac tat tac aac atc ctc ttc gcc atc cag gac gaa gag acg      3242
Thr Ser Tyr Tyr Tyr Asn Ile Leu Phe Ala Ile Gln Asp Glu Glu Thr
            145                 150                 155

ggt ggc gtg atg gcc acg ctg ccc atc gcc ttc gac atc agt gtg gac      3290
Gly Gly Val Met Ala Thr Leu Pro Ile Ala Phe Asp Ile Ser Val Asp
        160                 165                 170

atc gag aag gag aag gtc ctg ttc gtg acc atc aag gac act gag aat      3338
Ile Glu Lys Glu Lys Val Leu Phe Val Thr Ile Lys Asp Thr Glu Asn
    175                 180                 185

tac gcc gtc acc gtc aag gcg atc aac gtg gtc cag gca ctc cag tct      3386
Tyr Ala Val Thr Val Lys Ala Ile Asn Val Val Gln Ala Leu Gln Ser
190                 195                 200                 205

agc agg gat tct aag gtg gtt gat gcg ttc aaa tcg cca cgg cac tta      3434
Ser Arg Asp Ser Lys Val Val Asp Ala Phe Lys Ser Pro Arg His Leu
                210                 215                 220

ccc cgg aag agg cat aag att tgc tct aac tcg tga tga attctgcatg      3483
Pro Arg Lys Arg His Lys Ile Cys Ser Asn Ser
            225                 230

cgtttggacg tatgctcatt caggttggag ccaatttggt tgatgtgtgt gcgagttctt   3543

gcgagtctga tgagacatct ctgtattgtg tttctttccc cagtgttttc tgtacttgtg   3603

taatcggcta atcgccaaca gattcggcga tgaataaatg agaaataaat tgttctgatt   3663

ttgagtgcaa aaaaaaagga attagatctg tgtgtgtttt ttggatcccc agcttctgca   3723

ggtccgatgt gagacttttc aacaaagggt aatatccgga aacctcctcg gattccattg   3783

cccagctatc tgtcacttta ttgtgaagat agtggaaaag gaaggtggct cctacaaatg   3843

ccatcattgc gataaaggaa aggccatcgt tgaagatgcc tctgccgaca gtggtcccaa   3903

agatggaccc ccacccacga ggagcatcgt ggaaaaagaa gacgttccaa ccacgtcttc   3963

aaagcaagtg gattgatgtg atggtccgat gtgagacttt tcaacaaagg gtaatatccg   4023

gaaacctcct cggattccat tgcccagcta tctgtcactt tattgtgaag atagtggaaa   4083

aggaaggtgg ctcctacaaa tgccatcatt gcgataaagg aaaggccatc gttgaagatg   4143

cctctgccga cagtggtccc aaagatggac ccccacccac gaggagcatc gtggaaaaag   4203

aagacgttcc aaccacgtct tcaaagcaag tggattgatg tgatatctcc actgacgtaa   4263

gggatgacgc acaatcccac tatccttcgc aagacccttc ctctatataa ggaagttcat   4323

ttcatttgga gaggacacgc tgacaagctg actctagcag atcctctaga accatcttcc   4383

acacactcaa gccacactat tggagaacac acagggacaa cacaccataa gatccaaggg   4443

aggcctccgc cgccgccggt aaccaccccg cccctctcct ctttctttct ccgttttttt   4503

ttccgtctcg gtctcgatct ttggccttgg tagtttgggt gggcgagagg cggcttcgtg   4563

cgcgcccaga tcggtgcgcg ggaggggcgg gatctcgcgg ctggggctct cgccggcgtg   4623

gatccggccc ggatctcgcg gggaatgggg ctctcggatg tagatctgcg atccgccgtt   4683

gttgggggag atgatggggg gtttaaaatt tccgccgtgc taaacaagat caggaagagg   4743

ggaaaagggc actatggttt atatttttat atatttctgc tgcttcgtca ggcttagatg   4803

tgctagatct ttctttcttc tttttgtggg tagaatttga atccctcagc attgttcatc   4863

ggtagttttt cttttcatga tttgtgacaa atgcagcctc gtgcggagct tttttgtagg   4923

tagaagtgat caacc atg agc aaa gaa atc agg ctc aac ctt tct cgt gag    4974
                 Met Ser Lys Glu Ile Arg Leu Asn Leu Ser Arg Glu
```

-continued

```
                235                 240

agc ggc gcc gac ctg tac ctc aag atc ctc gcc ttc gtg aag ccc gag     5022
Ser Gly Ala Asp Leu Tyr Leu Lys Ile Leu Ala Phe Val Lys Pro Glu
245                 250                 255                 260

cac ttc ttt cag gcg tac ctc ctg tgc cgc gag ttc gag agc atc gtg     5070
His Phe Phe Gln Ala Tyr Leu Leu Cys Arg Glu Phe Glu Ser Ile Val
                265                 270                 275

gat cct aca acc cgc gag tct gac ttc gac aag acg ctg acc atc gtg     5118
Asp Pro Thr Thr Arg Glu Ser Asp Phe Asp Lys Thr Leu Thr Ile Val
            280                 285                 290

aag tcg gac tcc acc ctc gtg acc gtg ggc acg atg aac acc aag ctg     5166
Lys Ser Asp Ser Thr Leu Val Thr Val Gly Thr Met Asn Thr Lys Leu
        295                 300                 305

gtc aat agc caa gag atc ctc gtg tcg gac ttg atc act caa gtc ggt     5214
Val Asn Ser Gln Glu Ile Leu Val Ser Asp Leu Ile Thr Gln Val Gly
    310                 315                 320

tcc cag atc gcc gat acc ctc ggc atc acg gac atc gac gcc aac acc     5262
Ser Gln Ile Ala Asp Thr Leu Gly Ile Thr Asp Ile Asp Ala Asn Thr
325                 330                 335                 340

cag caa cag ctc acg gag ctg atc ggc aac ctc ttc gtg aac ctc aat     5310
Gln Gln Gln Leu Thr Glu Leu Ile Gly Asn Leu Phe Val Asn Leu Asn
                345                 350                 355

tcc caa gtt cag gag tac atc tac ttc tac gag gag aag gag aag cag     5358
Ser Gln Val Gln Glu Tyr Ile Tyr Phe Tyr Glu Glu Lys Glu Lys Gln
            360                 365                 370

acc tcc tac cgc tac aac atc ctc ttc gtg ttc gaa aag gag tcg ttc     5406
Thr Ser Tyr Arg Tyr Asn Ile Leu Phe Val Phe Glu Lys Glu Ser Phe
        375                 380                 385

atc acc att ctg cca atg ggc ttc gac gtg acc gtg aac acg aac aag     5454
Ile Thr Ile Leu Pro Met Gly Phe Asp Val Thr Val Asn Thr Asn Lys
    390                 395                 400

gag gcc gtc ctg aag ctg acc ccg aag gac aag gtt acc tac ggc cac     5502
Glu Ala Val Leu Lys Leu Thr Pro Lys Asp Lys Val Thr Tyr Gly His
405                 410                 415                 420

gtc agc gtc aag gcc ctc aac atc atc cag ctc att acg gag gac aag     5550
Val Ser Val Lys Ala Leu Asn Ile Ile Gln Leu Ile Thr Glu Asp Lys
                425                 430                 435

ttc aac ttc ctc gca acc ctc aag aag gct ctc aag acc ctg tga tga     5598
Phe Asn Phe Leu Ala Thr Leu Lys Lys Ala Leu Lys Thr Leu
            440                 445                 450

gaattctgca tgcgtttgga cgtatgctca ttcaggttgg agccaatttg gttgatgtgt   5658

gtgcgagttc ttgcgagtct gatgagacat ctctgtattg tgtttctttc cccagtgttt   5718

tctgtacttg tgtaatcggc taatcgccaa cagattcggc gatgaataaa tgagaaataa   5778

attgttctga ttttgagtgc aaaaaaaaag gaatt                              5813
```

<210> SEQ ID NO 44
<211> LENGTH: 232
<212> TYPE: PRT
<213> ORGANISM: Artificial Sequence
<220> FEATURE:
<223> OTHER INFORMATION: Synthetic Construct

<400> SEQUENCE: 44

```
Met Ala Phe Phe Asn Arg Val Ile Thr Leu Thr Val Pro Ser Ser Asp
1               5                   10                  15

Val Val Asn Tyr Ser Glu Ile Tyr Gln Val Ala Pro Gln Tyr Val Asn
            20                  25                  30

Gln Ala Leu Thr Leu Ala Lys Tyr Phe Gln Gly Ala Ile Asp Gly Ser
```

```
        35                  40                  45

Thr Leu Arg Phe Asp Phe Glu Lys Ala Leu Gln Ile Ala Asn Asp Ile
    50                  55                  60

Pro Gln Ala Ala Val Val Asn Thr Leu Asn Gln Thr Val Gln Gln Gly
65                  70                  75                  80

Thr Val Gln Val Ser Val Met Ile Asp Lys Ile Val Asp Ile Met Lys
                85                  90                  95

Asn Val Leu Ser Ile Val Ile Asp Asn Lys Lys Phe Trp Asp Gln Val
            100                 105                 110

Thr Ala Ala Ile Thr Asn Thr Phe Thr Asn Leu Asn Ser Gln Glu Ser
        115                 120                 125

Glu Ala Trp Ile Phe Tyr Tyr Lys Glu Asp Ala His Lys Thr Ser Tyr
    130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
            180                 185                 190

Thr Val Lys Ala Ile Asn Val Val Gln Ala Leu Gln Ser Ser Arg Asp
        195                 200                 205

Ser Lys Val Val Asp Ala Phe Lys Ser Pro Arg His Leu Pro Arg Lys
    210                 215                 220

Arg His Lys Ile Cys Ser Asn Ser
225                 230


<210> SEQ ID NO 45
<211> LENGTH: 218
<212> TYPE: PRT
<213> ORGANISM: Artificial Sequence
<220> FEATURE:
<223> OTHER INFORMATION: Synthetic Construct

<400> SEQUENCE: 45

Met Ser Lys Glu Ile Arg Leu Asn Leu Ser Arg Glu Ser Gly Ala Asp
1               5                   10                  15

Leu Tyr Leu Lys Ile Leu Ala Phe Val Lys Pro Glu His Phe Phe Gln
            20                  25                  30

Ala Tyr Leu Leu Cys Arg Glu Phe Glu Ser Ile Val Asp Pro Thr Thr
        35                  40                  45

Arg Glu Ser Asp Phe Asp Lys Thr Leu Thr Ile Val Lys Ser Asp Ser
    50                  55                  60

Thr Leu Val Thr Val Gly Thr Met Asn Thr Lys Leu Val Asn Ser Gln
65                  70                  75                  80

Glu Ile Leu Val Ser Asp Leu Ile Thr Gln Val Gly Ser Gln Ile Ala
                85                  90                  95

Asp Thr Leu Gly Ile Thr Asp Ile Asp Ala Asn Thr Gln Gln Gln Leu
            100                 105                 110

Thr Glu Leu Ile Gly Asn Leu Phe Val Asn Leu Asn Ser Gln Val Gln
        115                 120                 125

Glu Tyr Ile Tyr Phe Tyr Glu Glu Lys Glu Lys Gln Thr Ser Tyr Arg
    130                 135                 140

Tyr Asn Ile Leu Phe Val Phe Glu Lys Glu Ser Phe Ile Thr Ile Leu
145                 150                 155                 160

Pro Met Gly Phe Asp Val Thr Val Asn Thr Asn Lys Glu Ala Val Leu
```

```
                        165                 170                 175
Lys Leu Thr Pro Lys Asp Lys Val Thr Tyr Gly His Val Ser Val Lys
            180                 185                 190

Ala Leu Asn Ile Ile Gln Leu Ile Thr Glu Asp Lys Phe Asn Phe Leu
            195                 200                 205

Ala Thr Leu Lys Lys Ala Leu Lys Thr Leu
            210                 215

<210> SEQ ID NO 46
<211> LENGTH: 1413
<212> TYPE: DNA
<213> ORGANISM: Articifial Sequence
<220> FEATURE:
<221> NAME/KEY: CDS
<222> LOCATION: (1)..(1407)
<223> OTHER INFORMATION: TIC127
<220> FEATURE:
<223> OTHER INFORMATION: Synthetic Construct
<220> FEATURE:
<223> OTHER INFORMATION: (1)..(696)
<223> OTHER INFORMATION: TIC809 amino acid sequence
<220> FEATURE:
<223> OTHER INFORMATION: (697)..(753)
<223> OTHER INFORMATION: proteolysis susceptible spacer or linker amino
      acid sequence
<220> FEATURE:
<223> OTHER INFORMATION: (754)..(1407)
<223> OTHER INFORMATION: TIC810 amino acid sequence

<400> SEQUENCE: 46

atg gcc ttc ttc aac cgg gtg atc acc ctc acg gtg ccg tcg tca gac      48
Met Ala Phe Phe Asn Arg Val Ile Thr Leu Thr Val Pro Ser Ser Asp
1               5                   10                  15

gtg gtc aac tac tcg gag atc tac cag gtg gct cct cag tat gtc aac      96
Val Val Asn Tyr Ser Glu Ile Tyr Gln Val Ala Pro Gln Tyr Val Asn
            20                  25                  30

cag gcc ctg acc ctg gcc aag tac ttc cag ggc gcc atc gac ggc agc     144
Gln Ala Leu Thr Leu Ala Lys Tyr Phe Gln Gly Ala Ile Asp Gly Ser
        35                  40                  45

acc ctg agg ttc gac ttc gag aag gcg tta cag atc gcc aac gac atc     192
Thr Leu Arg Phe Asp Phe Glu Lys Ala Leu Gln Ile Ala Asn Asp Ile
    50                  55                  60

ccg cag gcc gcg gtg gtc aac acc ctg aac cag acc gtc cag cag ggg     240
Pro Gln Ala Ala Val Val Asn Thr Leu Asn Gln Thr Val Gln Gln Gly
65                  70                  75                  80

acc gtc cag gtc agc gtc atg atc gac aag atc gtg gac atc atg aag     288
Thr Val Gln Val Ser Val Met Ile Asp Lys Ile Val Asp Ile Met Lys
                85                  90                  95

aat gtc ctg tcc atc gtg ata gac aac aag aag ttt tgg gat cag gtc     336
Asn Val Leu Ser Ile Val Ile Asp Asn Lys Lys Phe Trp Asp Gln Val
            100                 105                 110

acg gct gcc atc acc aac acc ttc acg aac ctg aac agc cag gag tcg     384
Thr Ala Ala Ile Thr Asn Thr Phe Thr Asn Leu Asn Ser Gln Glu Ser
        115                 120                 125

gag gcc tgg atc ttc tat tac aag gag gac gcc cac aag acg tcc tac     432
Glu Ala Trp Ile Phe Tyr Tyr Lys Glu Asp Ala His Lys Thr Ser Tyr
    130                 135                 140

tat tac aac atc ctc ttc gcc atc cag gac gaa gag acg ggt ggc gtg     480
Tyr Tyr Asn Ile Leu Phe Ala Ile Gln Asp Glu Glu Thr Gly Gly Val
145                 150                 155                 160

atg gcc acg ctg ccc atc gcc ttc gac atc agt gtg gac atc gag aag     528
Met Ala Thr Leu Pro Ile Ala Phe Asp Ile Ser Val Asp Ile Glu Lys
                165                 170                 175
```

-continued

```
gag aag gtc ctg ttc gtg acc atc aag gac act gag aat tac gcc gtc      576
Glu Lys Val Leu Phe Val Thr Ile Lys Asp Thr Glu Asn Tyr Ala Val
            180                 185                 190

acc gtc aag gcg atc aac gtg gtc cag gca ctc cag tct agc agg gat      624
Thr Val Lys Ala Ile Asn Val Val Gln Ala Leu Gln Ser Ser Arg Asp
        195                 200                 205

tct aag gtg gtt gat gcg ttc aaa tcg cca cgg cac tta ccc cgg aag      672
Ser Lys Val Val Asp Ala Phe Lys Ser Pro Arg His Leu Pro Arg Lys
    210                 215                 220

agg cat aag att tgc tct aac tcg aag ccc gcc ctg ctc aag gag gct      720
Arg His Lys Ile Cys Ser Asn Ser Lys Pro Ala Leu Leu Lys Glu Ala
225                 230                 235                 240

ccc cgc gcc gag gag gag ctg cct ccc cgc aag atg agc aaa gaa atc      768
Pro Arg Ala Glu Glu Glu Leu Pro Pro Arg Lys Met Ser Lys Glu Ile
                245                 250                 255

agg ctc aac ctt tct cgt gag agc ggc gcc gac ctg tac ctc aag atc      816
Arg Leu Asn Leu Ser Arg Glu Ser Gly Ala Asp Leu Tyr Leu Lys Ile
            260                 265                 270

ctc gcc ttc gtg aag ccc gag cac ttc ttt cag gcg tac ctc ctg tgc      864
Leu Ala Phe Val Lys Pro Glu His Phe Phe Gln Ala Tyr Leu Leu Cys
        275                 280                 285

cgc gag ttc gag agc atc gtg gat cct aca acc cgc gag tct gac ttc      912
Arg Glu Phe Glu Ser Ile Val Asp Pro Thr Thr Arg Glu Ser Asp Phe
    290                 295                 300

gac aag acg ctg acc atc gtg aag tcg gac tcc acc ctc gtg acc gtg      960
Asp Lys Thr Leu Thr Ile Val Lys Ser Asp Ser Thr Leu Val Thr Val
305                 310                 315                 320

ggc acg atg aac acc aag ctg gtc aat agc caa gag atc ctc gtg tcg     1008
Gly Thr Met Asn Thr Lys Leu Val Asn Ser Gln Glu Ile Leu Val Ser
                325                 330                 335

gac ttg atc act caa gtc ggt tcc cag atc gcc gat acc ctc ggc atc     1056
Asp Leu Ile Thr Gln Val Gly Ser Gln Ile Ala Asp Thr Leu Gly Ile
            340                 345                 350

acg gac atc gac gcc aac acc cag caa cag ctc acg gag ctg atc ggc     1104
Thr Asp Ile Asp Ala Asn Thr Gln Gln Gln Leu Thr Glu Leu Ile Gly
        355                 360                 365

aac ctc ttc gtg aac ctc aat tcc caa gtt cag gag tac atc tac ttc     1152
Asn Leu Phe Val Asn Leu Asn Ser Gln Val Gln Glu Tyr Ile Tyr Phe
    370                 375                 380

tac gag gag aag gag aag cag acc tcc tac cgc tac aac atc ctc ttc     1200
Tyr Glu Glu Lys Glu Lys Gln Thr Ser Tyr Arg Tyr Asn Ile Leu Phe
385                 390                 395                 400

gtg ttc gaa aag gag tcg ttc atc acc att ctg cca atg ggc ttc gac     1248
Val Phe Glu Lys Glu Ser Phe Ile Thr Ile Leu Pro Met Gly Phe Asp
                405                 410                 415

gtg acc gtg aac acg aac aag gag gcc gtc ctg aag ctg acc ccg aag     1296
Val Thr Val Asn Thr Asn Lys Glu Ala Val Leu Lys Leu Thr Pro Lys
            420                 425                 430

gac aag gtt acc tac ggc cac gtc agc gtc aag gcc ctc aac atc atc     1344
Asp Lys Val Thr Tyr Gly His Val Ser Val Lys Ala Leu Asn Ile Ile
        435                 440                 445

cag ctc att acg gag gac aag ttc aac ttc ctc gca acc ctc aag aag     1392
Gln Leu Ile Thr Glu Asp Lys Phe Asn Phe Leu Ala Thr Leu Lys Lys
    450                 455                 460

gct ctc aag acc ctg tgatga                                          1413
Ala Leu Lys Thr Leu
465
```

<210> SEQ ID NO 47
<211> LENGTH: 469

<212> TYPE: PRT
<213> ORGANISM: Artificial Sequence

<400> SEQUENCE: 47

```
Met Ala Phe Phe Asn Arg Val Ile Thr Leu Thr Val Pro Ser Ser Asp
1               5                   10                  15

Val Val Asn Tyr Ser Glu Ile Tyr Gln Val Ala Pro Gln Tyr Val Asn
            20                  25                  30

Gln Ala Leu Thr Leu Ala Lys Tyr Phe Gln Gly Ala Ile Asp Gly Ser
        35                  40                  45

Thr Leu Arg Phe Asp Phe Glu Lys Ala Leu Gln Ile Ala Asn Asp Ile
    50                  55                  60

Pro Gln Ala Ala Val Val Asn Thr Leu Asn Gln Thr Val Gln Gln Gly
65                  70                  75                  80

Thr Val Gln Val Ser Val Met Ile Asp Lys Ile Val Asp Ile Met Lys
                85                  90                  95

Asn Val Leu Ser Ile Val Ile Asp Asn Lys Lys Phe Trp Asp Gln Val
            100                 105                 110

Thr Ala Ala Ile Thr Asn Thr Phe Thr Asn Leu Asn Ser Gln Glu Ser
        115                 120                 125

Glu Ala Trp Ile Phe Tyr Tyr Lys Glu Asp Ala His Lys Thr Ser Tyr
    130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
            180                 185                 190

Thr Val Lys Ala Ile Asn Val Val Gln Ala Leu Gln Ser Ser Arg Asp
        195                 200                 205

Ser Lys Val Val Asp Ala Phe Lys Ser Pro Arg His Leu Pro Arg Lys
    210                 215                 220

Arg His Lys Ile Cys Ser Asn Ser Lys Pro Ala Leu Leu Lys Glu Ala
225                 230                 235                 240

Pro Arg Ala Glu Glu Glu Leu Pro Pro Arg Lys Met Ser Lys Glu Ile
                245                 250                 255

Arg Leu Asn Leu Ser Arg Glu Ser Gly Ala Asp Leu Tyr Leu Lys Ile
            260                 265                 270

Leu Ala Phe Val Lys Pro Glu His Phe Phe Gln Ala Tyr Leu Leu Cys
        275                 280                 285

Arg Glu Phe Glu Ser Ile Val Asp Pro Thr Thr Arg Glu Ser Asp Phe
    290                 295                 300

Asp Lys Thr Leu Thr Ile Val Lys Ser Asp Ser Thr Leu Val Thr Val
305                 310                 315                 320

Gly Thr Met Asn Thr Lys Leu Val Asn Ser Gln Glu Ile Leu Val Ser
                325                 330                 335

Asp Leu Ile Thr Gln Val Gly Ser Gln Ile Ala Asp Thr Leu Gly Ile
            340                 345                 350

Thr Asp Ile Asp Ala Asn Thr Gln Gln Gln Leu Thr Glu Leu Ile Gly
        355                 360                 365

Asn Leu Phe Val Asn Leu Asn Ser Gln Val Gln Glu Tyr Ile Tyr Phe
    370                 375                 380

Tyr Glu Glu Lys Glu Lys Gln Thr Ser Tyr Arg Tyr Asn Ile Leu Phe
385                 390                 395                 400
```

-continued

```
Val Phe Glu Lys Glu Ser Phe Ile Thr Ile Leu Pro Met Gly Phe Asp
                405                 410                 415

Val Thr Val Asn Thr Asn Lys Glu Ala Val Leu Lys Leu Thr Pro Lys
            420                 425                 430

Asp Lys Val Thr Tyr Gly His Val Ser Val Lys Ala Leu Asn Ile Ile
        435                 440                 445

Gln Leu Ile Thr Glu Asp Lys Phe Asn Phe Leu Ala Thr Leu Lys Lys
    450                 455                 460

Ala Leu Lys Thr Leu
465
```

INSECTICIDAL COMPOSITIONS AND METHODS FOR MAKING INSECT-RESISTANT TRANSGENIC PLANTS

CROSS-REFERENCE TO RELATED APPLICATIONS

This application is a U.S. national phase application under 35 U.S.C. §371 of PCT/US2006/033867, filed on Aug. 30, 2006, which claims benefit of priority to U.S. provisional application Ser. No. 60/713,111, filed Aug. 31, 2005. The contents of the applications mentioned above are hereby incorporated into this application by reference in their entireties.

BACKGROUND OF THE INVENTION

The present invention relates generally to the field of plant molecular biology, and more particularly to novel polynucleotide sequences and proteins encoded from such sequences derived from *Bacillus thuringiensis* and that encode ET29, TIC809, ET37, TIC810 and TIC812 proteins that exhibit toxicity to coleopteran species and to insects within the super-order referred to as Hemiptera. Coleopteran toxic proteins include ET29, TIC809 (an amino acid sequence variant of ET29), and ET37 (a homologue of ET29). TIC810 and TIC812 and nucleotide sequences encoding these proteins are also provided herein. When TIC810 or TIC812 are combined together with ET29, TIC809 or ET37, insecticidal compositions are provided that exhibit surprisingly greater potency against coleopteran species as compared to the presentation of only ET29, TIC809, or ET37 alone, and the combination of the two (TIC810 with either ET29, TIC809, or ET37, or TIC812 with either ET29, TIC809, or ET37) surprisingly provides a Hemiptera toxic composition, particularly when provided in the diet of species such as *Lygus hesperus* (western tarnished plant bug, WTPB). Methods of making and using polynucleotides encoding these and related proteins in the development of transgenic plants and plant cells that are resistant to Coleoptera and Hemiptera insect infestation are also disclosed.

Environmentally-sensitive methods and compositions for controlling or eradicating insect infestation are desirable in many instances because crops of commercial interest are often the targets of insect attack, particularly attack from coleopteran and lepidopteran insect pests. This is particularly true for farmers, nurserymen, growers, and commercial and residential areas which seek to control insect populations using environmentally friendly methods and compositions. Controlling or eradicating Hemiptera infestations of crops is also of commercial importance, and is increasing in importance as biotechnology approaches for coleopteran and Lepidopteran pest control methods become more widely available, particularly because fewer chemical insecticidal applications are utilized, which result in broad spectrum insecticidal activity.

The insecticidal properties of the bacterium *Bacillus thuringiensis* have been long recognized. *B. thuringiensis* is well known for producing proteinaceous parasporal crystals, or δ-endotoxins, that exhibit specific toxicity to a variety of lepidopteran, coleopteran, and dipteran larvae (English et. al., U.S. Pat. No. 6,063,597). Compositions comprising *B. thuringiensis* strains that produce insecticidal proteins have been used commercially as environmentally acceptable insecticides because they exhibit toxicity to specific target insects, and fail to exhibit toxicity to plants, animals and other non-target organisms.

More than 250 different δ-endotoxins have been isolated and characterized. Sequences encoding some of these δ-endotoxins have been used to construct genetically engineered *B. thuringiensis* products in which one or more insecticidal proteins are expressed that exhibit specific insecticidal activity to target pests, and have been approved for agricultural use as topically applied insecticidal compositions. Transgenic plants expressing one or more Bt insecticidal delta endotoxin proteins for use in controlling one or more insects within a specific class, such as Lepidopteran or coleopteran pests, have been approved for commercialization and have been successful. However, there is a risk that populations of target pest insects that feed on these transgenic plants will develop resistance to one or more of the toxins produced by the plants, and so there remains a need for identifying new insecticidal proteins that can be used alone or together with others that manifest their toxic effects through different modes of action. New insecticidal compositions are desirable for producing transgenic plants that express one or more *B. thuringiensis* insecticidal proteins toxic to the same insect species, providing a means for managing resistance and delaying or eliminating the development of resistance of any particular susceptible insect species to any of the one or more insecticidal agents expressed within a transgenic plant.

Most Bt toxins exhibit toxicity to lepidopteran species. Few have been shown to be effective against coleopteran species, and other than cytolytic toxins which exhibit no host range specificity, no Bt toxins have been shown to exhibit insecticidal activity to lepidopteran or coleopteran species and to Hemipteran species of insect pests. Thus there is a need for identifying new coleopteran and/or Hemipteran specific insecticidal compositions, and methods for controlling infestations by members of the Coleoptera and Hemiptera insect families, particularly for Coleoptera, by members of the family Chrysomelidae, more particularly, by the genus *Diabrotica* in the family Chrysomelidae that may include those that are from the genus *Diabrotica* including *Diabrotica virgifera* (western corn rootworm, WCR), *Diabrotica undecempunctata* (southern corn rootworm, SCR), *Diabrotica barberi* (Northern Corn Rootworm, NCR), *Diabrotica virgifera zeae* (Mexican Corn Rootworm, MCR), *Diabrotica balteata* (Brazilian Corn Rootworm, BZR) and Brazilian Corn Rootworm complex (BCR) consisting of *Diabrotica viridula* and *Diabrotica speciosa*), and particularly by members of the super-order Hemiptera, which includes any insect pest within the sub-order Heteroptera, including insects commonly referred to as stink bugs, *Lygus* bugs (including *Lygus Hesperus, Lygus lineolorus*, and *Lygus elisus*), assassin bugs, bed bugs, and flower bugs, and the sub-order Homoptera, including insects commonly known as cicadas, aphids, leafhoppers, scale insects and whiteflies.

SUMMARY OF THE INVENTION

The present invention provides polypeptide compositions isolated from *B. thuringiensis* that exhibit insecticidal activity against Coleoptera and Hemiptera insect pests, and provides nucleotide sequences encoding such polypeptides. The present invention provides control of Coleoptera and Hemiptera insect infestation by co-expressing at least two *B. thuringiensis* proteins in plants either as independent proteins or as a fusion protein of the two, resulting in surprisingly high levels of accumulation of the insecticidal proteins for providing effective control of target Coleoptera and Hemiptera insect pests and provides improvements in insect resistance management of Coleoptera and Hemiptera insect infestations. Additionally, a method of increasing the level of in planta accumulation of a *B. thuringiensis* insecticidal protein or variant thereof is provided that also provides the additional benefit of an absence of abnormal plant morphology for transgenic plants expressing these proteins.

In accomplishing the foregoing, a polynucleotide molecule is provided as set forth in SEQ ID NO:1, isolated from *B. thuringiensis* strain EG5078. The polynucleotide molecule encodes an insecticidal protein as set forth in SEQ ID NO:2, designated herein as ET37, exhibiting coleopteran insect pest inhibitory bioactivity.

A polynucleotide molecule as set forth in SEQ ID NO:3 is also provided that is isolated from *B. thuringiensis* strain EG4096 that encodes a TIC810 amino acid sequence as set forth in SEQ ID NO:4.

Yet another polynucleotide sequence is provided as set forth in SEQ ID NO:5 that encodes a TIC812 amino acid sequence as set forth in SEQ ID NO:6, which is isolated from *B. thuringiensis* strain EG5078. TIC812 is substantially identical to TIC810.

Specifically contemplated herein is an isolated polynucleotide molecule encoding an insecticidal protein or an insecticidal fragment thereof that exhibits at least from about 70% to about 99% or greater sequence similarity to a polypeptide sequence as set forth in SEQ ID NO:4 and SEQ ID NO:6, or any percentage there between. The insecticidal protein or insecticidal fragment is encoded by an isolated polynucleotide molecule derived from *B. thuringiensis*, and comprises a polynucleotide sequence that exhibits at least about 70%, about 80%, about 90% or about 99% or more sequence identity or any percentage in between, or that hybridizes under stringent conditions, to a polynucleotide sequence selected from the group consisting of SEQ ID NO:3 and SEQ ID NO:5 or the complement thereof.

In still another embodiment, there is provided a polynucleotide molecule for use in achieving improved expression of an insecticidal protein in a plant. The insecticidal protein preferably exhibits biological activity in controlling a Coleopteran or a Hemipteran insect pest or both, but may be active against other than a Coleopteran or Hemipteran insect pest, and may be encoded from a nucleotide sequence engineered for expression in a plant cell, such as is set forth in SEQ ID NO:15 (TIC810) or SEQ ID NO:19 (ET37).

Other polynucleotide sequences are provided for herein, for use in achieving stably transformed plant cells expressing one or more of the proteins of the present invention. Such nucleotide sequences include but are not intended to be limited to SEQ ID NO:13, SEQ ID NO:15, SEQ ID NO:17, SEQ ID NO:19, SEQ ID NO:28, SEQ ID NO:31, SEQ ID NO:34, SEQ ID NO:36, SEQ ID NO:38, SEQ ID NO:40, SEQ ID NO:43, and SEQ ID NO:46.

Oligonucleotide sequences are provided for use in identifying related nucleotide sequences in other bacteria, and in particular in other *Bacillus* bacterial strains including *Bacillus thuringiensis* and *Bacillus laterosperous* and *Bacillus entomocidus.*

Insecticidal proteins are provided that are exemplified by the amino acid sequences as set forth at SEQ ID NO:2, SEQ ID NO:4, SEQ ID NO:6, SEQ ID NO:8, SEQ ID NO:14, and SEQ ID NO:47 (TIC127). In particular embodiments, SEQ ID NO:4 (TIC810) and SEQ ID NO:6 (TIC812) are provided as accessory proteins, chaperones, or proteins that otherwise stabilize and enhance the expression and accumulation of a second protein expressed contemporaneously along with these accessory proteins. TIC809, ET29 and ET37 are all insecticidal proteins that exhibit greater levels of stability and therefore improved levels of accumulation when each are contemporaneously expressed along with a TIC810 or a TIC812 amino acid sequence. These sequences may be expressed together in the same subcellular compartment, i.e., both in the cytoplasm or both targeted for insertion into and accumulation in the chloroplast or plastid of a plant cell, or contemporaneously expressed to accumulate in different subcellular compartments, such as a TIC810 in the cytoplasm and an ET29 or TIC809 targeted for insertion into and accumulation in the plant chloroplast or plastid. In addition, the combination of any one of the TIC809, ET29, or ET37 proteins along with either of the TIC810 or TIC812 proteins results in a composition that is surprisingly stabilized for high level expression and accumulation of both protein components in plant cells and exhibits insecticidal activity directed to controlling plant pests in the orders Coleoptera and Hemiptera. The combination of proteins may also be expressed as a peptide fusion, for example, such as SEQ ID NO:47.

In a further embodiment, the present invention relates to a biologically pure culture of a *B. thuringiensis* wild type strain selected from the group consisting of EG5078, from which the polynucleotide sequence as set forth in SEQ ID NO:1 encoding the ET37 protein and SEQ ID NO:5 encoding the TIC812 protein are isolated, and EG4096, from which SEQ ID NO:3 encoding the TIC810 protein and SEQ ID NO:7 encoding the ET29 protein are isolated. EG4096 and EG5078 have been deposited with the Northern Regional Research Laboratory of Agricultural Research Service Center Collection (NRRL), USDA, 1815 North University Street, Peoria, Ill. 61604, pursuant to the Budapest Treaty on the International Recognition of the Deposit of Microorganism for the Purposes of Patent Procedure and have been assigned the accession Numbers NRRL-B-21582 and NRRL-B-30841 respectively. EG4096 was deposited on May 30, 1996 and EG5087 was deposited on May 3, 2005.

The present invention also relates to a recombinant DNA construct for expression in a plant or plant cell comprising a double gene cassette simultaneously expressing a first polynucleotide sequence and a second polynucleotide sequence wherein the first polynucleotide sequence encodes a polypeptide sequence selected from the group consisting of ET29, TIC809, and ET37 or insecticidally active fragments thereof, and wherein the second polynucleotide sequence encodes a polypeptide sequence selected from the group consisting of TIC810, and TIC812, and insecticidally active fragments thereof. The first polynucleotide sequence is selected from the group consisting of SEQ ID NO:13 and SEQ ID NO:17 and the second polynucleotide sequence is selected from the group consisting of SEQ ID NO:15 and SEQ ID NO:19, wherein the second polynucleotide sequence is co-expressed with the first polynucleotide sequence to enhance or improve expression of the first polynucleotide sequence, and to facilitate insecticidal activity directed to controlling Coleopteran and Hemipteran plant pest infestation.

The present invention also relates to a host cell transformed to contain either the expression vector or the recombinant DNA construct of the present invention, disclosed herein. The host cell may be selected from the group consisting of a bacterial cell, a fungal cell, and a plant cell. In one aspect of the embodiment, the host cell is a bacterial cell such as a *B. thuringiensis* cell that is transformed to contain the expression vector of the present invention. In another aspect of the embodiment, the host cell is a transgenic plant cell transformed to contain the recombinant DNA construct of the present invention. The recombinant DNA construct may comprise polynucleotide sequences that encode a combination of two of the four proteins simultaneously which polypeptide sequences are set forth in SEQ ID NO:14 (TIC809), SEQ ID NO:16 (TIC810), SEQ ID NO:18 (ET37)

and SEQ ID NO:20 (TIC812). Preferable combinations of the proteins may include TIC809 and TIC810, TIC809 and TIC812, ET37 and TIC810, and ET37 and TIC812 wherein co-expression of the polynucleotide sequence encoding TIC810 or TIC812 with the polynucleotide sequence encoding TIC809 (or ET29) or ET37 will result (a) in increased accumulation of TIC809 (or ET29) or ET37 protein in the plant cell, (b) in normal cell growth, (c) in a transgenic plant regenerated from the host plant cell, (d) in a normal phenotype, and (e) in increased levels of Coleopteran and Hemipteran insect resistance.

The transgenic plant cell of the present invention may comprise a maize plant cell, a wheat plant cell, a rye plant cell, a barley plant cell, an oat plant cell, a buckwheat plant cell, a sorghum plant cell, a rice plant cell, a sugarcane plant cell, a pigeon pea plant cell, a peanut plant cell, an onion plant cell, a garlic plant cell, a grass plant cell (including bent grass, fescue, brome, Timothy, orchard, Bermuda, zoysia, and the like), an *Arabidopsis* plant cell, a broccoli plant cell, a sunflower plant cell, a canola plant cell, a pea plant cell, a cowpea plant cell, a bean plant cell, a coffee plant cell, a soybean plant cell, a cotton plant cell, a linseed plant cell, a cauliflower plant cell, an asparagus plant cell, a lettuce plant cell, a cabbage plant cell, a tobacco plant cell, a spice plant cell (including curry, mustard, sage, parsley, pepper, thyme, cilantro, bay, cumin, turmeric, nutmeg, cinnamon, and the like), a sugar beet plant cell, a potato plant cell, a sweet potato plant cell, a carrot plant cell, a turnip plant cell, a celery plant cell, a tomato plant cell, an egg plant cell, a cucumber plant cell, a squash or melon plant cell and the like, a fruit tree plant cell (including apple, apricot, peach, pear, plum, orange, lemon, lime, and the like), a nut tree plant cell (including acorn, hickory, Brazil, pecan, walnut, hazelnut, and the like), a grape plant cell, a berry plant cell (including blackberry, blueberry, strawberry, cranberry, and the like), and flower plant cells.

In another embodiment, the present invention relates to a transgenic plant transformed to contain a recombinant DNA construct, disclosed herein. The transgenic plant may be regenerated from the transgenic plant cell of the present invention, or may be from a transgenic seed that is obtained from the regenerated transgenic plant or its offspring. The transgenic plant is selected from the group consisting of a monocot plant and a dicot plant that may include monocots such as maize, wheat, rye, barley, oats, buckwheat, sorghum, rice, sugarcane, onion, garlic, grass, or dicots such as sunflower, canola, peas, cowpeas, pigeon peas, beans, soybeans, coffee, broccoli, cotton, linseed, cauliflower, *Arabidopsis*, asparagus, lettuce, tobacco, spice plants (including curry, mustard, sage, parsley, pepper, thyme, cilantro, bay, cumin, turmeric, nutmeg, cinnamon and the like), sugar beet, potato, sweet potato, carrot, turnip, celery, tomato, egg plant, cucumber, squash or melon, fruit tree plant (including apple, apricot, peach, pear, plum, orange, lemon, lime and the like), berry plants (including blackberry, blueberry, strawberry, cranberry and the like), nut tree plants (including acorn, hickory, Brazil, pecan, walnut, hazelnut, and the like), grape plants, and flower plants.

In another embodiment, the present invention relates to a transgenic seed from the transgenic plant transformed to contain a recombinant DNA construct. The transgenic seed may be from the transgenic plant that is regenerated from the transgenic plant cell of the present invention, or may be from offspring of the regenerated transgenic plant, or from hybrids created as a result of crossing or breeding the transgenic plant with a non-transgenic plant. In one aspect, the transgenic seed may be coated with a seed coating and wherein the seed coating comprises a herbicidal composition, a fungicide seed coating, a bactericide seed coating, an insecticide seed coating, a plant hormone seed coating, a nutrient seed coating, a microbial inoculum seed coating, a color seed coating, an avian repellent seed coating, a rodent repellent seed coating, an insecticidal protein seed coating, a bacterial seed coating containing an insecticidal protein, a single stranded RNA seed coating, a double stranded RNA seed coating, a micro RNA seed coating or a small interfering RNA seed coating. One means for enabling and stabilizing a seed coating comprising such single or dsRNA compositions is to combine such RNA molecules with complementary DNA molecules so that stabilized DNA-RNA molecular hybrids are presented in the seed coating composition, enabling the presentation of the dsRNA or single stranded RNA to a pest feeding on the seed or the microenvironment within the realm of the sprouting seed or micro roots of an emerging sprouting shoot upon germination of the coated seed.

In accordance with one embodiment of the present invention, there is provided a method for generating a plant resistant to Coleopteran and/or Hemipteran insect infestation, comprising the steps of: a) inserting into the genome of a plant cell a first nucleic acid molecule that functions in the plant to encode a first protein selected from the group consisting of SEQ ID NO:14 (TIC809) and SEQ ID NO:18 (ET37), and a second nucleic acid molecule that functions in the plant to encode a second protein selected from the group consisting of SEQ ID NO:16 (TIC810) and SEQ ID NO:20 (TIC812);

b) obtaining the plant cell containing the nucleic acid molecules of step (a); and c) generating from the plant cell a transgenic plant that expresses both proteins, wherein the transgenic plant exhibits Coleopteran and/or Hemipteran pest resistance compared to a plant lacking said molecules.

In another embodiment, the present invention also provides a method for controlling a Coleopteran and/or Hemipteran insect pest infestation of a plant, comprising providing in the diet of the insect pest a plant, plant tissue or plant cells expressing a TIC809, ET2, or ET37 protein along with a TIC810 or TIC812 protein.

The polynucleotide and polypeptide compositions and methods disclosed herein will find particular benefit when used against Coleopteran and Hemipteran insect pests selected from the group of Coleopteran families consisting of Chrysomelidae, Cucujidae, Scarabaeidae, Trogositidae, Tenebrionidae, Curculionidae, Elateridae and Bruchidae, and from members of the order Hemiptera including specifically the members of the sub-orders Heteroptera and Homoptera. In one aspect of the invention, the Coleopteran insects are those from the family Chrysomelidae. The exemplary Coleopteran insects in the family Chrysomelidae may include those that are from the genus *Diabrotica* including *D. virgifera* (WCR), *D. undecempunctata* (SCR), *D. barberi* (NCR), *D. virgifera zeae* (MCR), *D. balteata* (BZR) and Brazilian Corn Rootworm complex (BCR) consisting of *D. viridula* and *D. speciosa*).

A nucleic acid sequence molecule may be constructed to incorporate a third structural gene sequence encoding a third agent (dsRNA or protein) as a means for providing in the same plant an additional agronomic trait exhibiting activity directed to controlling more than one plant pest, such as exhibiting Coleopteran and/or Hemipteran insect control and an additional trait for a Lepidopteran insect resistance, resistance to bacterial, viral, or fungal infestation, nematode resistance, or for providing a supplemental trait such as a herbicide resistance trait, a yield trait, a stress trait, a feed enhancement or trait that results in the enhancement of feed processing, and the like. The method may consist of the steps of inserting into the genome of a plant cell a first nucleic acid molecule encoding a protein that is selected from the group consisting of SEQ ID NO:14 (TIC809) and, SEQ ID NO:18 (ET37). The first nucleic acid molecule is linked to a second nucleic acid molecule that encodes a protein selected from the group consisting of SEQ ID NO:16 (TIC810) and SEQ ID NO:20 (TIC812). A third nucleic acid molecule that is introduced into the plant genome encodes an agent that provides for an agronomic trait that is other than that provided for by the first and second nucleic acid molecules, including but not limited to Lepidopteran insect resistance, resistance to bacterial, viral, or fungal infestation, nematode resistance, or for providing a supplemental trait such as a herbicide resistance trait, a yield trait, a stress trait, a feed enhancement or trait that results in the enhancement of feed processing, and the like.

In addition to providing the proteins of the present invention in a composition for controlling Coleoptera or Hemiptera insect pest infestation, a polynucleotide sequence transcribing a ribonucleotide acid (RNA) molecule that functions, when ingested by an invertebrate pest, to control invertebrate pest infestation by inhibition of a biological function within the pest as a second mode of action or as an insect resistance management feature of the composition is also specifically contemplated. The RNA molecule may comprise a dsRNA molecule, a siRNA molecule, a miRNA molecule, or an ssRNA molecule, and should be specific for inhibiting an essential gene of a target pest such as a pest targeted by the compositions of the present invention.

The compositions and methods disclosed by the present invention provide many advantages over the prior art including those specifically outlined above. These advantages may include: obtaining improved control of susceptible insect pests including not only those that infest plants, obtaining a greater number of commercially viable insect resistant plant lines; achieving season long protection from insect pathogens; and increasing the incidence of morphologically-normal transformed plants.

DESCRIPTION OF THE SEQUENCES

SEQ ID NO:1 is a *B. thuringiensis* polynucleotide sequence encoding an insecticidal ET37 protein.

SEQ ID NO:2 is an ET37 amino acid sequence encoded by the polynucleotide sequence as set forth in SEQ ID NO:1.

SEQ ID NO:3 is a polynucleotide sequence encoding an insecticidal TIC810 protein.

SEQ ID NO:4 is a TIC810 amino acid sequence encoded by the polynucleotide sequence as set forth in SEQ ID NO:3.

SEQ ID NO:5 is a *B. thuringiensis* polynucleotide sequence encoding a TIC812 protein.

SEQ ID NO:6 is a TIC812 amino acid sequence encoded by the polynucleotide sequence as set forth in SEQ ID NO:5.

SEQ ID NO:7 is a *B. thuringiensis* polynucleotide sequence encoding an ET29 protein.

SEQ ID NO:8 is an ET29 amino acid sequence encoded by the polynucleotide sequence as set forth in SEQ ID NO:7.

SEQ ID NO:9 is a *B. thuringiensis* polynucleotide sequence encoding TIC810 from nucleotide position 1 to nucleotide position 657 and encoding ET29 from nucleotide position 716 to 1411.

SEQ ID NO:10 is a *B. thuringiensis* polynucleotide sequence encoding TIC812 from nucleotide position 1 to 657 and encoding ET37 from nucleotide position 716 to 1411.

SEQ ID NO:11 is a polynucleotide sequence encoding TIC810 from nucleotide position 1 to nucleotide position 657 and encoding ET37 from nucleotide position 716 to 1411.

SEQ ID NO:12 is a polynucleotide sequence encoding TIC812 from nucleotide position 1 to 657 and encoding ET29 from nucleotide position 716 to 1411.

SEQ ID NO:13 is a polynucleotide sequence constructed for expression in a plant cell that encodes a TIC809 protein.

SEQ ID NO:14 is a TIC809 amino acid sequence encoded by the polynucleotide sequence as set forth in SEQ ID NO:13.

SEQ ID NO:15 is a polynucleotide sequence constructed for expression in a plant cell that encodes a TIC810 protein.

SEQ ID NO:16 is a TIC810 amino acid sequence encoded by the polynucleotide sequence as set forth in SEQ ID NO:15.

SEQ ID NO:17 represents a polynucleotide sequence constructed for expression in a plant cell that encodes an ET37 protein.

SEQ ID NO:18 is an ET37 amino acid sequence encoded by the polynucleotide sequence as set forth in SEQ ID NO:17.

SEQ ID NO:19 is a polynucleotide sequence constructed for expression in a plant cell that encodes a TIC812 protein.

SEQ ID NO:20 is a TIC812 amino acid sequence encoded by the polynucleotide sequence as set forth in SEQ ID NO:19.

SEQ ID NO:21 is a thermal amplification primer for use in amplifying a nucleotide sequence encoding a TIC810 amino acid sequence and is referred to herein as pr370.

SEQ ID NO:22 is a thermal amplification primer for use in amplifying a nucleotide sequence encoding a TIC810 amino acid sequence and is referred to herein as pr371.

SEQ ID NO:23 is a thermal amplification primer for use in amplifying a nucleotide sequence encoding a TIC810 amino acid sequence and is referred to herein as pr375.

SEQ ID NO:24 is a thermal amplification primer for use in amplifying a nucleotide sequence encoding a TIC810 amino acid sequence and is referred to herein as pr376.

SEQ ID NO:25 is a thermal amplification primer for use in amplifying a nucleotide sequence encoding a ET29 amino acid sequence and is referred to herein as pr365.

SEQ ID NO:26 is a thermal amplification primer for use in amplifying a nucleotide sequence encoding a ET29 amino acid sequence and is referred to herein as pr372.

SEQ ID NO:27 is a thermal amplification primer for use in amplifying a nucleotide sequence encoding a TIC810_ET29 or a TIC812_ET37 operon sequence and is referred to herein as pr421.

SEQ ID NO:28 is a synthetic nucleotide sequence present in transformation vector pMON64138 and consisting of a first plant expression cassette encoding a TIC809 protein and a second plant expression cassette encoding a TIC810 protein.

SEQ ID NO:29 is a TIC809 amino acid sequence encoded from the first plant expression cassette as set forth in SEQ ID NO:28.

SEQ ID NO:30 is a TIC810 amino acid sequence encoded from the second plant expression cassette as set forth in SEQ ID NO:28.

SEQ ID NO: 31 is a synthetic nucleotide sequence present in pMON64139 and consisting of a first plant expression cassette encoding a chloroplast targeted TIC809 and a second plant expression cassette encoding a chloroplast targeted TIC810.

SEQ ID NO:32 is a TIC809 amino acid sequence encoded from the first plant expression cassette as set forth in SEQ ID NO:31.

SEQ ID NO:33 is a TIC810 amino acid sequence encoded from the second plant expression cassette as set forth in SEQ ID NO:31.

SEQ ID NO:34 is a synthetic nucleotide sequence present in pMON70513 and consists of a plant expression cassette encoding a TIC809 amino acid sequence.

SEQ ID NO:35 is a TIC809 amino acid sequence encoded from the plant expression cassette as set forth in SEQ ID NO:34.

SEQ ID NO:36 is a synthetic nucleotide sequence present in pMON70514 and consists of a plant expression cassette encoding a chloroplast targeted TIC809 amino acid sequence.

SEQ ID NO:37 is a TIC809 amino acid sequence encoded from the plant expression cassette as set forth in SEQ ID NO:36.

SEQ ID NO:38 is a synthetic nucleotide sequence present in pMON64144 and consists of a plant expression cassette encoding a chloroplast targeted TIC809 amino acid sequence.

SEQ ID NO:39 is a TIC809 amino acid sequence encoded from the plant expression cassette as set forth in SEQ ID NO:38.

SEQ ID NO:40 is a synthetic nucleotide sequence present in pMON64150 and consists of a first plant expression cassette encoding a chloroplast targeted TIC809 amino acid sequence and a second plant expression cassette encoding a chloroplast targeted TIC810 amino acid sequence.

SEQ ID NO:41 is a TIC809 amino acid sequence encoded from the first plant expression cassette as set forth in SEQ ID NO:40.

SEQ ID NO:42 is a TIC810 amino acid sequence encoded from the second plant expression cassette as set forth in SEQ ID NO:40.

SEQ ID NO:43 is a synthetic nucleotide sequence present in pMON64151 and consists of a first plant expression cassette encoding a TIC809 amino acid sequence and a second plant expression cassette encoding a TIC810 amino acid sequence.

SEQ ID NO:44 is a TIC809 amino acid sequence encoded from the first plant expression cassette as set forth in SEQ ID NO:43.

SEQ ID NO:45 is a TIC810 amino acid sequence encoded from the second plant expression cassette as set forth in SEQ ID NO:43.

SEQ ID NO:46 is a nucleotide sequence encoding a TIC127 peptide which corresponds to a fusion between TIC809 (encoded by nucleotide position 1-696) and TIC810 (encoded by nucleotide position 754-1407), in which a short linker sequence (encoded by nucleotide position 697-753) has been introduced to allow for the two proteins to be separated by proteolysis after expression in a plant cell (or upon ingestion in the gut of a target insect pest).

SEQ ID NO:47 is a TIC127 amino acid sequence.

DETAILED DESCRIPTION OF THE PRESENT INVENTION

Polynucleotide sequences derived from *B. thuringiensis* are provided herein that encode ET29, ET37, TIC809, TIC810 and TIC812 proteins as well as a fusion between the ET29 derivative TIC809 and TIC810. Synthetic nucleotide sequences constructed for expression in plants are also provided that encode ET29, TIC809, ET37, TIC810 and TIC812 amino acid sequences as well as the TIC127 protein fusion between TIC809 and TIC810. Methods of making and using the polynucleotide sequences in the development of transgenic plants and plant cells that are resistant to Coleopteran and Hemipteran insect infestation are also disclosed. The proteins are also provided as insecticidal compositions either in formulations for topical application in various agricultural or animal environments, or as insecticidal compositions produced by a preferred host cell such as a bacterial cell, a plant cell, or a yeast or fungal cell. With reference to the term "derived", it is intended that a sequence is directly isolatable from a particular source, or after isolation from a particular source, a sequence such as a nucleotide sequence is modified to encode a protein that is substantially the same as the sequence that was isolated from a particular source. Alternatively, an amino acid sequence can be substantially the same as an amino acid sequence isolated from a particular source, or encoded from a particular nucleotide sequence. An amino acid sequence can be a chimera of a number of different amino acid sequences that have been each individually isolated from a particular source, but various segments of such different amino acid sequences have been cobbled together to produce the chimera. In this sense, the chimera is derived from each of the various different amino acid sequences. A nucleotide sequence can be similarly derived from other nucleotide sequences. A nucleotide sequence can be derived from other nucleotide sequences as a consequence of its production or having been obtained by reference to one or more other nucleotide sequences. Similarly, amino acid sequences can be obtained or produced by reference to one or more other amino acid sequences, and thus be derived in that manner.

Synthetic polynucleotide sequences of the present invention are preferably designed for in planta expression of insecticidal proteins in plant tissues and in plant cells. In particular, the insecticidal proteins of the present invention are referred to as ET29, ET37, TIC809, TIC810, TIC812 and TIC127 proteins. An amino acid sequence of any of these proteins is intended to be within the scope of the present invention so long as it exhibits insecticidal activity at least equivalent to that of the full length protein from which it was derived.

In one embodiment, the present invention relates to a biologically pure culture of a *B. thuringiensis* bacterium containing a nucleotide sequence encoding one or more of the proteins disclosed herein. In particular, the nucleotide sequences are those set forth in SEQ ID NO:1 encoding ET37 (SEQ ID NO:2), SEQ ID NO:3 encoding TIC810 (SEQ ID NO:4), SEQ ID NO:5 encoding TIC812 (SEQ ID NO:6), and SEQ ID NO:7 encoding ET29 (SEQ ID NO:8). Also, fusions are contemplated and specifically embodied herein, such as TIC127 (SEQ ID NO:46 encoding SEQ ID NO:47). A biologically pure culture may also include those that are transformed with a polynucleotide sequence of the present invention or with two or more polynucleotide sequences, at least a first polynucleotide sequence being selected from the group consisting of an ET37 coding sequence and an ET29 coding sequence, and at least a second polynucleotide sequence being selected from the group consisting of a TIC810 coding sequence and a TIC812 coding sequence. Exemplary bacterial strains, i.e., EG4096 and EG5078, have been deposited in the Northern Regional Research Laboratory of Agricultural Research Service Center Collection (NRRL), USDA, 1815 North University Street, Peoria, Ill. 61604, pursuant to the Budapest Treaty on the International Recognition of the Deposit of Microorganism for the Purposes of Patent Procedure and have been assigned the accession numbers as indicated in Table 1.

TABLE 1

Exemplary *B. thuringiensis* strains

| Bt Strain | Nature of Strains | Toxins contained | NRRL numbers | Deposit Dates |
|---|---|---|---|---|
| EG4096 | Wild type | ET29, TIC810 | NRRL-B-21582 | May 30, 1996 |
| EG5078 | Wild type | ET37, TIC812 | NRRL B-30841 | May 3, 2005 |

The naturally occurring (native) polynucleotide sequence encoding ET37 is set forth at SEQ ID NO:1. This sequence exhibits about 99% sequence identity to the polynucleotide sequence encoding an ET29 insecticidal protein, as disclosed in U.S. Pat. No. 6,093,695, and as disclosed herein at SEQ ID NO:7. The ET37 amino acid sequence encoded from SEQ ID NO:1 is set forth at SEQ ID NO:2. Insecticidal activity of the ET37 protein is demonstrated herein in bioassays using Coleopteran insects of the genus *Diabrotica*, including WCR and SCR, and Hemipteran insects of the genus *Lygus*. In the course of conducting sequence analysis of the extra-chromosomal plasmids on which the ET37 and ET29 coding sequences are located in their respective strains, a single open reading frame was identified upstream of each of the ET37 and ET29 open reading frames, these corresponding respectively to sequences encoding the proteins TIC812 and TIC810. The native polynucleotide molecule (SEQ ID NO:3) encoding a TIC810 protein (SEQ ID NO:4) is positioned immediately upstream of the ET29 coding sequence in *B. thuringiensis* strain EG4096. The native polynucleotide molecule (SEQ ID NO:5) encoding a TIC812 protein (SEQ ID NO:6) is positioned immediately upstream of the ET37 coding sequence in *B. thuringiensis* strain EG5078.

ET29, ET37, TIC810 and TIC812 all may be distantly related to the Cyt insecticidal toxin family, however from a phylogenetic perspective, the ET29 and 37 proteins are much closer to each other than to other Cyt proteins, and the TIC810 and 812 proteins are also much closer to each other than to other Cyt proteins. The ET37 amino acid sequence shares about 99% sequence similarity with that of ET29. TIC810 and TIC812 exhibit about 97% amino acid sequence similarity to each other. TIC810 exhibits about 33% amino acid sequence similarity with ET29 and ET37. Similarly, the TIC812 protein exhibits about 32% amino acid sequence similarity with ET29 and ET37. The similarity comparison is based upon Pairwise alignments between the proteins using the Wisconsin Package Version 10.3, Accelrys Inc., San Diego, Calif.

In accordance with the present invention, certain combinations of expression of the TIC810, TIC812, ET37 and ET29 proteins in a host cell function to achieve a desirable elevated level of insecticidal protein accumulation in the host cell, resulting in improved insecticidal activity directed to certain target Coleopteran and Hemipteran insect pests. A polynucleotide sequence encoding ET29 can be co-expressed with a polynucleotide sequence encoding a TIC810 protein to achieve enhanced expression and or accumulation of the ET29 insecticidal protein in a host cell. Similarly, a polynucleotide sequence encoding ET37 can be co-expressed with a polynucleotide sequence encoding TIC812 to achieve an enhanced expression and or accumulation of the ET37 insecticidal protein in a host cell. It is envisioned that TIC812 is interchangeable with TIC810 as an insecticidal agent, and as a chaperone or accessory protein required for stabilization, accumulation, and improved host range bioactivity of either ET37 or ET29. Co-expression of TIC810 or TIC812 along with ET37 or ET29 results in improved expression and/or accumulation of ET37 or ET29. Such combinations are referred to herein as stabilized insecticidal compositions. Furthermore, the stabilized compositions exhibit a greater host range, at least with reference to its insecticidal efficacy directed to Coleopteran and Hemipteran insect pests, than any of the individual components of the compositions. A recombinant cell in which a first protein consisting of either ET37 or ET29 and a second protein consisting of either TIC810 or TIC812 exhibits increased levels of ET29/ET37 accumulation, provides levels of Coleopteran and Hemipteran insect resistance that were previously unattainable with the insecticidal proteins ET37 and ET29, and results in an absence of abnormal morphology and/or phenotype of the cell or organism consisting of such recombinant cells, all in comparison to a cell expressing either ET29 or ET37 in the absence of TIC810 or TIC812.

The above insecticidal combinations may also be expressed in a plant along with at least one additional insecticidal protein different from either protein comprising the combination, exhibiting a mode of action different from either protein comprising the combination, and toxic to the same insect species as the proteins of the combination. This second combination, which includes the additional insecticidal protein, provides a means of Coleopteran insect resistance management. Such additional proteins include but are not limited to the Coleopteran toxins Cry3Bb and variants, Cry22A, TIC901, TIC1201, TIC407, TIC417, CryET70, the binary toxins PS149B1, ET33/34, and ET80/76, and various other proteins that have been shown to exhibit Coleopteran insecticidal activity such as patatins, Cry3Aa variants, and non-specific insecticidal compositions isolatable from bacterial species such as *Xenhorabdus* and *Photorhabdus*.

ET29 or ET37 protein each may be combined with TIC810 or TIC812 and co-expressed in a plant with an agent that exhibits insecticidal activity directed to other than a Coleopteran insect pest species, achieving desired control of more than one type of common plant pests selected from the group consisting of Lepidopteran insect pests, and Hemipteran insect pests. Furthermore, such combinations could be combined with still other agents that are effective in controlling virus pests, bacterial pests, fungal pests, and the like. The agents contemplated in such combinations can be expressed along with the ET29/ET37 and TIC810/TIC812 combination or provided through application of insecticidal or pesticidal agents in an agriculturally acceptable formulation, perhaps with a carrier such as an emollient, colloid, spray, powder, mixture, or dust. In situations in which the compositions would be useful in controlling animal pests such as fleas, ticks, lice, mites and the like, it is useful to include along with the ET29/ET37 and TIC810/TIC812 combination an agent that is effective for controlling the same or other pests to which the combination is directed, and so such applications should be provided in a pharmaceutically acceptable formulation. Particular formulations of the insecticidal combinations of the present invention are contemplated for use in topical and/or systemic application to field crops, grasses, fruits and vegetables, and ornamental plants. In one embodiment, the insecticidal composition comprises an oil flowable suspension of bacterial cells that is expressing one or more of the novel insecticidal proteins disclosed herein. Exemplary cells may be *B. thuringiensis* strains EG4096, EG5078, sIC8134 or sIC8135, however, any such bacterial host cell such as *B. megaterium, B. subtilis, E. coli*, or *Pseudomonas* spp. expressing an insecticidal composition would be useful.

The insecticidal compositions of the present invention may be combined with other biotechnology methods, such as double stranded RNA mediated gene suppression technology, to achieve desired control of one or more pests of a particular plant. Specific nucleotide sequences selected from the sequences native to the cells of a particular pest that are involved in an essential biological pathway are expressed in a plant cell in such a way as to result in the formation of a double stranded RNA, or even a stabilized double stranded RNA. In this manner, upon ingestion by the pest of a pesticidally effective amount of the RNA, i.e., one or more plant cells expressing the double stranded RNA derived from the cells of such pest, suppression of one or more essential biological pathways is suppressed in the pest. The pest contemporaneously ingests along with the dsRNA, a pesticidally effective amount of the insecticidal compositions described herein, resulting in the provision of an effective insect or pest resistance management system which avoids the likelihood of the onset of resistance because the two pesticidal agents are functioning through different modes of action. A particular recombinant plant cell expressing a composition corresponding to the Coleopteran and Hemipteran insecticidal proteins of the present invention can also express as dsRNA molecules one or more sequences derived from the genome of a targeted Coleopteran pest and one or more sequences derived from the genome of a targeted Hemipteran pest, resulting in the provision of multiple insecticidally effective amounts of the proteins of the present invention and of the dsRNA's designed for suppression of one or more essential genes in the targeted Coleopteran and/or Hemipteran pests. Plants consisting of the gene encoding one or more the proteins of the present invention alone or in combination with additional pest controlling agents such as dsRNA agents exhibit improved yield and drought tolerance compared to plants lacking such pesticidal agents. This may be because these traits result in stabilized root masses that are more uniform, strong and healthy and provides greater nutrient and moisture gathering capacity in comparison to root masses lacking such agents.

A chimeric protein may be synthesized in which a sequence encoding ET29 or ET37 and a sequence encoding TIC810 or a TIC812 is fused together, providing for expression of the stabilized insecticidal composition as a single protein. It is contemplated that the chimeric protein may not be stabilized or exhibit insecticidal bioactivity unless the two fused peptides are unlinked. This physical separation can be accomplished by including as a spacer between the proteins a unique peptide sequence that is the target for any number of proteases known in the art. The chimeric protein can also be linked to other sequences that affect the stability of the chimera, resulting in formation of a crystalline form or inclusion body that consists substantially of the chimera-fusion peptide to the exclusion of other contaminating compositions, peptides, or molecules. Such chimeras or fusions are exemplified herein in Example 11 as TIC127 (sequential fusion of TIC809 and TIC810 linked by a short peptide) and TIC128 (sequential fusion of TIC810 and TIC809) and are shown to exhibit Coleopteran and Hemipteran insecticidal bioactivity.

Expression vectors for use in a host cell are also provided. Expression vectors comprising sequences that result in the expression of a combination of at least two of the polynucleotide sequences disclosed herein are provided in exemplary embodiments. In one embodiment, an expression vector is an isolated and purified polynucleotide molecule comprising a combination of two different polynucleotide sequences, each sequence containing a promoter functional in a desired host cell that is operatively linked to a nucleotide segment encoding a TIC809, TIC810, TIC812, ET29, or ET37. In some embodiments, a transcription termination and polyadenylation sequence may be included 3' of the nucleotide segment encoding one of these proteins.

Expression vectors for use in a bacterial host cell are provided, e.g., in an *E. coli* cell or a *Bacillus* cell including one from *B. thuringiensis, B. megaterium, B. subtilis*, or related *Bacillus* species. Bacterial host cell expression vectors can contain one nucleotide sequence expressing one or more of the proteins of the present invention in series, in much the same way that proteins can be expressed in most bacterial cells, i.e., in a polycistronic expression cassette. Alternatively, a bacterial expression vector may consist of a nucleotide sequence encoding only one of the proteins of the present invention.

Promoters that function in bacteria are well-known in the art. An exemplary promoter for the *Bacillus* crystal proteins may include any of the known crystal protein gene promoters, including the ET29 gene promoter (U.S. Pat. No. 6,093,695), and promoters specific for *B. thuringiensis* sigma factors (Baum and Malvar, *Molec. Microbiol.,* 18(1): 1-12, 1995). Alternatively, mutagenized or recombinant crystal protein-encoding gene promoters may be engineered by those skilled in the art and used to promote expression of the novel polynucleotide sequences disclosed herein. For purpose of the present invention, the promoter used herein for expression of the polynucleotide sequences is cry1A promoter.

Recombinant DNA constructs for expression in a plant cell are provided. Such constructs typically contain two or more plant functional expression cassettes that are linked together in such a way as to enable the simultaneous introduction of the two or more expression cassettes into the same locus in a plant genome, or alternatively may contain two or more plant functional expression cassettes that are linked within the construct or vector, but are capable of being introduced independently into different loci within a plant genome. These expression cassettes may be referred to as a first and a second expression cassette expressing, respectively, a first polynucleotide sequence encoding a first protein and a second polynucleotide sequence encoding a second protein. It is intended that the first protein can be any of the proteins disclosed herein, and the second protein can be any of the other proteins disclosed herein other than the first protein. Exemplary polynucleotide sequences are provided as set forth in SEQ ID NO:13, SEQ ID NO:15, SEQ ID NO:17 and SEQ ID NO:19.

Promoters used in the recombinant DNA construct of the present invention should exhibit the ability to drive expression of the polynucleotide sequences encoding the insecticidal agents when introduced into plant cells. Promoters that are useful in expressing the polypeptide sequences in plants can be inducible, constitutive, tissue-specific or developmentally specific promoters for use in a monocot or a dicot plant. In one embodiment, the promoter selected for use may be a constitutive promoter and, for the purpose of the present invention, the promoter may specifically comprise an enhanced cauliflower mosaic virus (CaMV 35S) promoter. In another embodiment, the promoter selected may be a tissue-specific promoter and, for the purpose of the present invention, the promoter may specifically comprise a root-specific promoter Rcc3 isolated from rice (U.S. patent application Ser. No. 11/075,113).

A vector or construct may also include elements that function to regulate the level and timing of expression of the gene of interest to which they are linked, in addition to one or more promoters. For example, the construct may include an intron sequence. The intron sequence employed in the present invention may include a rice actin intron (U.S. Pat. No. 5,641,876). The recombinant DNA construct may also have a translation leader sequence between the promoter and the coding sequence. The vector or construct may also include, within the coding region of interest, a nucleic acid sequence that acts, in whole or in part, to terminate transcription of that region. In one embodiment, the polyadenylation sequence of the present invention may be from the 3' untranslated region of a wheat heat shock protein gene (tahsp17).

A recombinant DNA construct may include other elements as well. For example, the construct may contain DNA segments that provide replication function and one or more selectable markers for use in bacterial cells. The construct may also comprise a screenable marker, a selectable marker and other elements as appropriate for selection of plant or bacterial cells having the recombinant DNA constructs of the invention. The recombinant DNA constructs are designed with suitable selectable markers that can confer antibiotic or herbicide tolerance to the cell. The antibiotic tolerance polynucleotide sequences include, but are not limited to, polynucleotide sequences encoding for proteins involved in tolerance to kanamycin, neomycin, hygromycin, and other antibiotics known in the art. An antibiotic tolerance gene in such a vector may be replaced by a herbicide tolerance gene encoding for 5-enolpyruvylshikimate-3-phosphate synthase (EPSPS, described in U.S. Pat. Nos. 5,627,061, and 5,633, 435; Padgette et al. Herbicide Resistant Crops, Lewis Publishers, 53-85, 1996) or other selectable marker genes and their equivalents such as basta tolerance, bar tolerance, methotrexate resistance, glyphosate oxidoreductase, glyphosate acetyl transferase, phosphonate acetylase (phnO and alleles derived from Enterobacteriaceae), and dicamba tolerance genes, and the like. Plants expressing the insect tolerance properties of the present invention that are coupled with one or more such selectable markers are particularly useful for commercial purposes.

The polynucleotide sequences of the present invention may be used to transform a plant cell that can be regenerated to produce a transgenic plant that exhibits improved insect resistance when compared to the plant or plant cell from which the transgenic plant is derived. The polynucleotide sequences of the present invention may be modified to improve their expression in the plant host cell. Expression of the polynucleotide sequences of the present invention in the plant cell may achieve accumulations of the insecticidal proteins in the cytoplasm, or can result in the insecticidal proteins being accumulated into a subcellular organelle such as a chloroplast, a plastid or a mitochondrion.

In accomplishing the foregoing, the polynucleotide sequences encoding the proteins of the present invention as set forth in SEQ ID NO:14, SEQ ID NO:16, SEQ ID NO:18 and SEQ ID NO:20 and SEQ ID NO:47 have been improved for expression in plants. Such polynucleotide sequences exemplified herein are set forth in SEQ ID NO:13 (TIC809), SEQ ID NO:15 (TIC810), SEQ ID NO:17 (ET37), SEQ ID NO:19 (TIC812), and SEQ ID NO:46 (TIC127), and furthermore in expression cassette sequences as set forth at SEQ ID NO:28, SEQ ID NO:31, SEQ ID NO:34, SEQ ID NO:36, SEQ ID NO:38, SEQ ID NO:40, and SEQ ID NO:43. Co-expression of at least one of a TIC810 or TIC812 protein along with one or more of a ET29, TIC809, or ET37 insecticidal protein improves (or assists, acts as a chaperone to, stabilizes, or may otherwise interact with the insecticidal protein as an accessory protein) with the expression and/or accumulation of the insecticidal protein. Co-expression in a transgenic plant results in the absence of low levels of expression and/or accumulation and absence of phytotoxic effects observed when only an insecticidal protein such as ET29, ET37, or TIC809 are expressed alone.

There are many methods for introducing the recombinant DNA construct comprising the combination of the polynucleotide sequences into cells and suitable methods are believed to include virtually any method by which DNA can be introduced into a plant cell, such as by *Agrobacterium* infection, direct delivery of DNA such as, for example, by PEG-mediated transformation of protoplasts (Omirulleh et al., Plant Mol. Biol., 21:415-428, 1993), by desiccation/inhibition-mediated DNA uptake, by electroporation or by microprojectile bombardment and the like.

In consideration of insect resistance management (IRM), the compositions and methods of the present invention are useful in producing transgenic plants which express two or more *B. thuringiensis* proteins toxic to the same insect species and which confers a level of resistance management for delaying the onset of resistance of any particular susceptible insect species to one or more of the insecticidal agents expressed within the transgenic plant. Alternatively, expression of a *B. thuringiensis* insecticidal protein toxic to a particular target insect pest along with a different proteinaceous agent toxic to the same insect pest but which confers toxicity by a means different from that exhibited by the *B. thuringiensis* toxin is desirable. Such other different proteinaceous agents may comprise any of Cry insecticidal proteins, Cyt insecticidal proteins, insecticidal proteins from *Xenorhabdus* sp. or *Photorhabdus* sp., *B. thuringiensis* vegetative insecticidal proteins, and the like. One means for achieving this result would be to produce two different transgenic events, one event expressing a combination of the two insecticidal proteins of the present invention, active against Coleopteran and Hemipteran insects, and the other expressing a third insecticidal protein, and breeding the two traits together into a hybrid plant. The third insecticidal protein could be one that exhibits Coleopteran insecticidal activity, one that exhibits Hemipteran insecticidal activity, one that exhibits insecticidal activity directed to both Coleopteran and Hemipteran (and perhaps toxicity to other insect orders as well), or one that exhibits insecticidal activity directed to one or more other orders of insects other than Coleopteran and Hemipteran insect pests including but not limited to Lepidopteran, Orthoptera, Diptera and the like.

A pesticidal amount of the insecticidal proteins of the present invention may be provided in the diet of an insect pest. Typically, the diet consists of a plant part upon which the insect normally feeds, such as a plant tissue or plant cell, but may also include other compositions such as an artificial diet formulated for enhancing the development and survival of a particular insect pest. The insecticidal protein can be provided in a composition that is applied to the surface of the diet, or more preferably can be produced by the protein synthesis machinery of a cell and, as described above, accumulated within the plant cell or secreted outside of the plant cell, so long as the amount of the protein toxin provided is an insecticidal amount sufficient to inhibit the insect pest from further feeding, or to inhibit the further growth and development of the insect pest, or to cause mortality to the insect pest.

Transgenic plants can be selfed (self-pollinated) to generate seeds that exhibit a genotype that is homozygous with respect to the transgene encoding the insecticidal protein. Such seeds produce plants and seeds that are only homozygous with respect to the transgene encoding the insecticidal protein. Often, the transgenic plants that are produced are generated in varieties that fail to exhibit the most desirable agronomic qualities. Therefore, homozygous recombinant plants can be crossed with inbred lines that exhibit particular agronomically important qualities.

The present invention will find particular utility in the creation of transgenic plants of commercial interest including various turf grasses, wheat, corn, rice, barley, oats, a variety of ornamental plants and vegetables, as well as a number of nut- and fruit-bearing trees and plants. Specifically, these plants may include maize, wheat, rye, barley, oats, buckwheat, sorghum, rice, onion, grass, sunflower, canola, peas, beans, soybeans, cotton, linseed, cauliflower, asparagus, lettuce, tobacco mustard, sugar beet, potato, sweet potato, carrot, turnip, celery, tomato, egg plant, cucumber, squash, apple, apricot, peach, pear, plum, orange, blackberry, blueberry, strawberry, cranberry and lemon. In general, the invention is useful in monocotyledonous and dicotyledonous plant varieties. The transgenic plant is selected from the group consisting of a monocot plant and a dicot plant that may include monocots such as maize, wheat, rye, barley, oats, buckwheat, sorghum, rice, sugarcane, onion, garlic, grass, or dicots such as sunflower, canola, peas, cowpeas, pigeon peas, beans, soybeans, coffee, broccoli, cotton, linseed, cauliflower, *Arabidopsis*, asparagus, lettuce, tobacco, spice plants (including curry, mustard, sage, parsley, pepper, thyme, cilantro, bay, cumin, turmeric, nutmeg, cinnamon and the like), sugar beet, potato, sweet potato, carrot, turnip, celery, tomato, egg plant, cucumber, squash or melon, fruit tree plant (including apple, apricot, peach, pear, plum, orange, lemon, lime and the like), berry plants (including blackberry, blueberry, strawberry, cranberry and the like), nut tree plants (including acorn, hickory, Brazil, pecan, walnut, hazelnut, and the like), grape plants, and flowering plants.

DNA sequence information provided herein allows for the preparation of nucleotide sequences or probes and/or primers exhibiting the ability to specifically hybridize to nucleotide sequences disclosed herein, or to homologous sequences encoding proteins related to TIC810, TIC812, ET37 and ET29. The ability of such nucleic acid probes to specifically hybridize to a sequence encoding a related toxin or accessory/chaperonin-like protein provides particular utility in a variety of embodiments. Most importantly, the probes may be used in a variety of assays for detecting the presence of complementary sequences in a given sample. The nature of the regulatory environment under which transgenic plants containing the genes of the present invention are commercialized provides a particular utility to being able to detect the presence of the sequences encoding the proteins as well as the proteins of the present invention in a biological sample and provides a means for detecting infringement of certain claimed embodiments during the term of any patent that is issued thereon.

In certain embodiments, it is advantageous to use oligonucleotide primers, either alone or in pairs or other primer sets. The sequence of such primers is designed using a polynucleotide of the present invention for use in detecting, amplifying or mutating a defined segment of a toxin or accessory/chaperonin-like protein coding sequence from *B. thuringiensis* or other sources using thermal amplification methods. Segments of related toxin or accessory/chaperonin-like coding sequences from other species may also be amplified.

Kits for detecting, in a biological sample, polynucleotide or amino acid sequences of the present invention are also envisioned. Such kits contain one or more polynucleotide sequences each for use as a probe for detecting the presence of a polynucleotide sequence encoding an insecticidal protein of the present invention or fragment thereof. Such kits could also or alternatively contain antibody specific for binding to one or more polypeptides of the proteins of the present invention, as well as reagents for use with the probe or antibody, and the kits would also contain control samples for use in ensuring that the nucleotides or peptides identified with the probe and or antibody and reagents were functioning according to the manufacturers" instructions. All of the reagents necessary for carrying out the methods of identification of either nucleotide sequences or peptides would be packaged together in a kit along with instructions for use. An exemplary kit could contain a TIC810 or related polynucleotide sequence encoding an insecticidal protein along with a sample of the exemplary nucleotide sequence amplification primers pr375 and pr376 as set forth in SEQ ID NO:23 and SEQ ID NO:24, together with the necessary reagents necessary for carrying out an amplification reaction, all packaged together in the kit.

The antibodies that bind specifically to epitopes presented only by any one of ET37, TIC810 and TIC812 proteins or their homologs may also be used for identifying the presence of any one of ET37, TIC810 and TIC812 proteins or its homologs, for purifying the proteins or homologs, for identifying a nucleotide sequence from which an ET37, TIC810 or TIC812 protein or a homolog is being expressed, and for use in the kits, designed to allow the detection an ET37, TIC810 or TIC812 protein or a homolog or the detection of a nucleotide sequence expressing the protein or its homolog. The skilled artisan will readily appreciate that such antibodies also provide for the identification of fusions of such proteins, such as TIC127 and the like.

Agronomically and commercially important products and/or compositions of matter including but not limited to animal feed, commodities, and cotton or soybean or corn products and by-products that are intended for use as animal feeds or for use as food for human consumption or for use in compositions that are intended for human consumption including but not limited to cotton seed, cotton seed oil, cotton seed solids, and the like, soy meal, soy oil, soy flour, and the like, corn flour, corn meal, corn syrup, corn oil, corn starch, popcorn, corn cakes, cereals containing corn or soy, and corn by-products, and the like are intended to be within the scope of the present invention if these products and compositions of matter contain detectable amounts of the nucleotide sequences set forth herein as being diagnostic for the presence of a sequence encoding an ET29, an ET37, a TIC809, a TIC810, a TIC812, a TIC127, or combinations thereof and the like. Distillers dry goods solids are also contemplated as an agronomically and commercially important product, especially if it contains detectable amounts of a nucleotide sequence encoding one or more of the proteins of the present invention, or detectable amounts of one or more of the proteins of the present invention.

Seed comprising detectable amounts of nucleotide sequences encoding these proteins, or seed or plant parts that can be processed into products that contain detectable amounts of such nucleotide sequences or proteins are within the scope of the present invention.

Those of skill in the art, in light of these examples, should appreciate that many changes can be made to the foregoing disclosure without departing from the spirit and scope of the inventions disclosed.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

EXAMPLES

Example 1

This example illustrates the construction of a nucleotide sequence that functions to achieve expression of an ET29 protein in maize plant cells.

ET29 is a protein derived from *B. thuringiensis* and has been previously shown to exhibit corn rootworm insecticidal biological activity when provided in the diet to corn rootworm larvae (U.S. Pat. Nos. 6,093,695; 6,537,756; 6,686,452). Native Bt coding sequences have been shown to exhibit unacceptable levels of protein synthesis when expressed in plant cells (U.S. Pat. No. 5,500,365). Expression of ET29 protein in corn plant cells, and specifically in cells of corn roots, could provide corn plants with protection from corn rootworm feeding damage. Accordingly, a nucleotide sequence encoding a *B. thuringiensis* ET29 insecticidal protein was constructed that was anticipated to be more highly expressed in plants, avoiding certain inimical nucleotide sequences that have been previously shown to be problematic, while maintaining a nucleotide sequence that encodes the native insecticidal protein with one exception; a supplemental Alanine codon at position two (2) of the coding sequence (SEQ ID NO:13) was included in the synthetic sequence to facilitate ease of cloning. The ALA2 variant ET29 amino acid sequence as set forth at SEQ ID NO:14 has been designated as TIC809 and in bioassays exhibits no less biological activity than the native ET29.

The TIC809 coding region as set forth in SEQ ID NO:13 was subcloned into a binary plant transformation vector. Elements upstream of the TIC809 coding region included a enhanced CaMV 35S promoter, a wheat major chlorophyll a/b-binding protein 5' untranslated leader sequence, a rice actin 1 gene first intron and flanking untranslated leader region (UTL) exon sequence, and, optionally, a maize ribulose 1,5-bisphosphate carboxylase small subunit chloroplast transit peptide coding sequence. In planta expression of a fusion protein consisting of the chloroplast transit peptide (ctp) linked to the N-terminus of the TIC809 protein enables targeting of the TIC809 protein into plastids. A wheat hsp17 3' untranslated region (UTR) was incorporated downstream of the TIC809 to achieve transcription termination and polyadenylation of mRNA transcripts.

Plant transformation vectors contain a glyphosate tolerance selectable marker. The plant transformation vector pMON70513 provides for expression of a cytoplasm soluble TIC809 protein while pMON70514 provides for expression of a plastid targeted TIC809 protein.

Example 2

This example illustrates the comparison of plastid targeted versus non-targeted expression of TIC809 in transient corn protoplast assays, and the subsequent analysis of transgenic plants transformed to express the TIC809 protein targeted to maize plastids.

Transient expression assays using corn protoplasts transformed with either pMON70513 or pMON70514 were compared to each other and to an empty vector control. The results indicated low levels of expression of the untargeted TIC809 protein compared to the targeted TIC809 protein. Accordingly, only pMON70514 was analyzed further. Transgenic corn events were produced after *Agrobacterium*-mediated transformation of corn protoplasts. Regenerated corn plants ("R0 plants") were screened for glyphosate tolerance and the copy number of the wheat hsp17 (tahsp17) 3' UTR. Six-leaf stage (V6) root and leaf samples from each transgenic corn event were screened for the presence and amount of ET29 protein using an ELISA method.

Nineteen (19) out of eighty-seven (87) transgenic events analyzed by ELISA displayed a distinctive abnormal phenotype characterized by a chlorotic stalk, and eight (8) of these exhibited tassel or ear abnormalities. The average TIC809 expression level in leaf and root tissue from plants exhibiting an abnormal phenotype was 2.2 and 2.0 parts per million, respectively. The average TIC809 levels in leaf and root from phenotypically normal plants was 1.4 and 1.1 ppm, respectively. These results suggested that higher levels of TIC809 protein may be correlated with the observed abnormal phenotypes.

Example 3

This example illustrates cloning of a gene encoding TIC810, a protein expressed from within an operon in *Bacillus thuringiensis* in which the ET29 (tic809) gene also resides, and the identification that expression of TIC810 exhibits no corn rootworm insecticidal bioactivity.

et29 was originally cloned on a 7.1 kb EcoRI fragment from DNA obtained from *B. thuringiensis* strain EG4096 (U.S. Pat. No. 6,686,452), and was retained in plasmid pEG1303, a shuttle vector capable of replication in *B. thuringiensis* and in *E. coli*. Recombinant *B. thuringiensis* strain EG11502 containing pEG1303 produces low levels of ET29 crystal protein when grown in C2 medium (Donovan et al, *Mol. Gen. Genet.* 214: 365-372, 1988).

The ET29 coding sequence was subcloned from the large 7.1 EcoRI fragment in pEG1303 as a ~1.5 kb KpnI-ClaI fragment into the high copy-number shuttle vector pEG854.9 (Baum et al, (1996) Appl. Env. Microbiol. 62:4367-4373) with the expectation that an increase in the level of ET29 expression would be observed from the smaller fragment. The resulting plasmid, pMON78402, was believed to contain sufficient native DNA 5' and 3' of the ET29 coding region to incorporate any necessary expression elements such as a sporulation dependent promoter. Surprisingly, no protein crystal formation was detected when pMON78402 was introduced into the acrystalliferous *B. thuringiensis* host strain EG10650, suggesting that the 5' region present on pMON78402 may not contain the native ET29 promoter and that ET29 transcription from the clone in pEG1303 was driven from a fortuitous vector-borne promoter. Furthermore, sequencing of the entire 7.1 kb EcoRI fragment in pEG1303 revealed the presence of an interrupted open reading frame immediately upstream of the ET29 coding region. The interrupted coding region contained one of the terminal EcoRI sites used to clone the 7.1 kb EcoRI fragment in pEG1303. A FASTX search of the existing non-redundant protein databases as well as a database of *B. thuringiensis* crystal protein sequences suggested that this partial coding region encodes an amino acid sequence exhibiting approximately 36% sequence identity to that of the ET29 protein. This related protein was designated TIC810. This suggested that the ET29 gene resided within an uncharacterized operon that included at least the upstream TIC810 gene, and that since TIC810 was probably co-expressed with ET29, it too might also exhibit corn rootworm insecticidal activity.

The native ET29 coding sequence is set forth at SEQ ID NO:9 from position 716 through 1408. A single NheI site was present within this coding sequence (nucleotides 820-825 as set forth at SEQ ID NO:9). The partial TIC810 coding sequence in pEG1303 is shown as set forth at SEQ ID NO:9 from nucleotide position 369 to 654. The EcoRI site that bisected the TIC810 coding sequence is set forth at SEQ ID NO:9 at nucleotides 369-374. NheI digestion of EG4096 DNA or digestion with NheI and compatible restriction enzymes coupled with ligation and inverse PCR allowed for the identification of the nucleotide sequence of the 5' end of the TIC810 coding region.

EG4096 genomic DNA (5 μg) was digested in 50 μL volumes with compatible restriction enzymes in various combinations that include NheI, NheI+BlnI, NheI+SpeI, and NheI+XbaI. Ten microliters of the complete digests were mixed with 80 μL sterile water, 10 μL 10× ligase buffer (New England BioLabs, Beverly, Mass.) and 2 μL T4 ligase and incubated overnight at 4C. The ligation products were used as thermal amplification templates using an Elongase® kit from Invitrogen (Carlsbad, Calif.) and the divergent primers pr370 and pr371 (as set forth at SEQ ID NO:21 and SEQ ID NO. 22 respectively). SEQ ID NO:21 corresponds to the reverse complement of nucleotides 650-671 as set forth in SEQ ID NO:9, and SEQ ID NO:22 corresponds to nucleotides 744-764 as set forth in SEQ ID NO:9.

Restriction enzymes used for each reaction produced compatible ends. *B. thuringiensis* DNA is AT-rich, and so it was anticipated that the restriction enzymes SpeI and XbaI would yield smaller PCR products than the BlnI and NheI restriction enzymes. Only the SpeI-NheI and XbaI-NheI combinations yielded amplified DNA fragments. The amplified DNA fragments were cloned and sequenced and assembled with the EcoRI-NheI segment consisting of nucleotides 369-825 as set forth at SEQ ID NO:9. An assembled sequence predicted to encode TIC810 was identified as set forth at SEQ ID NO:3. The TIC810 gene was subsequently amplified directly from EG4096 genomic DNA using a high-fidelity thermostable polymerase. Multiple clones were used to confirm the sequence. The TIC810 gene is predicted to encode a ~25,000 Dalton protein as set forth in SEQ ID NO:4. The deduced TIC810 amino acid sequence exhibits about 33% amino acid sequence identity to the ET29 amino acid sequence, suggesting that TIC810 may also exhibit insecticidal bioactivity.

The expression of TIC810 in an acrystalliferous strain of *B. thuringiensis* was examined. The TIC810 gene was amplified using primers pr375 and pr376 (as set forth in SEQ ID NO:23 and SEQ ID NO:24, respectively), producing an amplicon encoding a TIC810 amino acid sequence variant that contains an ATG translation initiation codon substituted for the native GTG codon. Primer pr375 also incorporates a SpeI site 5' to the TIC810 coding region while primer pr376 incorporates an XhoI site 3' to the TIC810 coding region amplicon, permitting subcloning of the amplicon into the *B. thuringiensis-E. coli* shuttle vector pMON47407. The amplicon encoding TIC810 was inserted into this vector just down stream of a vector-endogenous cry1A promoter. Sequences positioned downstream of the cry1A promoter exhibit sporulation-dependent expression in *B. thuringiensis*. The resulting recombinant plasmid pMON78409 containing the sequence encoding the TIC810 protein was introduced into the acrystalliferous *B. thuringiensis* host strain EG10650 by electroporation to generate the recombinant *B. thuringiensis* strain SIC8116. Strain SIC8116 produced parasporal inclusion bodies containing TIC810 protein when grown in C2 sporulation medium. No insecticidal bioactivity was observed when corn rootworm larvae were exposed to artificial media overlaid with sporulated cultures of SIC8116, suggesting that the TIC810 protein did not exhibit insecticidal bioactivity directed to CRW.

Example 4

This example illustrates that ET29 expression under the control of a cry1A sporulation dependent promoter results in poor expression levels and aberrant physiological host cell behavior.

The recombinant *B. thuringiensis* strain EG11502, containing the plasmid pEG1303, produced small amounts of the ET29 crystal protein. In an attempt to increase the expression of ET29 in *B. thuringiensis*, the ET29 coding sequence was inserted into the *B. thuringiensis-E. coli* shuttle vector pMON47407. The ET29 coding sequence was amplified from pEG1303 DNA using primers pr365 and pr372 (SEQ ID NO:25 and SEQ ID NO:26, respectively). Following sequence confirmation, the amplified ET29 gene fragment was inserted into the pMON47407 vector backbone in an orientation effective for expression of ET29 from the vector-endogenous cry1A promoter. To assess ET29 protein production, the resulting recombinant plasmid, pIC17507, was introduced into *B. thuringiensis* strain EG10650, to produce the recombinant strain SIC8114. Strain SIC8114 produced a lower amount of ET29 protein than did the original ET29 recombinant strain EG11502 and exhibited poor sporulation in C2 sporulation medium. This result suggested that overexpression of ET29 may be detrimental to the host cell, or that some other factor present in the native strain EG4096 and not in the recombinant strain was required for efficient expression and/or accumulation of ET29.

Example 5

This example illustrates the identification of an operon exhibiting homology to the TIC810/ET29 operon.

Other strains of Bt were examined by Southern blot analysis for the presence of sequences related to the TIC810/ET29 operon in EG4096. A 5.4 kb ClaI restriction fragment from Bt strain EG5078 total DNA was found to hybridize to an ET29-specific hybridization probe. This 5.4 kb ClaI fragment was cloned into the *B. thuringiensis-E. coli* shuttle vector pEG854 (Baum et al., (1990) Appl. Env. Microbiol. 56:3420-3428) and also into the *E. coli* vector pBluescript IISK to generate the recombinant plasmids pEG1325 and pEG1323, respectively. Sequence analysis of the 5.4 kb insert revealed two tightly linked genes similar to the ET29 and TIC810 genes in *B. thuringiensis* strain EG4096. The 5' proximal coding sequence was designated as tic812 (as set forth in SEQ ID NO:5) and was predicted to encode a TIC812 polypeptide (as set forth in SEQ ID NO:6). TIC812 exhibits about 97% amino acid sequence identity to the TIC810 protein. The 3' proximal coding sequence was designated as et37 (SEQ ID NO:1) and was predicted to encode the ET37 amino acid sequence as set forth in SEQ ID NO:2. ET37 exhibits greater than about 99% amino acid sequence identity to the ET29 protein, differing only at one amino acid position.

The shuttle vector pEG1325, containing both the TIC812 and ET37 genes, was introduced into the acrystalliferous *B. thuringiensis* host strain EG10650 using an electroporation procedure. The resulting recombinant strain, EG11541, produced a high level of the ET37 protein when grown in C2 sporulation medium. However, the amount of TIC812 protein present in the spores was approximately only 25% of the amount of ET37 protein. The ET37/TIC812 protein mixture produced by strain EG5078 was found to be toxic to corn rootworm larvae when tested in bioassay.

Because of the similarity between the TIC810/ET29 and the TIC812/ET37 operons, and because ET37 and ET29 differ at only one amino acid position, it is unlikely that the two proteins exhibit significantly different insecticidal or cytotoxic properties. The low level of ET29 when expressed alone compared to the greater level of ET37 protein when expressed from its native operon, coupled with the substantial identity between the TIC810 and TIC812 proteins, suggests that the TIC810 and TIC812 proteins may be playing a role in increasing the levels of, or providing some stabilization to, their respective ET29 or ET37 proteins. Therefore, co-expression of TIC812 along with the ET37 protein may be the cause of the observed overproduction of ET37 in strain EG11541. Also, co-expression of TIC810 and ET29 may likewise result in overproduction of ET29.

To test this hypothesis, the individual ET29, ET37, TIC810 and TIC812 coding sequences were amplified and cloned into the *B. thuringiensis* expression vector pMON47407 described above, so that expression of each was under the control of the vector-endogenous cry1A promoter. The naturally occurring GTG codon at position 1 of the TIC812 coding sequence was modified to an ATG codon. The TIC810-ET29 tandem coding sequences (SEQ ID NO:9) and the TIC812-ET37 tandem coding sequences (SEQ ID NO:10) were each amplified from genomic DNA and cloned into the TOPO cloning vector pCR2.1-TOPO (Invitrogen, Carlsbad, Calif.) and their sequences confirmed. The amplified DNA fragments were then cloned into the vector pMON47407 so that the tandem coding sequences were under the control of the vector-endogenous cry1A promoter. Thus, each insert was cloned into pMON47407 in the same orientation and employed the same promoter. The acrystalliferous *B. thuringiensis* strain EG10650 was used as the host strain for all expression studies. The plasmid constructs and recombinant *B. thuringiensis* strains containing these plasmids are listed in Table 2.

TABLE 2

Plasmids Constructed for Expression Analysis of TIC810/ET29 and TIC812/ET37

| Strain | Coding Sequence(s) | Plasmid | Primer pair[1] |
|---|---|---|---|
| EG10650 | — | — | — |
| SIC8114 | ET29 | pIC17057 | pr372-pr365 |
| SIC8116 | TIC810 | pMON78409 | pr375-pr376 |
| SIC8130 | ET37 | pMON78404 | pr372-pr365 |
| SIC8131 | TIC812 | pMON78405 | pr375-pr376 |
| SIC8134 | TIC810_ET29 | pMON78406 | pr421-pr365 |
| SIC8135 | TIC812_ET37 | pMON78407 | pr421-pr365 |

[1]primer pair used for amplification of the coding sequence inserted into pMON47407

The recombinant strains and EG10650 were each grown in 30 milliliters of C2 medium in a 250 milliliter baffled flask for 3 days at 28C with vigorous agitation. Spores and crystals were collected by low-speed centrifugation, washed once with 30 milliliters of wash buffer (10 mM Tris-HCl, 0.1 mM EDTA, 0.005% Triton X-100, pH 6.8), and resuspended in wash buffer at a final volume of 3 milliliters. These 10× C2 concentrates were then analyzed by SDS-PAGE. Protein concentrations were determined by densitometry using BSA as a standard.

SDS-PAGE analysis indicated that 1) both ET29 and ET37 exhibited poor production when expressed alone; 2) both TIC810 and TIC812 accumulated to high levels when expressed alone; and 3) ET29 and ET37 exhibited dramatically elevated levels of expression when co-expressed along with TIC810 or TIC812, respectively. ET29 protein production was about 4.6 fold higher in the presence of TIC810 than in its absence, and ET37 production was about 6.6 fold higher in the presence of TIC812 than in its absence. Furthermore, strains SIC8134 containing the TIC810_ET29 tandem coding sequence and SIC8135 containing TIC812_ET37 tandem coding sequence exhibited normal sporulation and lysis. These results indicated that TIC810 and TIC812 were required for the high-level production of ET29 and ET37 in *B. thuringiensis*, respectively, and may be acting as accessory or chaperone proteins.

The 10×TIC812/ET37 spore-crystal suspension was used directly in a bioassay against WCR. Crystal proteins in the suspensions were quantified by SDS-polyacrylamide gel electrophoresis and densitometry using bovine serum albumin as a standard. 200 mL of WCR diet was prepared in a manner similar to that described by Pleau et al. (*Entomol. Exp. Appl.* 105:1-11, 2002). Twenty μL of test sample were applied per well and allowed to dry before applying a single neonate insect larvae per well with a fine bristle paintbrush. Plates were sealed with mylar and ventilated using an insect pin. Twenty-four larvae were tested per sample concentration. The bioassay plates were incubated at 27C, 60% RH, in complete darkness for 5-7 days. The number of surviving larvae per treatment was recorded at the end of 5-7 days, depending on the experiment. Surviving larvae were weighed on a microbalance (Cahn C-33). Data were analyzed using JMP® 4 statistical software (SAS Institute, Cary, N.C., USA). The bioassay data are listed in Table 3.

The results suggest that sporulated cultures of wild type *B. thuringiensis* strain EG5078 containing a mixture of ET37 and TIC812 were found to be toxic to Western corn rootworm larvae, causing significant larval mass reduction when compared to the control. A comparable 10× spore suspension from the cry-*B. thuringiensis* host strain EG10650 exhibited no activity against WCR larvae in bioassay. A sample containing 500 mg Cry3Bb rootworm insecticidal protein was included as a positive control.

TABLE 3

Western Corn Rootworm Bioassay vs ET37/TIC812

| Sample | Concentration[1] | N | Mean | SD[2] | SEM | LO 95% | UP 95% | P > \|t\| |
|---|---|---|---|---|---|---|---|---|
| UTC[3] | 0.250 | 6 | 0.36 | 0.05 | 0.02 | 0.31 | 0.41 | |
| Cry3Bb | 0.500 | 3 | 0.20 | 0.03 | 0.02 | 0.13 | 0.26 | 0.0003 |
| TIC812-ET37 | 1.000 | 3 | 0.16 | 0.04 | 0.03 | 0.05 | 0.27 | <0.0001 |
| TIC812-ET37 | 0.500 | 3 | 0.19 | 0.08 | 0.05 | −0.01 | 0.39 | 0.0002 |
| TIC812-ET37 | 0.250 | 3 | 0.25 | 0.01 | 0.01 | 0.22 | 0.29 | 0.0084 |
| TIC812-ET37 | 0.125 | 3 | 0.25 | 0.08 | 0.04 | 0.06 | 0.44 | 0.0073 |

[1]mg/ml;
[2]Standard Deviation;
[3]untreated check;
Variances not equal, Levene's method, P > F 0.0053;
There is an effect due to treatment, SLS, P > F 0.0002; and
Means with a P value < 0.05 are significantly different from UTC, Planned Contrasts.

Example 6

This example illustrates the co-expression of TIC810 and TIC809 proteins in corn protoplasts.

Synthetic nucleotide sequences encoding the *B. thuringiensis* TIC810 and ET29 (TIC809) proteins were constructed for expression in plants. The synthetic sequence encoding TIC809 is set forth at SEQ ID NO:13 and the amino acid sequence translation is set forth at SEQ ID NO:14. The synthetic sequence encoding TIC810 is set forth at SEQ ID NO:15, and the amino acid sequence translation is set forth at SEQ ID NO:16. The synthetic coding sequences for TIC809 and TIC810 were cloned into expression vectors for transient expression studies with corn protoplasts. Genetic elements around the coding region(s) of the TIC809 and TIC810 coding sequences were identical, except for the addition of the chloroplast transit peptide (ctp), as described in Example 1. The plasmid constructs are described in part in Table 4 below.

TABLE 4

Plasmid Constructs for Transient Assay of TIC810/TIC809 Expression

| Plasmid | Encoded Cry Protein (s) | Protein Localization |
|---|---|---|
| pMON84202 | TIC809 | Untargeted |
| pMON84203 | ctp-TIC809 | Targeted to chloroplasts |

TABLE 4-continued

Plasmid Constructs for Transient Assay of TIC810/TIC809 Expression

| Plasmid | Encoded Cry Protein (s) | Protein Localization |
|---|---|---|
| pMON64134 | TIC809, TIC810 | Untargeted |
| pMON64135 | ctp-TIC809, ctp-TIC810 | Targeted to chloroplasts |
| pMON64136 | TIC809, ctp-TIC810 | TIC809 untargeted; TIC810 targeted to chloroplasts |
| pMON64137 | ctp-TIC809, TIC810 | TIC809 targeted to chloroplasts; TIC810 untargeted |

Protoplasts were prepared by digesting 12-day corn leaf tissue in 0.6 M mannitol, 10 mM MES pH 5.7, 2% cellulase RS, and 0.3% macerozyme R10 for 2 hours. All transformations were performed using 50 μg DNA and $1.3\times10^6$ cells.

TIC809 expression in protoplasts was measured using an ELISA with polyclonal antibodies raised against the ET29 protein. Results are shown in Table 5 and represent the average of three duplicate samples.

TABLE 5

Transient expression of TIC809 in corn protoplasts

| Plasmid | Cry Proteins | Mean[2] | Standard Error | Comparisons[1] |
|---|---|---|---|---|
| pMON84202 | TIC809 | 5.1 | 0.6 | c |
| pMON64134 | TIC809, TIC810 | 120.3 | 24.9 | a |
| pMON64136 | TIC809, ctpTIC810 | 29.2 | 3.0 | bc |
| pMON84203 | ctpTIC809 | 111.4 | 3.2 | a |
| pMON64137 | ctpTIC809, TIC810 | 90.2 | 18.0 | ab |
| pMON64135 | ctpTIC809, ctpTIC810 | 148.9 | 15.2 | a |

[1]Comparisons for all pairs using Tukey-Kramer HSD, alpha = 0.05. Treatments with the same letter are not significantly different from each other.
[2](ng ET29/mg total protein)

The results indicate that the chloroplast targeted TIC809 protein resulted in an increase in TIC809 expression in the transient system compared to the non-targeted TIC809 expression. By comparing expression from pMON84203 with expression from pMON84202, targeted TIC809 protein expression is observed to be approximately 20-fold higher than that of the untargeted TIC809 protein. However, co-expression of the untargeted TIC810 protein with the untargeted TIC809 also results in a significant increase in the expression of TIC809 protein (compare pMON64134 with pMON84202). In five out six experiments, targeting both TIC810 and TIC809 to the plastid resulted in equivalent or greater levels of expression and accumulation of TIC809 compared to that amount accumulated when TIC809 is targeted to the plastid alone. In any event, co-expression of TIC809 and TIC810 together in any common cellular location results in increased levels of accumulation of TIC809 compared to levels of TIC809 accumulation when expressed in that compartment in the absence of TIC810.

pMON64136 and pMON64137 were constructed to test the effect of expression of TIC809 when localized to a different subcellular compartment from TIC810. Targeting TIC810 to the plastid had no significant impact on the expression of the non-targeted TIC809 (compare pMON64136 with pMON84202). Similarly, the non-targeted TIC810 had no significant impact on the accumulation of the targeted TIC809 (compare pMON64137 with pMON84203). However, the non-targeted TIC810 increased or stabilized the accumulation of the non-targeted TIC809. These results suggest that localization of the two proteins to the same space within the cell results in a greater accumulation of the rootworm insecticidal protein TIC809, perhaps as a result of some interaction between the proteins, stabilizing the accumulation of the TIC809 protein. These results are consistent with the observation that co-expression of TIC810 and ET29, or co-expression of TIC812 and ET37, results in high-level expression of ET29 or ET37 respectively in *B. thuringiensis.*

A plasmid containing a luciferase (LUX) gene was included as a control in the transient protoplast expression assays. Although luciferase is generally included in transient assays as an indicator of transformation efficiency, it was observed that luciferase expression levels varied widely depending on the plasmid construct tested, presumably due to phytotoxic effects of the accumulated Bt proteins. Low accumulation of TIC809 was correlated with low luciferase levels. In each case, other than when TIC809 is localized to the chloroplast, co-expression of the untargeted TIC810 in the same compartment with TIC809 resulted in a dramatic increase in both luciferase and TIC809 expression levels (compare pMON64134 with pMON84202). The luciferase data is shown in Table 6.

TABLE 6

Luciferase levels in transient assay experiment

| Plasmid | Encoded Cry protein(s) | Counts per second | Standard error of the mean | Comparisons[1] |
|---|---|---|---|---|
| pMON84202 | TIC809 | 67.4 | 1.7 | b |
| pMON64134 | TIC809, TIC810 | 518.6 | 135.7 | a |
| pMON64136 | TIC809, ctpTIC810 | 70.8 | 2.3 | b |
| pMON84203 | ctpTIC809 | 408.0 | 84.7 | a |
| pMON64137 | ctpTIC809, TIC810 | 277.2 | 2.6 | ab |
| pMON64135 | ctpTIC809, ctpTIC810 | 284.9 | 32.8 | ab |

[1]Comparisons for all pairs using Tukey-Kramer HSD, alpha = 0.05. Treatments with the same letter are not significantly different from each other.

Example 7

This example illustrates the results of co-expression of TIC810 and TIC809 in transgenic corn.

TIC809, ctp-TIC809, TIC809-TIC810, and ctpTIC809-ctpTIC810 expression cassettes were introduced into binary plant transformation vectors suitable for use in corn transformation. Other than the sequences encoding the Bt proteins, constructs differ from each other only with respect to the presence or absence of a chloroplast-targeting peptide coding sequence. A gene conferring glyphosate tolerance was used as a selectable marker for *Agrobacterium*-mediated transformation.

pMON64138 contains a cassette for in planta expression of TIC809 and TIC810. pMON64139 contains a cassette for in planta expression of chloroplast targeted TIC809 and chloroplast targeted TIC810. pMON70513 contains a cassette for in planta expression of TIC809. pMON70514 contains a cassette for in planta expression of a chloroplast targeted TIC809. Regenerated transgenic corn plants obtained after transformation using these four plasmids and glyphosate selection were screened using a TaqMan® assay for the presence of the glyphosate selectable marker gene and the presence of the tahsp17 3' sequence(s). An endpoint PCR assay was used to confirm the presence of the TIC809 and/or TIC810 coding sequences, where relevant, in each event. Events transformed with constructs containing both TIC809 and TIC810 were expected to exhibit two copies of the tahsp17 3' sequence because each coding sequence is bordered on its 3' end by the tahsp17 3' element. Transgenic and control plants containing six leaves (V6 stage) and roots were assayed using an ET29 ELISA to determine the level of accumulation of TIC809.

Plants regenerated after transformation with pMON70513 containing only the cytoplasm targeted TIC809 coding sequence behaved as indicated above in examples 1 and 2. Plants exhibited substantially abnormal phenotypes and characteristics, typically characterized visually by a chlorotic stalk, among other abnormalities. The TIC809 expression and/or accumulation levels averaged no more than about 2.0 ppm in root tissue.

Fifteen R0 plants transformed with pMON64138 were assayed for the presence of the glyphosate marker and the presence and copy number of the tahsp17 3' elements, as well as for the presence of the OriV for detection of any vector backbone, and for the presence and intactness of the genes encoding the cytoplasm targeted TIC809 and TIC810 proteins. One event did not contain the full length TIC809 coding sequence and was also determined to exhibit undetectable levels of TIC809 protein. The remaining 14 events displayed an average of about 12 ppm TIC809 (fresh weight) in leaf tissue or root tissue. The levels of TIC809 in root tissue ranged from about 0.2 ppm in one plant to about 45 ppm in the plant exhibiting the greatest level of expression and/or accumulation. This result suggested that the co-expression of TIC810 along with TIC809 in the plant tissues provides for improved levels of expression and/or accumulation of the TIC809 protein. More significantly, abnormal phenotypes were not observed in the plants expressing both TIC809 and TIC810 in the cytoplasm. The expression level of TIC809 was more uniform in root tissue, than in leaf tissue, and more plants exhibited higher levels of TIC809 expression in the roots than in the leaves.

Fifteen R0 plants were regenerated from transformed plant cells using pMON64139 containing the chloroplast targeted TIC809 and TIC810 coding sequences. One event was identified in the screening analysis that did not contain the full length TIC809 expression cassette, and also did not exhibit detectable levels of TIC809 protein. The remaining 14 events averaged about 4.4 ppm and about 8.6 ppm TIC809 protein in root and leaf tissue respectively. The levels of TIC809 in roots ranged from about 0.2 ppm to about 45 ppm. Corn plants transformed with pMON70514, containing the ctpTIC809 gene, averaged only about 1.7 ppm TIC809 protein in leaf tissue and about 6.3 ppm TIC809 protein in root tissue. Thus, co-expression of the non-targeted TIC810 along with the -targeted TIC809 resulted in higher levels of TIC809 expression and/or accumulation than was achieved with the chloroplast-targeted TIC809 protein. Furthermore, the R0 plants producing elevated levels of TIC809 protein did not exhibit stalk chlorosis or other manifestations of phytotoxicity associated with in planta expression of the TIC809 protein alone. Co-expression of chloroplast targeted TIC810 along with chloroplast targeted TIC809 also resulted in increased levels of TIC809 accumulation when compared to levels of chloroplast targeted TIC809 protein expressed in the absence of TIC810.

Eighteen R0 plants transformed to co-express the targeted TIC809 and targeted TIC810 proteins were assayed for the glyphosate tolerance selectable marker gene, the tahsp17 3' copy number, presence of OriV (backbone), and for intact TIC809 and TIC810 coding sequences. One event did not contain an intact TIC809 coding sequence and failed to exhibit detectable levels of TIC809 protein. The remaining 17 plants averaged 8.6 and 4.4 ppm TIC809 protein in leaf and in root, respectively. Root expression of TIC809 protein ranged from about 1 ppm to about 9 ppm. Events exhibiting chloroplast targeted TIC809 and TIC810 protein expression failed to exhibit stalk chlorosis or other manifestations of phytotoxicity associated with in planta expression of the TIC809 protein alone.

Example 8

This example illustrates maize root enhanced expression of plastid targeted TIC809.

pMON64144 was constructed to contain a chloroplast targeted TIC809 under the operable control of a RCc3 root promoter (U.S. patent application Ser. No. 11/075,113) and flanked 5' of a CTP coding sequence by a maize heat shock protein HSP70 intron and 3' of the TIC809 coding sequence by a wheat hsp17 3' transcription termination and polyadenylation sequence. The sequence of the expression cassette is set forth at SEQ ID NO:38.

Corn plants were regenerated after *Agrobacterium* mediated transformation of corn tissue with the vector pMON64144. Regenerated corn plants were screened using a TaqMan® assay for the presence of the glyphosate selectable marker and the wheat 3' flanking sequence. The presence of intact TIC809 coding sequence was confirmed using end-point PCR assay. Root and leaf samples from 23 R0 corn plants at the six-leaf stage were screened using an ET29 ELISA.

The average level of TIC809 accumulated in root tissue was 0.4 ppm. No TIC809 protein was detected in leaves, suggesting that RCc3 promoter activity is enhanced in root cells. 8 of the 23 R0 plants exhibited a TIC809 protein concentration below the level of detection in root. None of the plants tested exhibited levels greater than about 1 ppm TIC809. In contrast, a similar construct under the control of a e35S promoter exhibited on average about 1.4 ppm TIC809 protein in root tissue and about 1.7 ppm in leaves (n=87).

Example 9

This example illustrates in planta co-expression of TIC809 and TIC810, each under the control of different promoters.

In Example 7 the TIC809 and TIC810 genes were each expressed in planta from separate expression cassettes, expression of each coding sequence being driven from separate but identical e35S promoters. In this example expression cassettes were designed so that expression of TIC809 was substantially localized to the root tissue using a RCc3 promoter, while expression of TIC810 was under the control of an e35S promoter.

pMON64150 contains two expression cassettes. One cassette (SEQ ID NO:40) contained a chloroplast targeted TIC809 coding sequence operably linked at its 5' end to a rice RCc3 promoter and a maize heat shock protein HSP70 intron, and at its 3' end to a wheat hsp17 3' transcription termination and polyadenylation sequence. The other cassette (SEQ ID NO:40) contained a chloroplast targeted TIC810 coding sequence operably linked at its 5' end to an e35S promoter and a rice actin intron sequence, and at its 3' end to a wheat hsp17 3' transcription termination and polyadenylation sequence.

pMON64151 is identical to pMON64150 except that the coding sequences in the two expression cassettes lack the chloroplast targeting peptide coding sequence (SEQ ID NO:43 and SEQ ID NO:40, respectively).

Plants regenerated from corn tissue transformed with either pMON64150 or pMON64151 were tested to confirm the presence and intactness of the TIC809 and TIC810 coding sequences. Leaves and roots from these events were tested at the 6 leaf stage using an ET29 ELISA to determine the levels of TIC809 protein accumulation. Plants transformed with pMON64150 exhibited on average about 1.5 ppm TIC809 per plant, while plants transformed with pMON64151 exhibited on average about 0.4 pm TIC809 per plant. pMON64150 plants exhibited TIC809 root accumulation levels from about 0.4 to about 6 ppm, with more than two thirds of the events exhibiting TIC809 levels at least about 1 ppm. Leaf tissue consistently exhibited levels of TIC809 accumulation below the limits of detection for the assay.

Average root accumulation of TIC809 was greater in pMON64151 events than in events generated using the chloroplast targeted pMON64150 expression cassettes (pMON64151, 6.6 ppm vs pMON64150, 1.4 ppm). These results are consistent with the results obtained using constructs in which TIC809 was expressed from the e35S promoter (pMON64138 and pMON64139). The greatest difference between plants expressing TIC809 from the RCc3 versus the e35S promoter was the lack of accumulation of TIC809 in leaves when expression was controlled by the RCc3 promoter. Both pMON64150 and pMON64151 events exhibited normal phenotypes.

Example 10

This example illustrates Hemipteran species insecticidal bioactivity of compositions comprising TIC 809 and TIC 810, and homologs thereof as disclosed herein.

Compositions comprising ET29 and/or TIC809 or ET37 have been disclosed herein to be insecticidal to Coleopteran species of insect pests. TIC810 and TIC812 have not demonstrated insecticidal bioactivity to Coleopteran insect species, but as disclosed herein, are useful for facilitating the high level expression and stability of ET29 and or TIC809 and ET37. ET29 had also previously demonstrated insecticidal bioactivity directed to *Ctenocephalides* species, and it is anticipated that ET37 would also demonstrate activity to this species. It was speculated that TIC810 and/or TIC812 also exhibit insecticidal bioactivity and so these proteins were tested in bioassay against other plant pests, for example against Hemipteran insect pest species such as *Lygus hesperus* (Western Tarnished Plant Bug; WTPB).

The WTPB, is a phytophagous, piercing-sucking insect that attacks numerous weeds and crops. The WTPB damages agricultural crops, including cotton, by direct feeding damage. An assay for testing insecticidal compositions using this class of insects must allow for the insect's natural feeding behavior. The feeding assay employed is based on a 96 well micro-titer plate format using a sachet system as described by Habibi et al., (*Archives of Insect Biochem. and Phys.* 50: 62-74 (2002)). The WTPB artificial diet is supplied by Bio-Serv® (Bio-Serv® Diet F9644B, Frenchtown, N.J.).

Five hundred and eighteen milliliters of autoclaved, boiling water are combined with 156.3 grams of Bio-Serv® Diet F9644B in a surface sterilized blender. The contents of four surface sterilized chicken eggs are added and the mixture is blended until smooth, then adjusted to one liter total volume and allowed to cool. Toxin samples are prepared by mixing twenty microliters of sample in the desired concentration with two hundred microliters of blended diet (1:10). Depending upon the number of individual samples desired for testing this amount can be scaled up or down.

A sheet of Parafilm® (Pechiney Plastic Packing, Chicago, Ill.) is placed over a vacuum manifold designed for 96-well format (Analytical Research Systems, Gainesville, Fla.) and a vacuum of approximately −20 millimeters mercury is applied, which is sufficient to cause extrusion of the Parafilm® into the wells. Forty microliters of test sample are added to the Parafilm® wells. A sheet of Mylar film (Clear Lam Packaging, Inc., Elk Grove Village, Ill.) is then placed over the Parafilm® and sealed gently with a tacking iron (Bienfang Sealector II, Hunt Corporation, Philadelphia, Pa.). The Parafilm® sachets are then placed over a flat-bottom 96-well plate containing WTPB eggs suspended in agarose. Upon hatching, WTPB nymphs will feed by piercing the sachet that is presented above them. Extraoral digestion as a result of extrusion of WTPB oral secretions into the sachet may lead to proteolysis and degradation of diet contents prior to ingestion by the insect. To assure intact protein was being presented to the insect in its diet, the diet sachets are replaced every two days. This enhancement allows for longer presentation of the intact diet contents over the course of the feeding assay. Insect diet sachets are replaced on days two, four and six. Stunting and mortality scores are determined on day 8 and compared to the untreated check (UTC).

The proteins ET29 (or TIC809), TIC810, ET37 and TIC812 (U.S. Patent Application No. 60/713,111), were tested individually and in combinations such as, for example, TIC809 plus TIC810, for their toxicity to the WTPB. Crystal proteins were expressed in the acrystalliferous *Bacillus thuringiensis* strain EG10650 and purified over sucrose step gradients to eliminate spores and cell debris. Sucrose step gradients (10 mL each of 55-, 70- and 79-% sucrose in 10 mM Tris-HCl, 0.1 mM EDTA, 0.005% Triton X-100, pH 7.5) were prepared in 25-by 89-mm Ultra-Clear centrifuge tubes (Beckman Instruments, Inc., Palo Alto, Calif.). Spore-crystal suspensions were layered on top of the gradients and centrifuged at 18,000 rpm (4° C.) for 4-18 hr in an ultracentrifuge equipped with a SW28 rotor. Protein crystals were recovered from either the 55-70% or the 70-79% sucrose interface and suspended in 25 mM Tris-HCl pH 7.5. Initial bioassays contained the purified Bt insecticidal proteins at a final concentration of 200 parts per million (ppm). The Coleopteran specific toxin, Cry3Bb1 (Donovan et al., Appl. Environ. Microbiol. 58: 3921-3927 (1992)), the Lepidopteran specific toxin Cry1Ac (Baum et al., Appl. Environ. Microbiol. 56:3420-3428 (1990), and the Lepidopteran specific toxin Cry1Bb1 (U.S. Pat. No. 5,322,687) were each included as negative controls in the feeding assay. Surprisingly, WTPB nymphs exhibited stunting and mortality when exposed to the combination of the TIC810 plus ET29 proteins and as expected, no stunting and mortality were detected when exposed only to ET29, or to any of the other BT proteins Cry3Bb1, Cry1Ac, or Cry1Bb1, all of which exhibited no significant difference when compared to the untreated control.

The *Lygus* bioassays were expanded to include individual crystal preparations of TIC810, TIC812, and a mixture of TIC812 and ET37. Similar to the results described above, only the combination of the two proteins exhibited significant insecticidal activity. TIC810 plus ET29 and TIC812 plus ET37 exhibited significant mortality and mass reduction when compared to untreated controls or to the bioassays using only the individual proteins. However, combinations of TIC810 plus ET29 (or TIC809) exhibited greater mortality and mass reduction than the TIC812 plus ET37 combination.

The results of these bioassays indicated that neither TIC810 nor TIC812 alone are toxic to WTPB, and that a mixture of either TIC810 and ET29 or of TIC812 and ET37 is toxic to WTPB, similar to the results observed when tested against corn rootworm larvae.

Example 11

This example illustrates construction of cassettes for expressing TIC809 and/or TIC810, and homologs thereof.

Plant transformation vectors are constructed to achieve high-level expression of rootworm-toxic TIC809 and/or ET37 proteins in plants. Vectors containing TIC812 and ET37 coding sequences may be used to co-express TIC812 and ET37 protein, thereby achieving insect protected plants exhibiting high levels of in planta ET37 protein production. Co-expression of TIC810 along with ET37 is sufficient for achieving stable high levels of accumulation of ET37 in a host cell. Similarly, co-expression of TIC812 along with ET29 or even TIC809 is sufficient to achieve stable high levels of accumulation of ET29 or TIC809 in a host cell. As indicated hereinabove, It is anticipated that proteins of the Cyt1 and Cyt2 class that exhibits from about 15 to about 100 percent amino acid sequence similarity to ET29 and/or ET37 will exhibit improved expression and/or accumulation when expressed in a host cell along with TIC810, TIC812, or an orthologous or homologous protein exhibiting an amino acid sequence that exhibits from about 50 to about 100% amino acid sequence similarity to TIC810 or TIC812, and that any negative phenotypic effects caused by such Cyt protein expression will be ameliorated by co-expression of such Cyt protein with TIC810, TIC812, or variants thereof.

The above specification describes preferred embodiments of the present invention. It will be understood by those skilled in the art that, without departing from the scope and spirit of the present invention and without undue experimentation, the present invention can be performed within a wide range of equivalent parameters. While the present invention has been described in connection with specific embodiments thereof, it will be understood that it is capable of further modifications. The present invention is intended to cover any uses, variations, or adaptations of the invention following the principles of the invention in general. Various permutations and combination of the elements provided in all the claims that follow are possible and fall within the scope of this invention.

All publications, patents and published patent applications referred to in this specification are herein incorporated by reference as if each individual publication or patent was specially and individually stated to be incorporated by reference.

What is claimed is:

1. A method for enhancing the accumulation of a first insecticidal protein in a recombinant host cell, said method comprising:

contemporaneously expressing said first insecticidal protein, said first insecticidal protein selected from the group consisting of: ET37 as set forth in SEQ ID NO:2 or SEQ ID NO:18, ET29 as set forth in SEQ ID NO:8, and TIC809 as set forth in SEQ ID NO:14, with a second insecticidal protein, said second insecticidal protein selected from the group consisting of: TIC810 as set forth in SEQ ID NO:4 or SEQ ID NO:16, and TIC812 as set forth in SEQ ID NO:6 or SEQ ID NO:20, said first insecticidal protein and said second insecticidal protein being under the control of one or more heterologous promoters in said recombinant host cell, wherein said contemporaneous expression of said first insecticidal protein and said second insecticidal protein enhances the accumulation of the first protein compared to the accumulation of said first insecticidal protein expressed in a recombinant host cell in the absence of said second insecticidal protein.

2. A composition exhibiting insecticidal activity, said composition comprising TIC809 as set forth in SEQ ID NO:14 and TIC810 as set forth in SEQ ID NO:4 or SEQ ID NO:16.

3. A method for making a plant cell resistant to an insect pest, the method comprising:

transforming said plant cell to express an insecticidally effective amount of a toxin composition, said toxin composition comprising a first protein selected from the group consisting of: ET29 as set forth in SEQ ID NO:8, ET37 as set forth in SEQ ID NO:2 or SEQ ID NO:18, and TIC809 as set forth in SEQ ID NO:14, and a second protein selected from the group consisting of: TIC810 as set forth in SEQ ID NO:4 or SEQ ID NO:16 and TIC812 as set forth in SEQ ID NO:6 or SEQ ID NO:20.

4. The method of claim 3, wherein said plant cell is selected from the group consisting of a monocot plant cell and a dicot plant cell.

5. The method of claim 4, wherein:

(1) said monocot plant cell is selected from the group consisting of: corn, wheat, oat, rice, sorghum, milo, buckwheat, rye, grass, and barley plant cell, and (2) said dicot plant cell is selected from the group consisting of: alfalfa, apple, apricot, asparagus, bean, berry, blackberry, blueberry, canola, carrot, cauliflower, celery, cherry, chickpea, citrus tree, cotton, cowpea, cranberry, cucumber, cucurbit, egg plant, fruit tree, grape, lemon, lettuce, linseed, melon, mustard, nut bearing tree, okra, orange, pea, peach, peanut, pear, plum, potato, soybeans, squash, strawberry, sugar beet, sunflower, sweet potato, tobacco, tomato, turnip, and vegetable plant cells.

6. A transgenic plant or plant cell resistant to insect infestation, said plant or plant cell comprising a pesticidally effective amount of an insecticidal composition, said insecticidal composition comprising a first polynucleotide encoding a first protein and a second polynucleotide encoding a second protein, wherein said first protein comprises an amino acid sequence selected from the group consisting of: SEQ ID NO:2, SEQ ID NO:8, SEQ ID NO:14, and SEQ ID NO:18, and said second protein comprises an amino acid sequence exhibiting at least 99% identity to the amino acid sequence set forth in SEQ ID NO:4 or SEQ ID NO:16.

7. The transgenic plant or plant cell of claim 6, wherein said transgenic plant or plant cell is selected from the group consisting of: a dicot plant or dicot plant cell and a monocot plant or monocot plant cell, said dicot plant or dicot plant cell being further selected from the group consisting of: alfalfa, apple, apricot, asparagus, bean, berry, blackberry, blueberry, canola, carrot, cauliflower, celery, cherry, chickpea, citrus tree, cotton, cowpea, cranberry, cucumber, cucurbit, egg plant, fruit tree, grape, lemon, lettuce, linseed, melon, mustard, nut bearing tree, okra, orange, pea, peach, peanut, pear, plum, potato, soybeans, squash, strawberry, sugar beet, sunflower, sweet potato, tobacco, tomato, turnip, and vegetable plant or plant cell, and said monocot plant being further selected from the group consisting of: corn, wheat, oat, rice, sorghum, milo, buckwheat, rye, grass, and barley plant or plant cell.

8. The transgenic plant or plant cell of claim 6, wherein said transgenic crop plant further comprises an additional insecticidal agent toxic to the insect infestation, wherein said additional insecticidal agent is selected from the group consisting of: a *Bacillus* toxin, a *Xenorhabdus* toxin, a *Photorhabdus* toxin, and a dsRNA specific for suppression of one or more essential genes in said insect.

9. An isolated and purified polynucleotide encoding an insecticidal protein, said protein comprising the amino acid sequence of SEQ ID NO:47.

10. An expression cassette for use in expressing an insecticidal protein in a recombinant host cell, wherein said expression cassette comprises, in operable linkage, a heterologous promoter sequence functional in said host cell and a nucleotide sequence encoding said insecticidal protein, wherein said insecticidal protein comprises the amino acid sequence as set forth in SEQ ID NO:4.

11. The expression cassette of claim 10, wherein said recombinant host cell is selected from the group consisting of: a bacterial cell, a fungal cell, a mammalian cell, and a plant cell.

12. The expression cassette of claim 11, wherein:

(a) said bacterial cell is selected from the group consisting of: a *Bacillus* species cell, a Enterobacteriacae species cell, a *Pseudomonas* species cell, a *Clostridium* species cell, and a *Rhizobium* species cell, and a *Agrobacterium* species cell; and (b) said plant cell is selected from the group of plants consisting of: a dicotyledonous plant and a monocotyledonous plant, said dicotyledonous plant being further selected from the group consisting of: alfalfa, apple, apricot, asparagus, bean, berry, blackberry, blueberry, canola, carrot, cauliflower, celery, cherry, chickpea, citrus tree, cotton, cowpea, cranberry, cucumber, cucurbit, egg plant, fruit tree, grape, lemon, lettuce, linseed, melon, mustard, nut bearing tree, okra, orange, pea, peach, peanut, pear, plum, potato, soybeans, squash, strawberry, sugar beet, sunflower, sweet potato, tobacco, tomato, turnip, and vegetable, and said monocotyledonous plant being further selected from the group consisting of: corn, wheat, oat, rice, sorghum, milo, buckwheat, rye, grass, and barley.

13. The expression cassette of claim 10, wherein said host cell is a plant cell and said expression cassette further comprises in operable linkage a sequence selected from the group consisting of: an expression enhancer sequence, an untranslated leader sequence, an intron sequence, a chloroplast targeting peptide encoding sequence, and a transcription termination and polyadenylation sequence.

14. A vector comprising the expression cassette of any one of claims 10-13.

15. The composition of claim 3, wherein said composition comprises a fusion of said TIC809 and said TIC810 as set forth in SEQ ID NO:47.

16. A commodity product comprising a detectable amount of:

a polynucleotide as set forth in SEQ ID NO:46;

(2) a fusion of TIC809 and TIC810 as set forth in SEQ ID NO:47; or (3) both SEQ ID NO:46 and SEQ ID NO:47.

17. The method of claim 3, wherein said first protein is TIC809 and said second protein is TIC810, and wherein said toxin composition comprises a fusion of said first protein and said second protein as set forth in SEQ ID NO:47.

18. The transgenic plant or plant cell of claim 6, wherein said first protein is TIC809 and said second protein is TIC810, and wherein said insecticidal composition comprises a fusion of said first protein and said second protein as set forth in SEQ ID NO:47.

19. A method for controlling Coleopteran or Hemipteran insect infestation of a plant, said method comprising providing in the diet of the insect the transgenic plant or plant cell of claim 6.

20. The method of claim 19, wherein said Coleopteran insect is a corn rootworm or said Hemipteran insect is a *Lygus* bug.

21. A method for protecting a crop in a field from insect infestation, said method comprising:

growing a transgenic crop plant in the field, wherein the transgenic crop plant comprises an insecticidally effective amount of a first protein and a second protein, wherein said first protein is selected from the group consisting of: ET37 as set forth in SEQ ID NO:2 or SEQ ID NO:18, ET29 as set forth in SEQ ID NO:8, and TIC809 as set forth in SEQ ID NO:14, and said second protein is selected from the group consisting of: TIC810 as set forth in SEQ ID NO:4 or SEQ ID NO:16 and TIC812 as set forth in SEQ ID NO:6 or SEQ ID NO:20, said first protein and said second protein expressed contemporaneously in said transgenic crop plant under the control of one or more heterologous promoters, thereby preventing an insect from surviving on said transgenic crop plant.

22. The method of claim 21, wherein said insect is selected from the group consisting of: a Coleopteran insect and a Hemipteran insect.

23. The method of claim 22, wherein said Coleopteran insect is a corn rootworm and said Hemipteran insect is a *Lygus* bug.

24. The method of claim 21, wherein said transgenic crop plant further comprises an additional insecticidal agent toxic to the same insect as said first protein and said second protein, wherein said additional insecticidal agent is selected from the group consisting of: a *Bacillus* toxin, a *Xenorhabdus* toxin, a *Photorhabdus* toxin, and a dsRNA specific for suppression of one or more essential genes in said insect.

* * * * *